US008338492B2

(12) United States Patent
Colson et al.

(10) Patent No.: US 8,338,492 B2
(45) Date of Patent: *Dec. 25, 2012

(54) FILMS AND PARTICLES

(75) Inventors: Yolonda L. Colson, Dover, MA (US); Solomon Azouz, Dallas, TX (US); Mark W. Grinstaff, Brookline, MA (US); Jesse Wolinsky, Brookline, MA (US); Aaron Griset, Medford, MA (US)

(73) Assignees: The Trustees of the Boston University, Boston, MA (US); The Brigham and Women's Hospital, Inc., Boston, MA (US)

( * ) Notice: Subject to any disclaimer, the term of this patent is extended or adjusted under 35 U.S.C. 154(b) by 264 days.

This patent is subject to a terminal disclaimer.

(21) Appl. No.: 12/818,693

(22) Filed: Jun. 18, 2010

(65) Prior Publication Data

US 2012/0107365 A1    May 3, 2012

Related U.S. Application Data

(60) Continuation of application No. 12/690,607, filed on Jan. 20, 2010, which is a division of application No. 11/756,587, filed on May 31, 2007, now Pat. No. 7,671,095.

(60) Provisional application No. 60/809,344, filed on May 31, 2006, provisional application No. 60/844,122, filed on Sep. 13, 2006.

(51) Int. Cl.
*A61K 47/06* (2006.01)

(52) U.S. Cl. .................................................. 514/772.3

(58) Field of Classification Search ........................ None
See application file for complete search history.

(56) References Cited

U.S. PATENT DOCUMENTS

| | | | |
|---|---|---|---|
| 3,305,605 | A | 2/1967 | Hostettler et al. |
| 3,324,070 | A | 6/1967 | Cox et al. |
| 3,379,693 | A | 4/1968 | Cox et al. |
| 4,900,785 | A | 2/1990 | Leitz et al. |
| 4,908,416 | A | 3/1990 | Eichenauer et al. |
| 4,912,168 | A | 3/1990 | Eichenauer et al. |
| 4,965,300 | A | 10/1990 | Eichenauer et al. |
| 5,634,931 | A | 6/1997 | Kugel |
| 5,824,082 | A | 10/1998 | Brown |
| 6,093,792 | A | 7/2000 | Gross et al. |
| 6,114,458 | A | 9/2000 | Hawker et al. |
| 6,280,453 | B1 | 8/2001 | Kugel |
| 6,734,257 | B2 | 5/2004 | Windisch et al. |
| 7,671,095 | B2 | 3/2010 | Colson et al. |
| 2004/0167276 | A1 | 8/2004 | Windisch et al. |
| 2005/0019404 | A1 | 1/2005 | Sung et al. |
| 2007/0077272 | A1 | 4/2007 | Li et al. |
| 2007/0141112 | A1 | 6/2007 | Falotico et al. |
| 2008/0075718 | A1 | 3/2008 | Colson et al. |

FOREIGN PATENT DOCUMENTS

| | | |
|---|---|---|
| FR | 1426964 | 3/1965 |
| FR | 1434145 | 3/1965 |
| WO | WO 2004028269 | 4/2004 |
| WO | WO 2009140131 | 11/2009 |

OTHER PUBLICATIONS

Adusumilli et al., "Intraoperative localization of lymph node metastases with a replication-competent herpes simplex virus", J. Thorac Cardiovasc. Surg., 132:1179-88 (2006).
Agrawal et al., "Evaluation of Poly(L-lactic Acid) as a Material for Intravascular Polymeric Stents", J. Biomaterials, 13:176-182 (1992).
Athanasiou et al., "Orthopaedic Applications for Pla-GPA Biodegradable Polymers", Arthroscopy: J. Arthroscopic and Related Surgery, 14(7):726-737 (1998).
Attawia et al., "Cytotoxicity testing of Poly(anhydride-co-imides) for Orthopedic Applications", J. Biomed. Mater. Res., 29:1233-1240 (1995).
Black et al., Polymerisation of Unsaturated Derivative of 1,2:5, 6-Di-O-isopropylidene-D-glucofuranose, J. of the Chem. Soc., 4433-4439 (1963).
Chiu et al., J. "Synthesis Functional Poly(carbonate-b-ester) Copolymers and Micellar Characterizations", Applied Polymer Science, 106(1):283-292 (2007).
Compan et al., "Response of Acrylate Polymers Containing Substituted 1, 3-Dioxacycloheane Groups in the Ester Residue to Mechanical and Electric Perturbation Fields", Polymer, 42(9):4339-4346 (2001).
Diaz-Calleja et al, "Comparative Study of Mechanical and Dielectric Properties of Glassy Acrylic Polymers Containing 1, 3-Dioxane Rings in Their Structures", Macromolecular Symposia, 147:191-199 (1999).
Diaz-Calleja et al., "Comparative Study of the Relaxation Behavior at Very Low Frequencies of Acrylate Polymers with Pendant 1, 3-Dioxane rings in their Structure", J. Applied Physics 84(8):4436-4442 (1998).
Diaz-Calleja et al., "Dielectric Relaxations in Polymers Containing Dioxacyclohexane Rings by Thermostimulated Depolarization Currents", Macromolecular Symposia, 191: 177-190 (2003).
Edlund et al., "Degradable Polymer Microspheres for Controlled Drug Delivery", Adv. Polymer Sci., 157:67-112 (2002).
Garcia et al., "Relaxation Behavior of Acrylate and Methacrylate Polymers Containing Dioxacyclopentane Rings in the Side Chains", J. Polymer Science, Part B: Polymer Physics 39(3):286-299 (2001).
Gillies et al., "Stimuli-Responsive Supramolecular Assemblies of Linear-Dendritic Copolymers", J. Am. Chem. Soc., 126:11936-43 (2004).
Heller et al., "Poly(ortho esters): Synthesis, Characterization, Properties and Uses", Adv. Drug Deliv. Rev., 54:1015:1039 (2002).
IUPAC-IUB Commission on Biochemical Nomenclature, Biochem., 11:942-944 (1972).
Jemal et al., "Cancer Statistics, 2006", CA Cancer J. Clin., 56:106-130 (2006).

(Continued)

*Primary Examiner* — Christina Bradley
(74) *Attorney, Agent, or Firm* — Fish & Richardson P.C.

(57) ABSTRACT

Described herein are compounds and processes that can be used to prepare polymer-based films, particles, gels and related compositions, and processes for delivery of agents, and other uses.

30 Claims, 18 Drawing Sheets

OTHER PUBLICATIONS

Laguna et al., "Experimental and Theoretical Studies on the Permeation of Argon Through Matrixes of Acrylic Polymers Containing 1,3-Dioxane Groups in Their Structure", J. Chemical Physics, 110(6):3200-3206 (1999).

Landfester et al., "Formulation and Stability Mechanisms of Polymerizable Miniemulsions", Macromolecules, 32:5222-8 (1999).

Legrand, et al., "Side-Chain Liquid Crystalline Polyacrylates Containing Heterocyclic Mesogenic Groups 1", Makromol. Chem., Dec. 1990, vol. 191, No. 12 pp. 2971-8.

Leitz et al., Mixtures of Aromatic Polycarbonates and/or Aromatic Polyesters With Special Copolymers, Off. Gaz. vol. 1112, No. 2, pp. 1064-1065; ISSN: 0360-5132 (1990).

Mantell et al., "Synthesis and Cross-linking of a New Series of Acrylate Polymers Containing m-dioxane Rings", J. Applied Polymer Science 9(11):3625-33 (1965).

Miller and Williams, "On the Biodegradation of Poly-$\beta$-Hydroxybutyrate (PHB) Homopolymer and Poly-$\beta$-Hydroxybutyrate-Hydroxyvalerate Copolymers", Biomaterials, 8:129-137 (1987).

Mullen et al., "New Aliphatic Poly(ester-carbonates) Based on 5-Methyl-5-Allyloxycarbonyl-1,3-Dioxan-2-one", J. Polymer Science, Part A: Polymer Chemistry 41(13):1978-1991 (2003).

Qadri et al., "Can Surgery for Cancer Accelerate the Progression of Secondary Tumors Within Residual Minimal Disease at Both Local and Systemic Levels?," Ann Thorac Surg, 80:1046-51 (2005).

Saiz et al., J. "Molecular Dynamics Simulations of the Time Dependent Dipolar Correlation Function for Esters Containing Substituted 1, 3-Dioxacyclohexane Rings in Their Structure", Physical Chemistry B, 101(50):10949-10953 (1997).

Sambrook et al., *Molecular Cloning: A Laboratory Manual* (2d ed., Cold Spring Harbor Laboratory Press, Cold Spring Harbor, N.Y. (1989).

Storey et al., "Synthesis of Novel Hydrophilic Poly(ester-carbonates) Containing Pendent Carboxylic Acid Groups", J. Macromolecular Science, Pure and Applied Chemistry A38(9), 897-917 (2001).

Wang et al., "Preparation and Characterization of Poly(lactic-co-glycolic acid) Microspheres for Targeted Delivery of a Novel Anticancer Agent, Taxol.", Chem. Pharm. Bull., (Tokyo) 44:1935-1940 (1996).

Wang, et al., "Synthesis and Characterization of Amphiphilic Block Copolymer Containing PVP and Poly(5-benzyloxytrimethylene carbonate", vol. 17, No. 2, pp. 239-242 (2006).

Wolinsky, et al., "Poly(carbonate ester)s Based on Units of 6-Hydroxyhexanoic Acid and Glycerol", Macromolecules 40:7065-68 (2007).

Zheng et al., *Acetal Copolymers: Syntheses and Modification*, Dissertation Abstracts International, vol. 55, No. 11B, p. 4877 (1994).

Sperling, L. H. et al, "Nomenclature in Polymer Science and Engineering", Chem. Abstracts Serv., First Published: ACS Division of Polymeric Materials: Science and Engineering (PMSE), 68, 341 (1993) downloaded on Sep. 18, 2009 http://www.polyacs.org/nomcl/pmse.noml.html (3 pp.).

He et al. "Synthesis and Characterization of Functionalizable and Photogpatternable Poly(-caprolactone-copRS-beta-malic acid)," Macromolecules 38, 8227-8234 (2005).

Azouz, et al., "Prevention of local tumor growth with paclitaxel-loaded microspheres", J. Thorac. Cardiovasc. Surg., 2008;135:1014-1021.

Gautam, et al., "Inhibition of experimental lung metastasis by aerosol delivery of PEI-p53 complexes", Mol. Ther. (2000) 2(4):318-23 (abstract only 1 page).

Matsuda et al., "Short Communication; New Infusion Device for Trans-tissue, Sustained Local Delivery of Anticancer Agent to Surgically Resected Tissue: Potential Use for Suppression of Local Recurrence of Pancreatic Cancer", Published Online Dec. 30, 2004, Wiley InterScience (www.interscience.wiley.com). DOI:10.1002/jbm,b.30186, pp. 203-207.

Ruel-Gariépy et al., "A thermosensitive chitosan-based hydrogel for the local delivery of paclitaxel", European J. of Pharmaceutics and Biopharmaceutics 57 (2004) pp. 53-63.

Wolinsky et al., "Prevention of in vivo lung tumor growth by prolonged local delivery of hydroxycamptothecin using poly(ester-carbonate)-collagen composites", *Journal of Controlled Release* 144 (2010) 280-287.

International Preliminary Report on Patentability dated Nov. 17, 2010, PCT/US2009/043089 7 pages.

International Search Report and Written Opinion, mailing date Jan. 6, 2010, PCT/US2009/043089 13 pages.

FILMS AND PARTICLES

CROSS-REFERENCE TO RELATED APPLICATIONS

This application is a continuation of U.S. patent application Ser. No. 12/690,607, filed Jan. 20, 2010, which is a divisional of U.S. patent application Ser. No. 11/756,587, filed May 31, 2007, which in turn claims the benefit of priority of U.S. Provisional Application Ser. No. 60/809,344, filed on May 31, 2006, and U.S. Provisional Application Ser. No. 60/844,122, filed on Sep. 13, 2006, each of which is incorporated herein by reference in its entirety.

STATEMENT AS TO FEDERALLY SPONSORED RESEARCH

This invention was made with Government support under U.S. Army Cooperative agreement No. DAMD-17-02-2-0006. The Government has certain rights in the invention.

FIELD OF THE INVENTION

Provided herein are compounds and processes to prepare polymer based films, particles, gels, and related compositions, and processes for delivery of agents.

BACKGROUND OF THE INVENTION

Medicine traditionally utilizes pharmacologic agents or surgical interventions for the treatment of disease. Specific targeting or localization of pharmacologic or biological agents to desired organs and tissues is a complex challenge. For example, cancer is a leading cause of death for both men and women in the United States (Jemal et al., CA Cancer J. Clin., 56:106-130, 2006). Current methods of cancer treatment include chemotherapy, radiation treatment, and surgical resection. As evidenced by high rates of cancer recurrence and low survival, treatments of conditions such as cancer often remain relatively ineffective.

Other diseases and conditions which utilize drug delivery technologies include immunological applications, pain control, wound healing, infectious disease, transplants, and the development of vaccines. Potential drug candidates often present solubility, toxicity, and pharmacokinetic considerations. Thus, there is a widespread need for targeted and sustained delivery of therapeutic agents.

Certain polyesters, polycarbonates, and polyamides are biodegradable polymers with low toxicity and degradation properties. Such polymers include poly(ε-caprolactone), poly(p-dioxanone), poly(trimethylene carbonate), poly (amino acids), and most notably poly(glycolic acid) and poly (lactic acid) (see, e.g., Agrawal et al., Biomaterials, 13:176-182, 1992; Attawia et al., J. Biomed. Mater. Res., 29:1233-140, 1995; Heller et al., Adv. Drug Deliv. Rev., 54:1015-1039, 2002; Miller and Williams, Biomaterials, 8:129-137, 1987; and Athanasiou et al., Arthroscopy, 14:726-737, 1998). These polymers are used in a variety of applications including the delivery of therapeutic agents. However, physical properties of the aforementioned polymers are often limited by monomer selection, polymerization techniques, and post-polymerization modifications. Properties of interest include thermal transition temperatures, bulk strength, flexibility, elasticity, degradation, crystallinity, and hydrophobicity. When polymers are utilized for in viva applications, the physical properties of the material affect host response. Hence, a need exists for polymers and delivery systems with desired characteristics that are effective for treatment of diseases and conditions.

SUMMARY OF THE INVENTION

The invention is based, at least in part, on the discovery that certain polymer films and particles can be utilized therapeutically and/or cosmetically. For example, many of the films and particles described herein can be used for the controlled, localized, and sustained delivery of various agents for treatment of diseases and conditions. Provided herein are compounds and processes to prepare polymer based films, particles, gels, and related compositions, and processes for delivery of agents. Provided herein are polymeric films and particles that deliver one or more agents, such as one or more therapeutic agents, to a local site, where the release of the one or more agents from the film or particle is initiated by a pH change. Also provided are biodegradable polymers.

In one aspect, the invention features oligomers or polymers having a repeat unit represented by Formula XX:

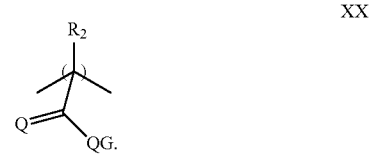

In such oligomers or polymers, Q is selected from among O, S, Se, or NH; G is selected from among the following structures:

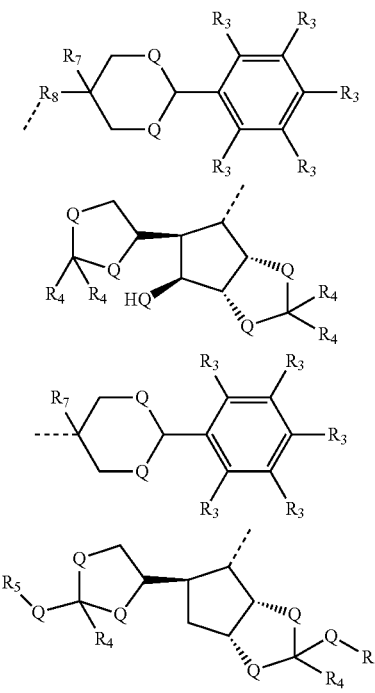

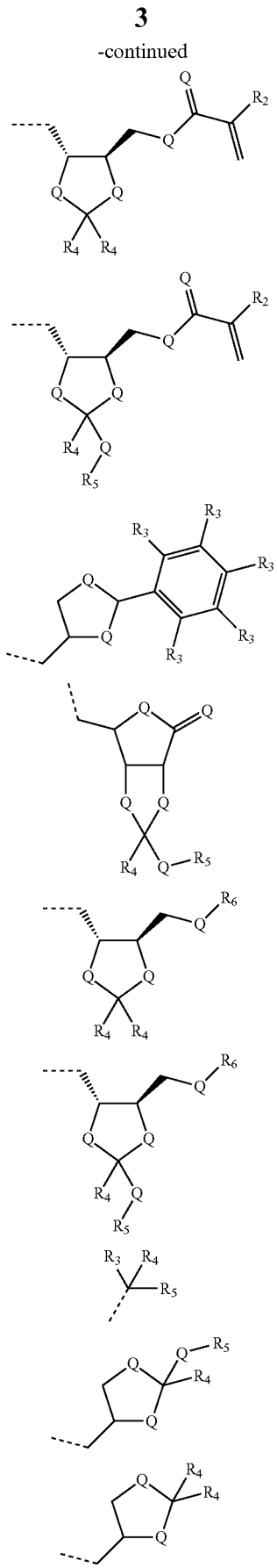

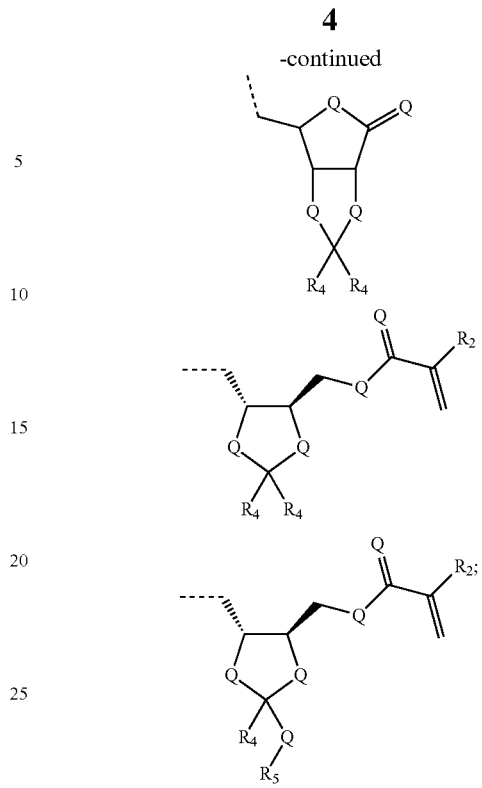

$R_2$ is selected from among hydrogen, a straight or branched alkyl, cycloalkyl, aryl, olefin, silyl, alkylsilyl, arylsilyl, alkylaryl, arylalkyl, or fluorocarbon chain of 1-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; $R_3$ is selected from among hydrogen, methoxy, ethoxy, amino, a straight or branched alkyl, cycloalkyl, aryl, olefin, silyl, alkylsilyl, arylsilyl, alkylaryl, or arylalkyl chain of 1-10 carbons; $R_4$, $R_5$, and $R_6$ are each independently selected from among a straight or branched alkyl, cycloalkyl, aryl, olefin, silyl, alkylsilyl, arylsilyl, alkylaryl, or arylalkyl chain of 1-10 carbons; and $R_7$ and $R_8$ are each independently selected from among hydrogen, a straight or branched alkyl, cycloalkyl, aryl, olefin, alkylaryl, or arylalkyl chain of 1-50 carbons, wherein each alkyl, cycloalkyl, aryl, olefin, alkylaryl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

In some embodiments, the oligomers or polymers are represented by Formula XX':

XX'

In such embodiments, n is an integer from 2-750, and each oligomeric or polymeric chain has a terminal group, the terminal group being selected from among amines, thiols, amides, phosphates, sulphates, hydroxides, alkenes, and alkynes.

In another aspect, the invention features oligomers or polymers, or portions thereof, that are represented by Formula XXI, XXII, XXIII, XXIV, XXV, XXVI, XXVII, XXVIII, XXIX, XXX, XXXI, XXXII, XXXIII, XXXIV, XXXV, XXXVI or XXXVII:

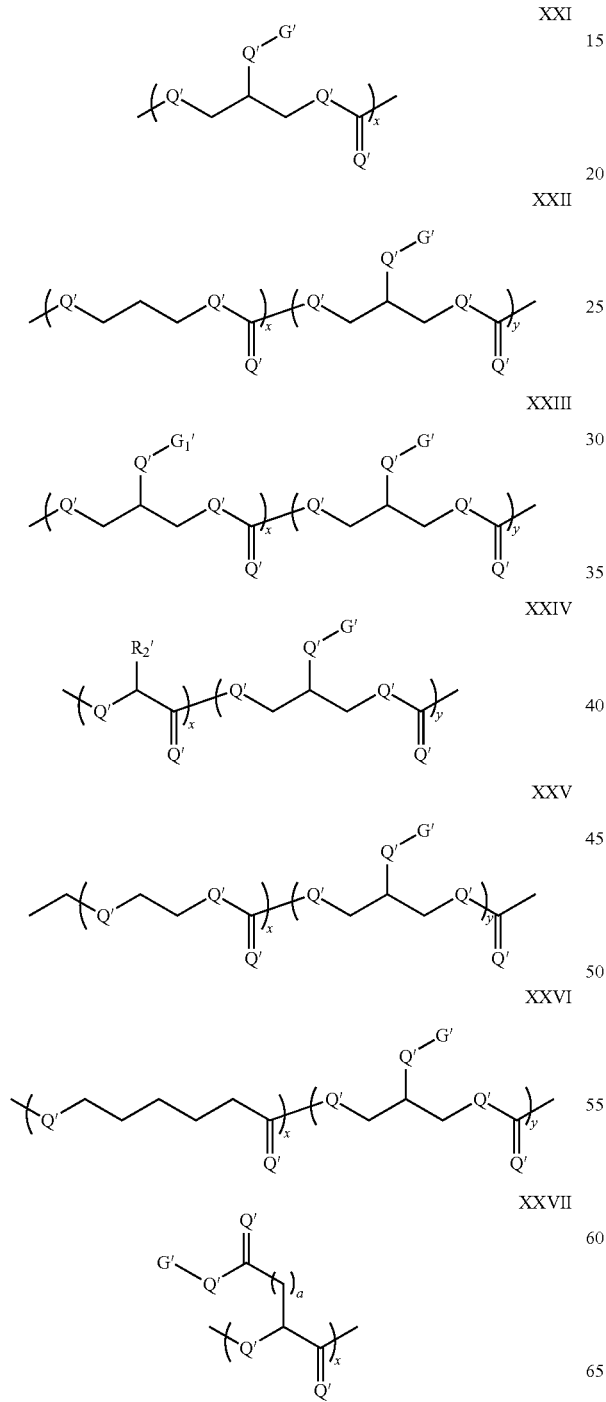

XXXVII

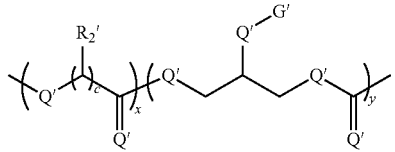

In such oligomers or polymers, or portions thereof, Q' is independently selected from among O, S, Se, or NH; G', $G_1'$, and $G_2'$ are each independently selected from among the following structures:

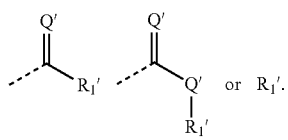

$G_1'$ and $G_2'$ are not the same; $R_1'$ is selected from among a straight or branched alkyl, cycloalkyl, aryl, olefin, silyl, alkylsilyl, arylsilyl, alkylaryl, arylalkyl, or fluorocarbon chain of 3-50 carbons, wherein each alkyl, cycloalkyl, aryl, olefin, silyl, alkylsilyl, arylsilyl, alkylaryl, arylalkyl or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or $R_1'$ is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or $R_1'$ is selected from among a photocrosslinkable or ionically crosslinkable group; $R_2'$ is selected from among hydrogen, a straight or branched alkyl, cycloalkyl, aryl, olefin, silyl, alkylsilyl, arylsilyl, alkylaryl, arylalkyl, or fluorocarbon chain of 1-50 carbons. Each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; x and y are each independently selected from an integer of 2-750; a is selected from an integer of 1-25; b is selected from an integer of 1-14; c is selected from an integer of 1-14; and each polymeric terminal group is selected from among amines, thiols, amides, phosphates, sulphates, hydroxides, metals, alkanes, alkenes and alkynes.

In another aspect, the invention features oligomers or polymers, or portions thereof, represented by Formula XXXVIII:

XXXVIII

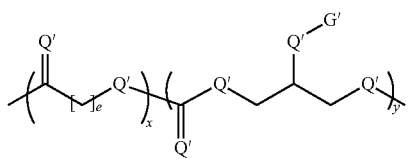

In such oligomers or polymers, or portions thereof; Q' is independently selected from among O, S, Se, or NH;

G' is selected from among

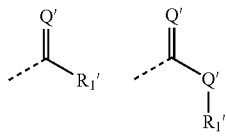

or $R_1'$; $R_1'$ is selected from among a straight or branched alkyl, cycloalkyl, aryl, olefin, silyl, alkylsilyl, arylsilyl, alkylaryl, arylalkyl, or fluorocarbon chain of 3-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or $R_1'$ is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or $R_1'$ is selected from among a photocrosslinkable or ionically crosslinkable group; x and y are each independently selected from an integer of 2-750; e is selected from an integer of 1-8; and each polymeric terminal group is selected from among amines, thiols, amides, phosphates, sulphates, hydroxides, metals, alkanes, alkenes and alkynes.

In another aspect, the invention features oligomers or polymers having a repeat unit represented by Formula XX:

XX

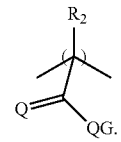

In such oligomers or polymers G includes a first group that is convertible to a second group different from the first group at a pH at or below about 6.0, such as below about 5.5, 5.0 or 4.5; $R_2$ is selected from among hydrogen, a straight or branched alkyl, cycloalkyl, aryl, olefin, silyl, alkylsilyl, arylsilyl, alkylaryl, arylalkyl, or fluorocarbon chain of 1-50 carbons. Each alkyl, cycloalkyl, aryl, olefin, silyl, alkylsilyl, arylsilyl, alkylaryl, arylalkyl or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; and Q is selected from among O, S, Se, or NH.

In another aspect, the invention features particles having a first volume and including an oligomer or polymer having a repeat unit represented by Formula XX:

XX

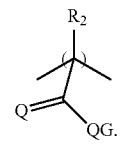

In such particles, G includes a first group that is convertible to a second group different from the first group at a pH at or below about 6.0, such as below about 5.5, 5.0, or 4.5; $R_2$ is selected from among hydrogen, a straight or branched alkyl, cycloalkyl, aryl, olefin, silyl, alkylsilyl, arylsilyl, alkylaryl, arylalkyl, or fluorocarbon chain of 1-50 carbons. Each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, monoor di-substituted amino, thiol, thioester, sulfate, phosphate, phosphonate, or halogen substituents; and Q is selected from among O, S, Se, or NH. When the particle is placed in an environment having a pH at or below about 6.0, the particle increases in volume from the first volume to a second volume that is more than two times the first volume after equilibrium is established.

Polymeric films or particles can include any oligomer or polymer described herein. In some instances, the polymeric particles include a first volume at a first pH, and a second volume at a second pH, different from the from the first pH. For example, the second volume is 1× or more greater than the first volume when the second pH is lower than the first pH, such as 4× or more greater than the first volume when the second pH is lower than the first pH, or 8× or more greater than the first volume when the second pH is lower than the first pH.

Any film or particle can include a therapeutic agent. For example, the agent can be a biologically active agent comprising one or more of an anti-cancer agent, an anti-biotic, an anti-neoplastic agent, an analgesic, an angiogenic, or an agent that promotes wound healing.

For example, the particles can be used for applying to one or more of the following: (i) a surgical resection margin, (ii) within a treated or untreated tumor or cavity, (iii) a target site of disease away from a surgical margin, and (iv) a lymph node.

The particles or films can have one or more layers.

The particles can have a diameter or less than 500 nanometers, such as less than 250 nanometers or less than 100 nanometers. For example, the particles can have a diameter of between about 1 nm and 2 microns.

Any of the particles described herein can be applied at a first site, such as a surgical margin, and then are carried by the body to a second site downstream of the first site, such as a lymph node. In such uses, it is desirable that the particles have a diameter of less than about 250 nanometers, such as less than 100 nanometers, or even less than 50 nanometers.

In another aspect, the invention features applying any film or particle described herein to a site using sutures, staples, and/or adhesives.

In another aspect, the invention features applying any film or particle described herein to treat pain, or to alter healing, e.g., to avoid scar formation.

Unless specific definitions are provided, e.g., as indicated below, the nomenclature used in connection with, and the laboratory procedures and techniques of, analytical chemistry, biochemistry, synthetic organic chemistry, and medicinal and pharmaceutical chemistry described herein are those known in the art. In the event that there is a plurality of definitions for terms herein, those in this section prevail.

As used herein, the abbreviations for any protective groups, amino acids, and other compounds are, unless indicated otherwise, in accord with their common usage, recognized abbreviations, or the IUPAC-IUB Commission on Biochemical Nomenclature, *Biochem.*, 11:942-944 (1972).

As used herein, use of the singular includes the plural unless specifically stated otherwise. As used herein, "or" means "and/or" unless stated otherwise. Furthermore, use of the term "including" as well as other forms, such as "includes," and "included," is not limiting.

As used herein, the terms "treating" or "treatment" encompass either or both responsive and prophylaxis measures, e.g., designed to inhibit, slow or delay the onset of a symptom of a disease or disorder, achieve a full or partial reduction of a symptom or disease state, and/or to alleviate, ameliorate, lessen, or cure a disease or disorder and/or its symptoms.

As used herein, amelioration of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

As used herein, the term "subject" is a human or an animal, typically a mammal, such as a cow, horse, dog, cat, pig, sheep, monkey, or other laboratory or domesticated animal. As used herein, the term "patient" includes human and animal subjects.

As used herein, the term "carrier" refers to a compound that facilitates the incorporation of another compound into cells or tissues. For example, dimethyl sulfoxide (DMSO) is a commonly used carrier for improving incorporation of certain organic compounds into cells or tissues.

As used herein, the term "pharmaceutical composition" refers to a chemical compound or composition capable of inducing a desired therapeutic effect in a subject. In certain embodiments, a pharmaceutical composition contains an active agent, which is the agent that induces the desired therapeutic effect. The pharmaceutical composition can contain a prodrug of the compounds provided herein. In certain embodiments, a pharmaceutical composition contains inactive ingredients, such as, for example, carriers and excipients.

As used herein, the term "therapeutically effective amount" refers to an amount of a pharmaceutical composition sufficient to achieve a desired therapeutic effect.

As used herein, the term "pharmaceutically acceptable" refers to a formulation of a compound that does not significantly abrogate the biological activity, a pharmacological activity and/or other properties of the compound when the formulated compound is administered to a subject. In certain embodiments, a pharmaceutically acceptable formulation does not cause significant irritation to a subject.

As used herein, pharmaceutically acceptable derivatives of a compound include, but are not limited to, salts, esters, enol ethers, enol esters, acetals, ketals, orthoesters, hemiacetals, hemiketals, acids, bases, solvates, hydrates, PEGylation, or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to chloroprocaine, choline, N,N'-dibenzyl-ethylenediamine, ammonia, diethanolamine and other hydroxyalkylamines, ethylenediamine, N-methylglucamine, procaine, N-benzyl-phenethylamine, 1-para-chlorobenzyl-2-pyrrolidin-1'-ylmethyl-benzimidazole, diethylamine and other alkylamines, piperazine and tris(hydroxymethyl)-aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl, or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl, or heterocyclyl. Pharmaceutically acceptable solvates and hydrates are complexes of a compound with one or more solvent or water molecules, or 1 to about 100, or 1 to about 10, or one to about 2, 3, or 4, solvent or water molecules.

"Alkyl" refers to an aliphatic hydrocarbon group which can be straight or branched having 1 to about 60 carbon atoms in the chain, and which preferably have about 6 to about 50 carbons in the chain. "Lower alkyl" refers to an alkyl group having 1 to about 8 carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. There can be optionally inserted along the alkyl chain one or more oxygen, silicon, sulfur, or substituted or unsubstituted nitrogen atoms, wherein the nitrogen substituent is lower alkyl. "Branched" refers to an alkyl group in which a lower alkyl group, such as methyl, ethyl, or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Useful alkyl groups include branched or straight chain alkyl groups of 6 to 50 carbon, and also include the lower alkyl groups of 1 to about 4 carbons and the higher alkyl groups of about 12 to about 16 carbons.

"Alkenyl" refers to an alkyl group containing at least one carbon-carbon double bond. The alkenyl group can be optionally substituted with one or more "alkyl group substituents." Exemplary alkenyl groups include vinyl, allyl, n-pentenyl, decenyl, dodecenyl, tetradecadienyl, heptadec-8-en-1-yl and heptadec-8,11-dien-1-yl.

"Alkynyl" refers to an alkyl group containing a carbon-carbon triple bond. The alkynyl group can be optionally substituted with one or more "alkyl group substituents." Exemplary alkynyl groups include ethynyl, propargyl, n-pentynyl, decynyl, and dodecynyl. Useful alkynyl groups include the lower alkynyl groups.

"Cycloalkyl" refers to a non-aromatic mono- or multicyclic ring system of about 4 to about 10 carbon atoms. The cycloalkyl group can be optionally partially unsaturated. The cycloalkyl group can be also optionally substituted with an aryl group substituent, oxo and/or alkylene. Representative monocyclic cycloalkyl rings include cyclopentyl, cyclohexyl, and cycloheptyl. Useful multicyclic cycloalkyl rings include adamantyl, octahydronaphthyl, decalin, camphor, camphane, and noradamantyl.

"Aryl" refers to an aromatic carbocyclic radical containing about 6 to about 10 carbon atoms. The aryl group can be optionally substituted with one or more aryl group substituents, which can be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene, and —NRR', where R and R' are each independently hydrogen, alkyl, aryl, and aralkyl. Exemplary aryl groups include substituted or unsubstituted phenyl and substituted or unsubstituted naphthyl.

"Acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl, and palmitoyl.

"Aroyl" means an aryl-CO— group, wherein aryl is as previously described. Exemplary aroyl groups include benzoyl, and 1- and 2-naphthoyl.

"Alkoxy" refers to an alkyl-O— group, wherein alkyl is as previously described. Exemplary alkoxy groups include methoxy, ethoxy, n-propoxy, i-propoxy, n-butoxy, and heptoxy.

"Aryloxy" refers to an aryl-O— group, wherein the aryl group is as previously described. Exemplary aryloxy groups, include phenoxy and naphthoxy.

"Alkylthio" refers to an alkyl-S— group, wherein alkyl is as previously described. Exemplary alkylthio groups include methylthio, ethylthio, i-propylthio, and heptylthio.

"Arylthio" refers to an aryl-S— group, wherein the aryl group is as previously described. Exemplary arylthio groups include phenylthio and naphthylthio.

"Aralkyl" refers to an aryl-alkyl- group, wherein aryl and alkyl are as previously described. Exemplary aralkyl groups include benzyl, phenylethyl, and naphthylmethyl.

"Aralkyloxy" refers to an aralkyl-O— group, wherein the aralkyl group is as previously described. An exemplary aralkyloxy group is benzyloxy.

"Aralkylthio" refers to an aralkyl-S— group, wherein the aralkyl group is as previously described. An exemplary aralkylthio group is benzylthio.

"Dialkylamino" refers to an —NRR' group, wherein each of R and R' is independently an alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group, wherein one of R and R' is hydrogen and the other of R and R' is alkyl as previously described.

"Dialkylcarbamoyl" refers to R'RN—CO— group, wherein each of R and R' is independently alkyl as previously described.

"Acyloxy" refers to an acyl-O— group, wherein acyl is as previously described.

"Acylamino" refers to an acyl-NH— group, wherein acyl is as previously described.

"Aroylamino" refers to an aroyl-NH— group, wherein aroyl is as previously described.

"Alkylene" refers to a straight or branched bivalent aliphatic hydrocarbon group having from 1 to about 30 carbon atoms. The alkylene group can be straight, branched, or cyclic. The alkylene group can be also optionally unsaturated and/or substituted with one or more "alkyl group substituents." There can be optionally inserted along the alkylene group one or more oxygen, sulphur, or substituted or unsubstituted nitrogen atoms, wherein the nitrogen substituent is alkyl as previously described. Exemplary alkylene groups include methylene (—$CH_2$—), ethylene (—$CH_2$—$CH_2$—), propylene ($CH_2$)$_3$—), cyclohexylene (—$C_6H_{10}$—CH=CH—CH=CH—, —($CF_2$)$_n$($CH_2$)$_m$—, wherein n is an integer from about 1 to about 50 and m is an integer from 0 to about 50, —($CH_2$)$_n$—N(R)—($CH_2$)$_m$—, wherein each of m and n is independently an integer from 0 to about 50 and R is hydrogen or alkyl, methylenedioxy and ethylenedioxy (—O—($CH_2$)$_2$—O—). An alkylene group can have about 2 to about 3 carbon atoms and can further have 6-50 carbons.

"Halo" or "halide" refers to fluoride, chloride, bromide, or iodide.

The term "agent" includes without limitation, medicaments, vitamins, mineral supplements, substances used for the treatment, prevention, diagnosis, cure or mitigation of disease or illness, substances that affect the structure or function of the body, or pro-drugs, which become biologically active or more active after they have been placed in a predetermined physiological environment.

A "bioactive agent" refers to an agent that is capable of exerting a biological effect in vitro and/or in vivo. The biological effect can be therapeutic in nature. As used herein, "bioactive agent" refers also to a substance that is used in connection with an application that is diagnostic in nature, such as in methods for diagnosing the presence or absence of a disease in a patient. The bioactive agents can be neutral or positively or negatively charged. Examples of suitable bioactive agents include pharmaceuticals and drugs, cells, gases and gaseous precursors (e.g., $O_2$), synthetic organic molecules, proteins, enzymes, growth factors, vitamins, steroids, polyanions, nucleosides, nucleotides, polynucleotides, and diagnostic agents, such as contrast agents for use in connection with magnetic resonance imaging, ultrasound, positron emission transmography, computed tomography, or other imaging modality of a patient.

"Genetic material" refers generally to nucleotides and polynucleotides, including deoxyribonucleic acid (DNA) and ribonucleic acid (RNA). The genetic material can be made by synthetic chemical methodology known to one of ordinary skill in the art, or by the use of recombinant technology, or by a combination of the two. The DNA and RNA can optionally comprise unnatural nucleotides and can be single or double stranded. "Genetic material" refers also to sense and antisense DNA and RNA, that is, a nucleotide sequence that is complementary to a specific sequence of nucleotides in DNA and/or RNA.

The polymers provided herein can be utilized therapeutically and/or cosmetically. For example, the polymers in any form described herein can be used to promote healing and/or that inhibit disease by targeting drug delivery to local and regional areas. The polymers provided herein can also be used for a variety of applications including, but not limited to, production of micro- and nanoparticles, films, coatings, sutures, and orthopedic materials. Such materials can be used to repair an injured tissue, organ, bone, or genetic defect. Other uses of the polymers provided herein include treatment of early, late, or previously treated malignancies, pretreatment of malignancies or other condition as a sensitizer to augment therapy of another agent such as with radiation sensitizers, avoidance of locoregional lymph node metastasis, augmentation of local wound healing and decrease in infection, manipulation of structure and abnormal scar formation, and for the treatment of post-operative pain. In certain embodiments, the polymers provided herein are used to treat cancer. For example, the polymers provided herein can be used to treat various malignancies, e.g., lung, colon, prostate, pancreas, or breast cancer. For example, when a film carrying one or more therapeutic agents is utilized to treat a cancer, it can be stapled, sutured and/or glued in place, e.g., with a cyanoacrylate resin.

The polymers provided herein can also be used to deliver any agent. The agent can be in any pharmaceutically acceptable form, including pharmaceutically acceptable salts. A large number of pharmaceutical agents are known in the art and are amenable for use in the pharmaceutical compositions of the polymeric materials described herein. Acceptable agents include, but are not limited to, chemotherapeutic agents, such as radiosensitizers, receptor inhibitors and agonists or other anti-neoplastic agents; immune modulators and bioactive agents, such as cytokines, growth factors, or steroids with or without the co-incorporation of tumor or pathogen antigens to increase the anti-neoplastic response as a means of vaccine development; local anesthetic agents; antibiotics; or nucleic acids as a means of local gene therapy.

Unless otherwise defined, e.g., as above, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety, unless noted otherwise. In case of conflict, the present specification, including definitions, will control. In addition, the materials, methods, and examples are illustrative only and not intended to be limiting.

Where reference is made to a URL or other such identifier or address, it understood that such identifiers can change and particular information on the internet can come and go, but equivalent information can be found by searching the internet. Reference thereto evidences the availability and public dissemination of such information.

Standard techniques can be used for chemical syntheses, chemical analyses, pharmaceutical preparation, formulation and delivery, and treatment of subjects. Standard techniques can be used for recombinant DNA, oligonucleotide synthesis, and tissue culture and transformation (e.g., electroporation, lipofection). Reactions and purification techniques can be performed, e.g., using kits according to manufacturer's specifications or as commonly accomplished in the art or as described herein. The foregoing techniques and procedures generally are performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989).

Other features and advantages of the invention will be apparent from the following detailed description, and from the claims.

BRIEF FIGURE DESCRIPTION

FIG. 1 is a bar graph showing the number of cells after treatment with 10-hydroxycamptothecin loaded films, control films without 10-hydroxycamptothecin, blank films, and 10-hydroxycamptothecin alone.

FIG. 2 is a bar graph showing the number of cells after treatment with 10-hydroxycamptothecin loaded films, control films without 10-hydroxycamptothecin, blank films, and 10-hydroxycamptothecin alone.

FIG. 8A shows the surface of the film (scale bar=3 microns), and FIG. 8B shows the film in cross-section (scale bar=10 microns).

DETAILED DESCRIPTION

Figure 1:
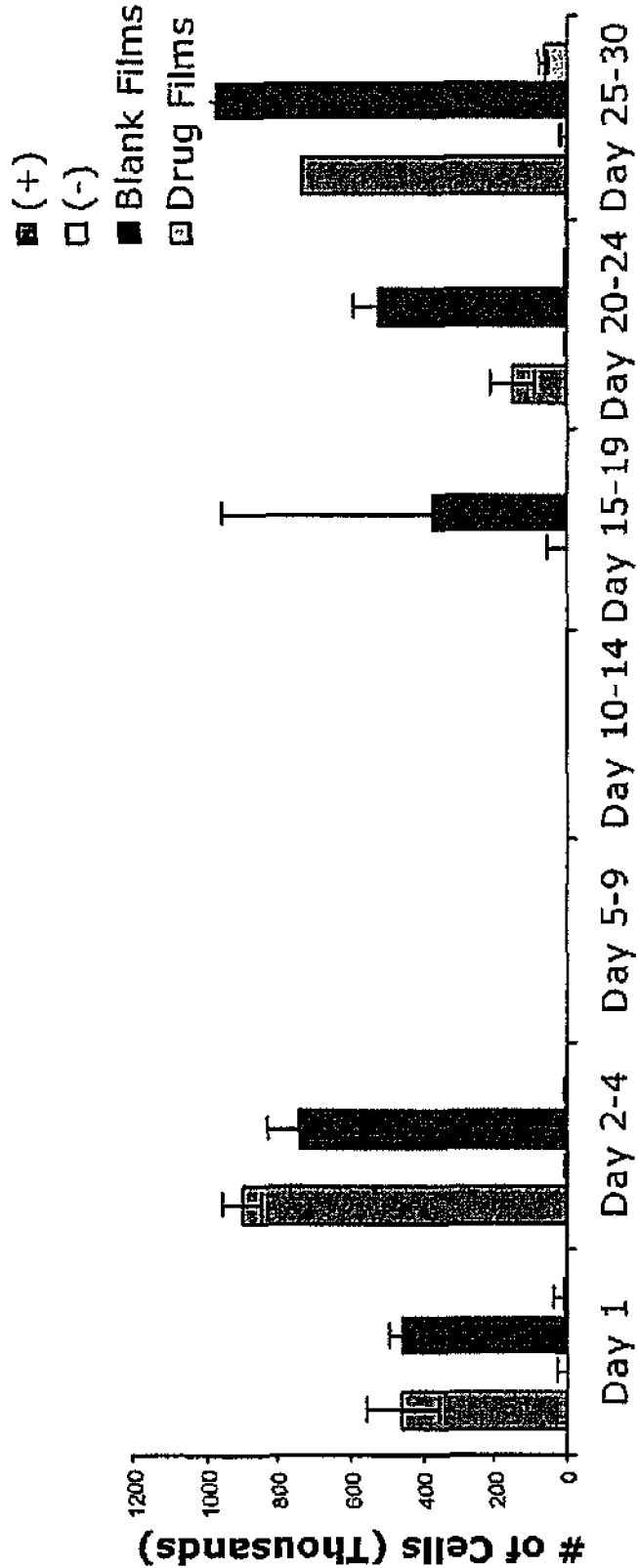

Provided herein are compounds and processes to prepare polymer based films, particles, gels, and related compositions, and processes for delivering agents. The following describes the synthesis of monomer units and the polymerization of those monomer units. Also provided is the synthesis of polymeric structures that incorporate therapeutic agents and methods of using such compositions to treat various diseases and disorders.

We will first describe vinyl monomers that can be used in making the new polymers, as well as methods of synthesizing the monomers. We will then describe methods of preparing and using the polymers. Then, we will describe the preparation of films and particles, as well as the incorporation of agents into polymeric structures. Finally, we will discuss the applications of the polymers and polymer-agent combinations.

A. Vinyl Monomer Units

As shown below, various vinyl monomer units are disclosed herein. These monomer units are used to prepare polymers, as described in further detail below. Vinyl monomer units include compounds of Formula I, II, and III:

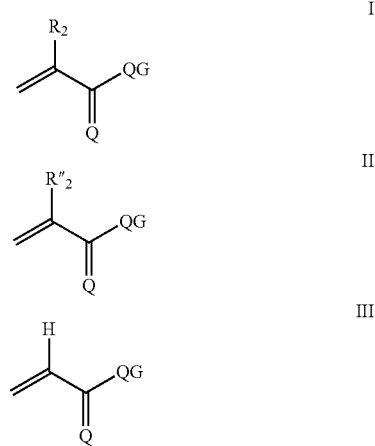

where each Q is independently selected from among O, S, Se, or NH;

G, or G and Q together, are selected from among:

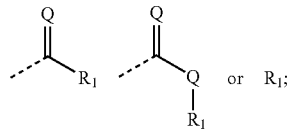

$R_1$ is selected from among a straight or branched alkyl, cycloalkyl, aryl, olefin, silyl, alkylsilyl, arylsilyl, alkylaryl, arylalkyl, or fluorocarbon chain of 3-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or $R_1$ is selected from among poly(ethylene glycol), poly (ethylene oxide), poly(hydroxyacid)), a carbohydrate, a protein, a polypeptide, an amino acid, a nucleic acid, a nucleotide, a polynucleotide, any genetic material, such as a DNA or RNA segment, a lipid, a polysaccharide, an antibody, a pharmaceutical agent, or any epitope for a biological receptor; or $R_1$ is selected from among a photocrosslinkable or ionically crosslinkable group; or $R_1$ comprises a first group that is convertible to a second group different from the first group at a pH at or below about 6.0;

$R_2$ is selected from among hydrogen, a straight or branched alkyl, cycloalkyl, aryl, olefin, silyl, alkylsilyl, arylsilyl, alkylaryl, arylalkyl or fluorocarbon chain of 1-50 carbons, wherein the alkyl, cycloalkyl, aryl, olefin, silyl, alkylsilyl, arylsilyl, alkylaryl, arylalkyl or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; and $R''_2$ is selected from among a straight or branched alkyl, cycloalkyl, aryl, olefin, silyl, alkylsilyl, arylsilyl, alkylaryl, arylalkyl, or fluorocarbon chain of 1-50 carbons, wherein the alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

In certain embodiments, a compound of Formula II is selected from among a compound shown below:

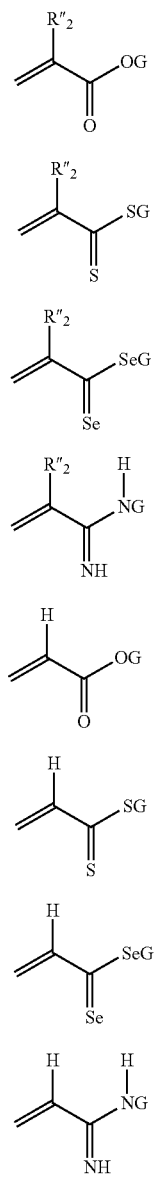

where R"$_2$ and G are independently selected as defined herein.

In certain embodiments, the compound of Formula II is a compound of Formula IV, where Q is oxygen. In certain embodiments, the compound of Formula II is a compound of Formula V, where Q is sulfur. In certain embodiments, the compound of Formula II is a compound of Formula VI, where Q is Se. In certain embodiments, the compound of Formula II is a compound of Formula VII, where Q is NH.

In other embodiments, a compound of Formula III is selected from among a compound Formula VIII, IX, X, or XI, as shown above. In certain embodiments, the compound of Formula III is a compound of Formula VIII where Q is oxygen. In certain embodiments, the compound of Formula III is a compound of Formula IX, where Q is sulfur. In certain embodiments, the compound of Formula III is a compound of Formula X, where Q is Se. In certain embodiments, the compound of Formula III is a compound of Formula XI, where Q is NH.

In other embodiments, a compound of Formula II is selected from among a compound Formula XII, XIII, or XIV, as shown below:

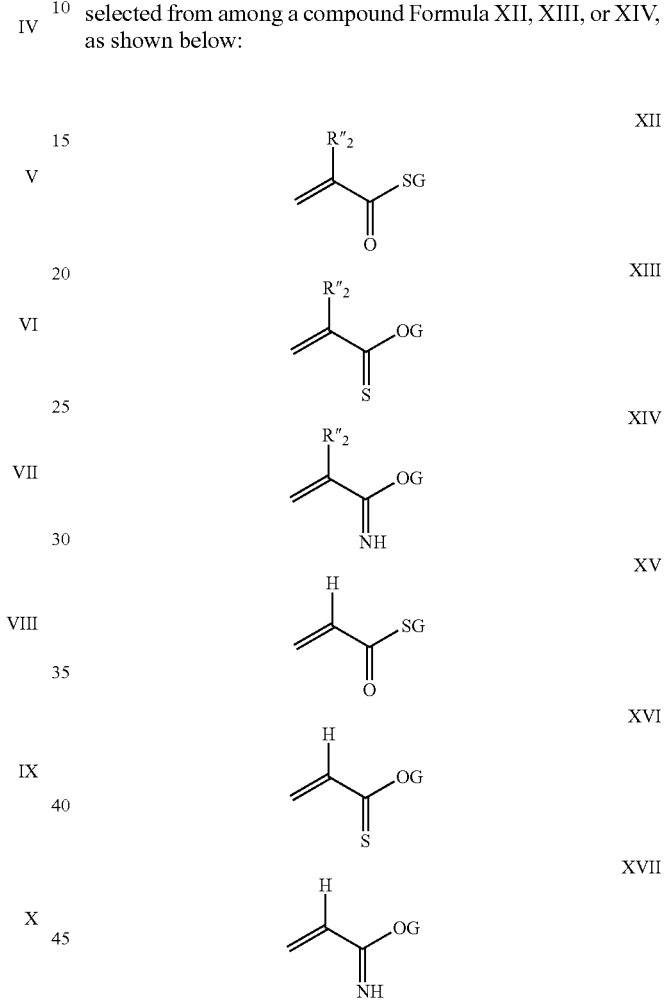

where R"$_2$ and G are independently selected as defined herein.

In certain embodiments, the compound of Formula II is a compound of Formula XII. In certain embodiments, the compound of Formula II is a compound of Formula XIII. In certain embodiments, the compound of Formula II is a compound of Formula XIV.

A compound of Formula III can also be independently selected from among a compound of Formula XV, XVI, or XVII, as shown above.

In certain embodiments, each G group is selected from among a group shown below:

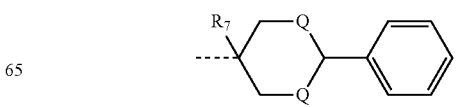

-continued

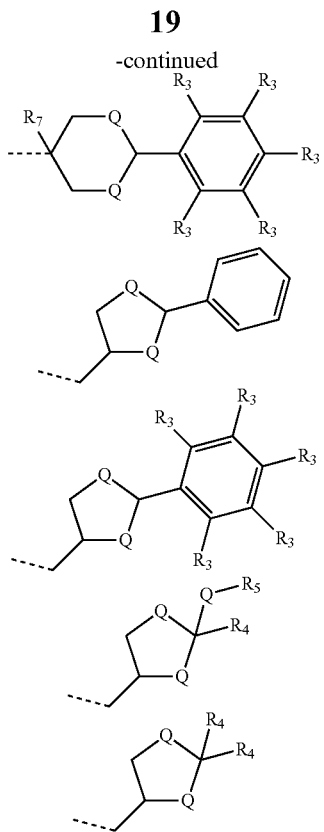

where each Q is independently selected from among O, S, Se, or NH;

R$_3$ is selected from among hydrogen, methoxy, ethoxy, amino, a straight or branched alkyl, cycloalkyl, aryl, olefin, silyl, alkylsilyl, arylsilyl, alkylaryl, or arylalkyl chain of 1-10 carbons;

R$_4$ and R$_5$ are each independently selected from among a straight or branched alkyl, cycloalkyl, aryl, olefin, silyl, alkylsilyl, arylsilyl, alkylaryl, or arylalkyl chain of 1-10 carbons; and R$_7$ is selected from among hydrogen, a straight or branched alkyl, cycloalkyl, aryl, olefin, alkylaryl, or arylalkyl chain of 1-50 carbons, wherein the alkyl, cycloalkyl, aryl, olefin, alkylaryl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

In certain embodiments, each G group is selected from among a group shown below:

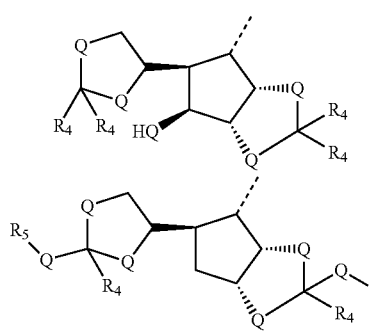

-continued

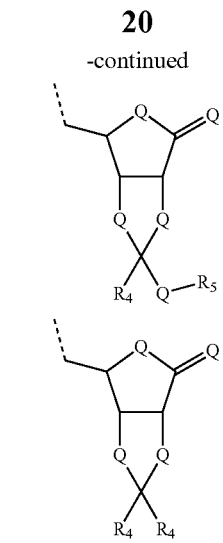

where each Q, R$_4$, and R$_5$ are each independently selected as defined herein.

In certain embodiments, each G group is selected from among a group shown below:

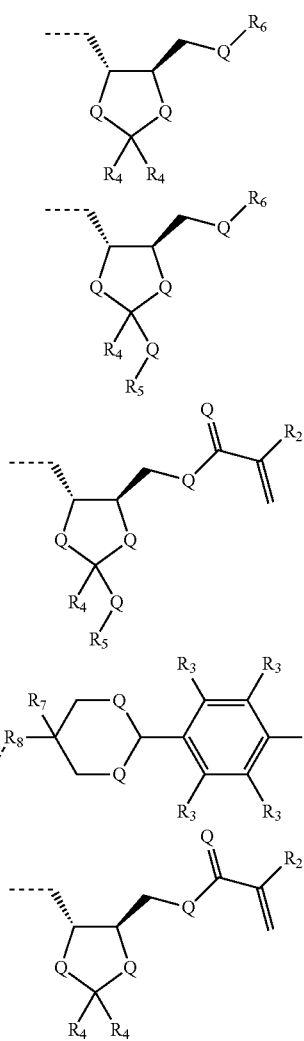

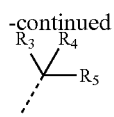

where each Q, $R_2$, $R_3$, $R_4$, $R_5$, and $R_7$ are selected as defined herein;

$R_6$ is selected from among a straight or branched alkyl, cycloalkyl, aryl, olefin, silyl, alkylsilyl, arylsilyl, alkylaryl, or arylalkyl chain of 1-10 carbons; and $R_8$ is selected from among hydrogen, a straight or branched alkyl, cycloalkyl, aryl, olefin, alkylaryl, or arylalkyl chain of 1-50 carbons, wherein the alkyl, cycloalkyl, aryl, olefin, alkylaryl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

In certain embodiments, each G group is selected from among a group shown below:

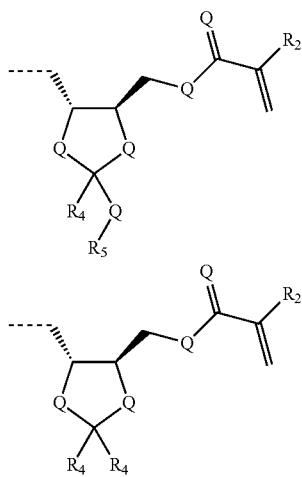

where each Q, $R_2$, $R_4$, and $R_5$ are independently selected as defined herein.

In certain embodiments, $R_2$ of Formula I is selected from among hydrogen, $C_1$-$C_{20}$ alkyl, cycloalkyl, alkylcycloalkyl, aryl, and heteroaryl. In certain embodiments, $R_2$ of Formula I is selected from among $C_1$-$C_{20}$ alkyl, cycloalkyl, aryl, and heteroaryl. In certain embodiments, the $R_2$ of Formula I is selected from among any group shown below:

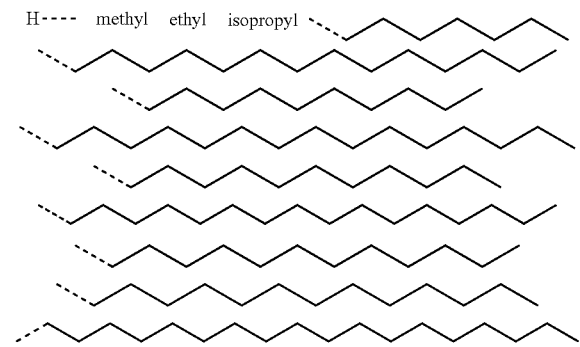

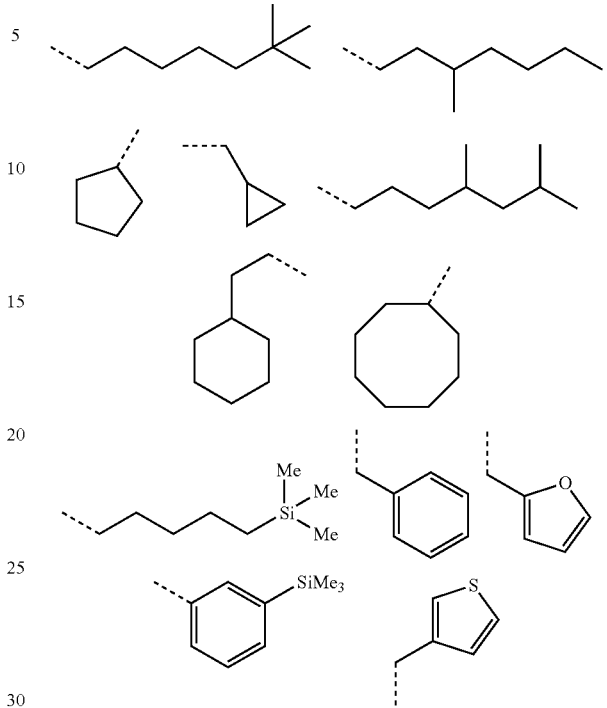

In certain embodiments, $R_2$ of Formula I is selected from among, $C_1$-$C_{20}$ alkyl, $C_1$-$C_{20}$ haloalkyl, heteroalkyl, cycloalkyl, alkylcycloalkyl, aryl, and heteroaryl, wherein the alkyl, haloalkyl, heteroalkyl, cycloalkyl, alkylcycloalkyl, aryl, and heteroaryl are optionally substituted. In certain embodiments, $R_2$ of Formula I is selected from among $C_1$-$C_{20}$ alkyl, wherein the alkyl is optionally substituted with halo, OH, $NH_2$, $NH(CH_3)$, $N(CH_3)_2$, or COOH. In certain embodiments, the $R_2$ of Formula I is selected from among any group shown below:

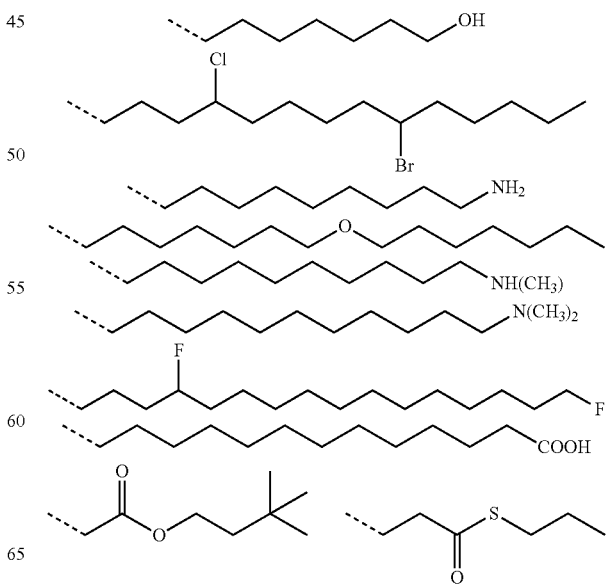

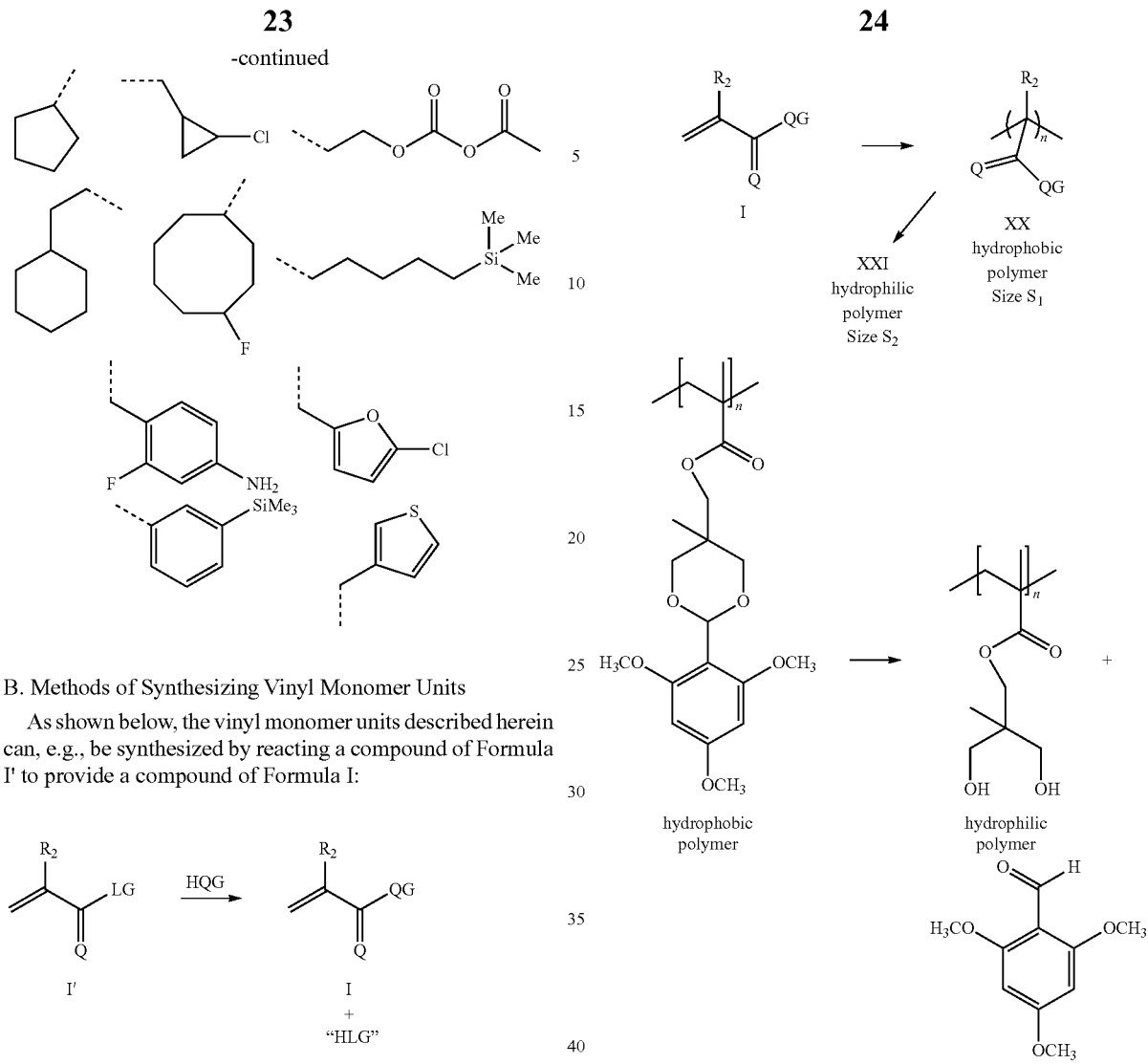

B. Methods of Synthesizing Vinyl Monomer Units

As shown below, the vinyl monomer units described herein can, e.g., be synthesized by reacting a compound of Formula I' to provide a compound of Formula I:

where each Q, G, or Q and G together, and $R_2$ are independently selected as defined herein;

and LG is a leaving group such as Cl or Br.

In one embodiment, a compound of Formula HQG, where Q and G are as defined herein, is dissolved in a solvent such as hexane, benzene, toluene, diethyl ether, chloroform, ethyl acetate, dichloromethane, 1,4-dioxane, tetrahydrofuran (THF), acetone, acetonitrile (MeCN), dimethylformamide (DMF), dimethyl sulfoxide, acetic acid, n-butanol, isopropanol, n-propanol, ethanol, methanol or water. In certain embodiments, a compound of Formula HQG is dissolved in THF. To this solution is added an acryloyl halide, such as methacryloyl chloride. In certain embodiments a base, such as a trialkyl amine (e.g. triethylamine), is added to the reaction mixture. The resulting product is a compound of Formula I.

In another embodiment, a compound of Formula I is prepared by reacting a compound of Formula HQG, where Q and G are defined as above, with an acryl anhydride, such as methacrylic anhydride, in the presence of a base, such as triethyl amine.

C. Methods of Polymerizing Vinyl Monomer Units

As shown below, a compound of Formula I can be polymerized to yield a compound of Formula XX:

where each Q, G, or G and Q together, and $R_2$ are independently selected as defined herein;

and n is an integer from 2-750; and each polymeric terminal group is selected from among amines, thiols, amides, phosphates, sulphates, hydroxides, alkenes, and alkynes.

Any method of vinyl polymerization known in the art can be used for this reaction. For example, a compound of Formula I can be reacted with a free-radical initiator. Free-radical initiators include halogen molecules, such as $Cl_2$, azo compounds, such as 2,2'-azobis(2-methylpropionitrile) (AIBN), and organic peroxides, such as di-t-butylperoxide. The polymerization can also be induced by light and a photoinitiator.

In one embodiment, a compound of Formula I is dissolved in a solvent, such as hexane, benzene, toluene, diethyl ether, chloroform, ethyl acetate, dichloromethane, 1,4-dioxane, tetrahydrofuran (THF), acetone, acetonitrile (MeCN), dimethylformamide (DMF), or dimethyl sulfoxide, and reacted with AIBN to yield a compound of Formula XX.

In certain embodiments, the polymer of Formula XX is hydrophobic and contains a pH sensitive group. G groups that are pH sensitive can be selected from among the groups described herein. As shown above, polymers of Formula XXI can be obtained by acid catalyzed hydrolysis from polymers of Formula XX, which contain a pH sensitive group. Any method of acid catalyzed hydrolysis known in the art can be used for this transformation. For example, the hydrolysis can be realized by immersing the polymer of Formula XX into a hydrochloric acid solution. The pH of the solution can be between 0.1 and 6.5. In other embodiments, the pH of the solution is between 1 and 5. For example, the pH can be below about 6.0, 5.5, 5.0, 4.5 or 4.0. In certain embodiments, the pH around 4. In other embodiments, the pH sensitive group can be removed under basic conditions and/or can be cleaved enzymatically.

As shown above, the hydrophilic polymer of Formula XXI can increase in size as compared to the hydrophobic polymer of Formula XX. The increased size ($S_2$) can be between 1.5 and 20 or more times the original size ($S_1$). In certain embodiments, the change in size from $S_1$ to $S_2$ is between 2 and 20 times, e.g., between 5 and 15, 5 and 10, 2 and 4, or 8 and 10 times, the original size.

E. Additional Vinyl Monomers, Polymerizations, and Hydrolysis Conditions

As shown below, a compound, e.g., compound 1, 2, 3, 4, 5, 6, 7, 8, 9, 10, 11, 12, 13, 14, 15, or 16, is polymerized alone or in combination with another monomer, to form a polymer, e.g., compound 1a, 2a, 3a, 4a, 5a, 6a, 7a, 8a, 9a, 10a, 11a, 12a, 13a, 14a, 15a, or 16a. Any method of polymerization described herein can be used for this transformation. For example, compound 1, 2, 3, 4, 5, 6, 7, 8, 9, 10, 11, 12, 13, 14, 15, or 16 can be reacted with a free-radical initiator, such as 2,2'-azobis(2-methylpropionitrile) (AIBN). The resulting compound 1a, 2a, 3a, 4a, 5a, 6a, 7a, 8a, 9a, 10a, 11a, 12a, 13a, 14a, 15a, or 16a is generally a hydrophobic polymer with a pH sensitive group. Any method of acid catalyzed hydrolysis known in the art can be used to cleave the pH sensitive group, as described herein. Enzymatic hydrolysis alone, or in combination with an acidic or basic solution, can also be used to cleave the group. For example, compound 1a, 2a, 3a, 4a, 5a, 6a, 7a, 8a, 9a, 10a, 11a, 12a, 13a, 14a, 15a, or 16a can be immersed in a hydrochloric acid solution. The resulting compound 1b, 2b, 3b, 4b, 5b, 6b, 9b, 10b, 11b, 12b, 13b, 14b, 15b, or 16b is a hydrophilic polymer and can increase in size between 1.5 and 20 or more times the original size of compound 1a, 2a, 3a, 4a, 5a, 6a, 7a, 8a, 9a, 10a, 11a, 12a, 13a, 14a, 15a, or 16a, respectively. For example, compound 1a, 2a, 3a, 4a, 5a, 6a, 7a, 8a, 9a, 10a, 11a, 12a, 13a, 14a, 15a, or 16a can be exposed to an acidic solution for various periods of time. Longer periods of exposure can lead to greater swelling. Alternative methods of achieving greater growth include raising the temperature and lowering the pH. The degree to which the particle swells can be reduced by adding difunctional crosslinkers. Difunctional crosslinkers include di-acrylate species and provide crosslinking between polymer chains that further restrict the size of the particle upon expansion.

Compounds 1, 2, 3, and 4 individually are polymerized to form a polymer, e.g., compound 1a, 2a, 3a, and 4a, as shown below:

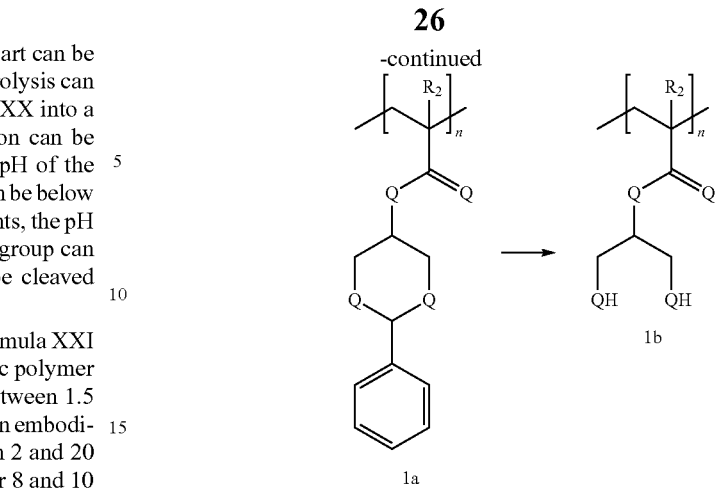

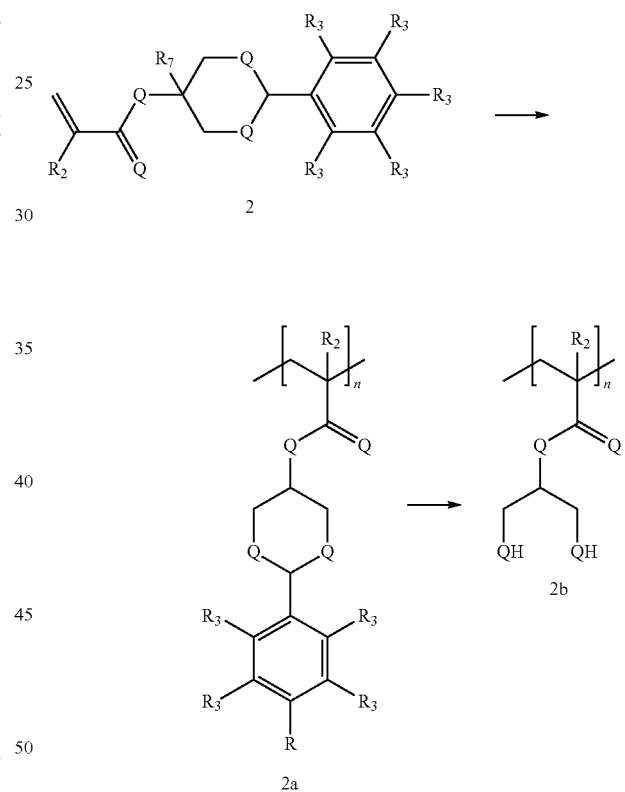

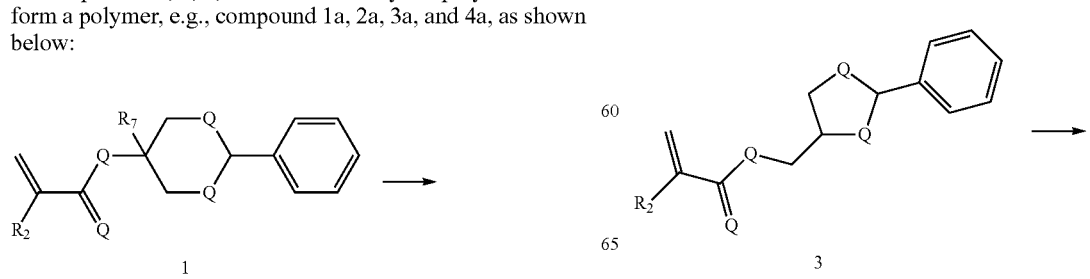

-continued

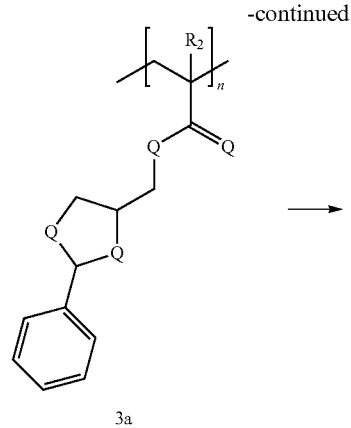

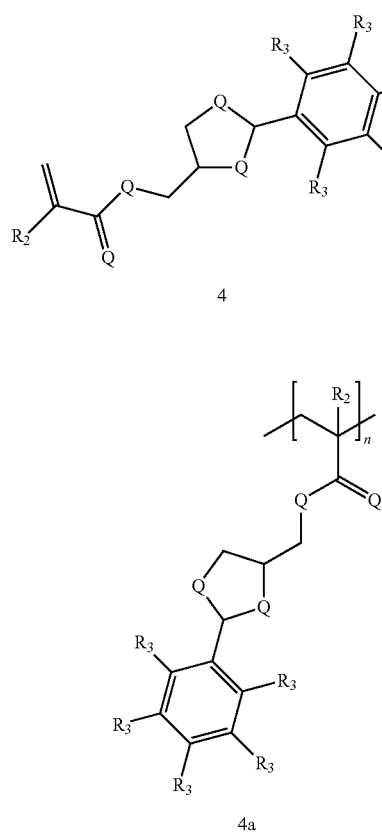

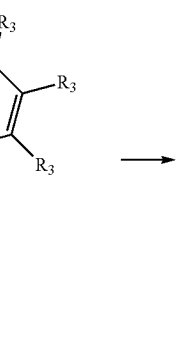

where each Q, n, $R_2$, $R_3$, $R_7$, and terminal group are independently selected as defined herein.

Compounds 5 and 6 are individually polymerized to form a polymer, e.g., compound 5a and 6a, as shown below:

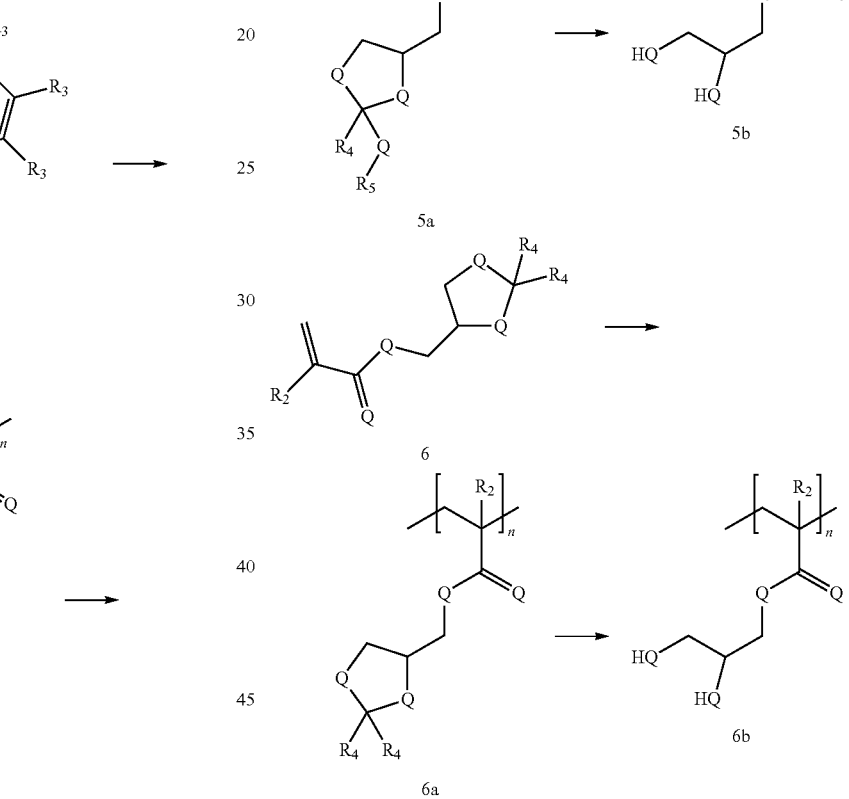

where each Q, n, $R_2$, $R_4$, $R_5$, and terminal group are independently selected as defined herein.

Compound 7 and 8 are individually polymerized to form a polymer, e.g., compound 7a and 8a, as shown below:

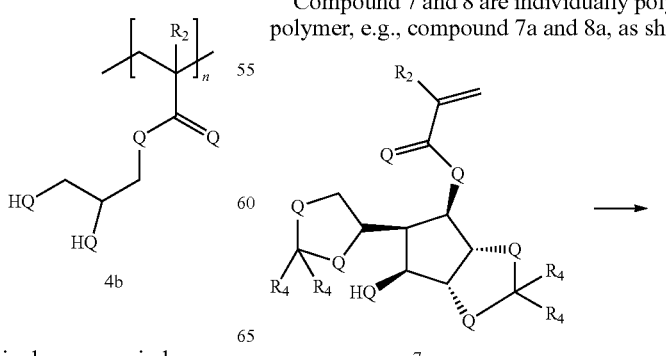

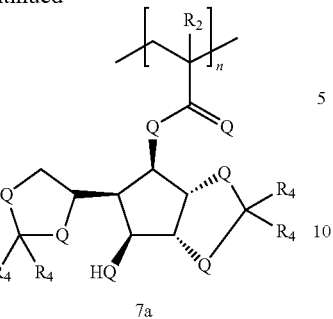

7a

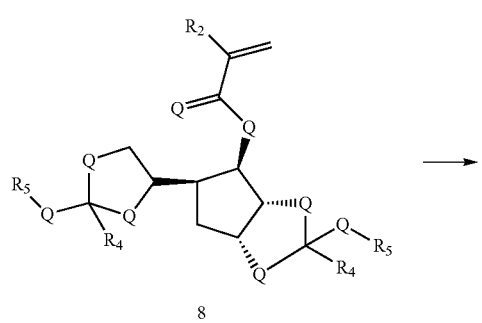

8

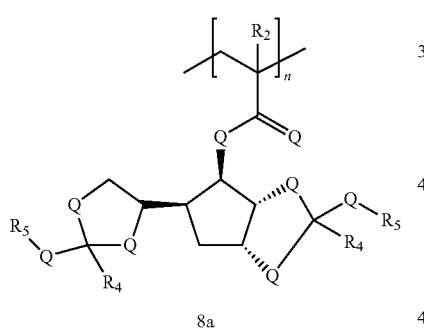

8a where each Q, n, R₂, R₄, R₅, and terminal group are independently selected as defined herein.

Compounds 9 and 10 are individually polymerized to form a polymer, e.g., compound 9a and 10a, as shown below:

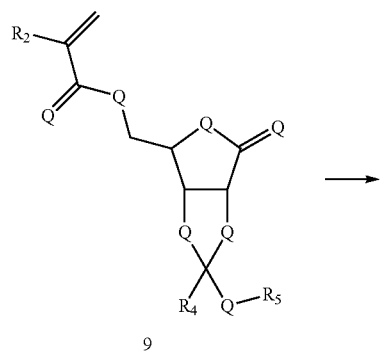

9

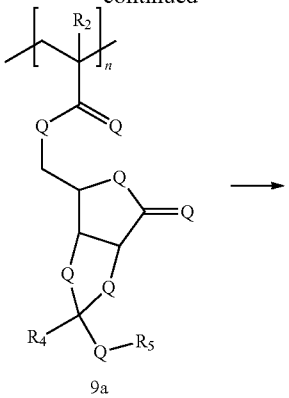

9a

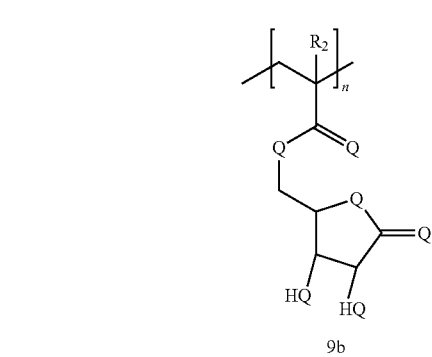

9b

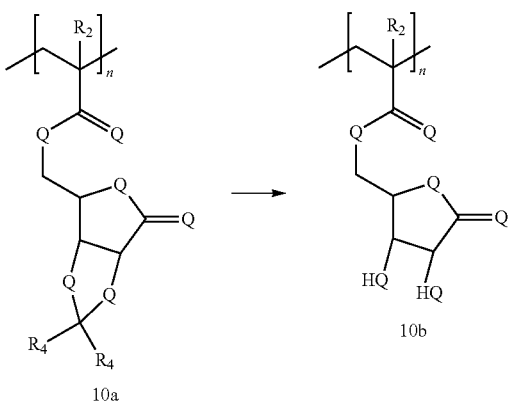

10

10a    10b where each Q, n, R₂, R₄, R₅, and terminal group are independently selected as defined herein.

Compounds 11 and 12 are individually polymerized to form a polymer, e.g., compound 11a and 12a, as shown below:

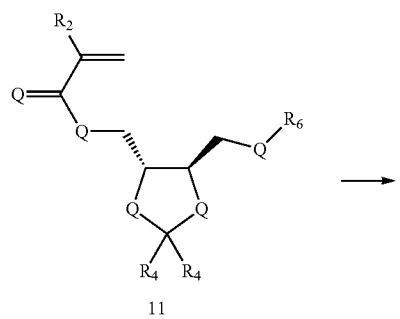
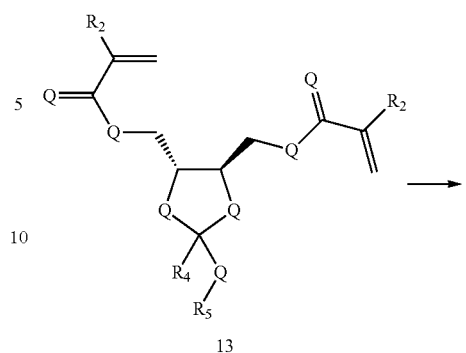
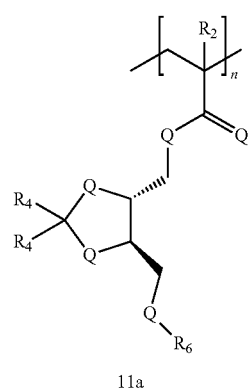
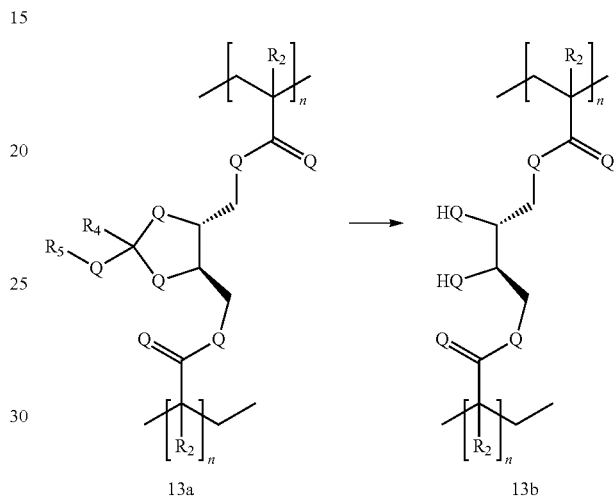
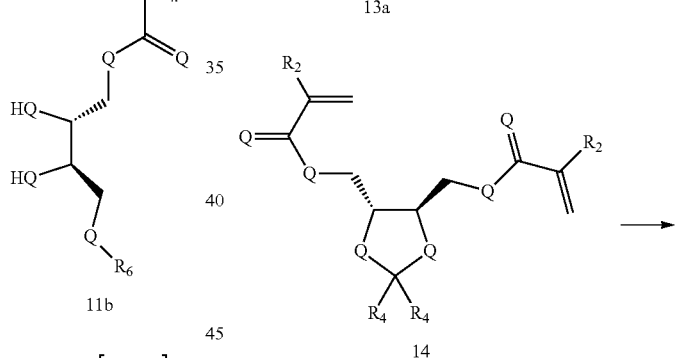
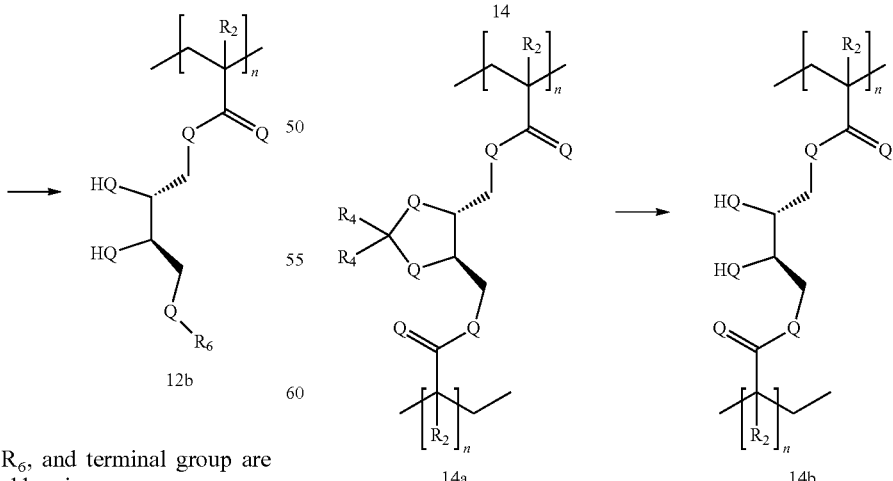
where each Q, n, $R_2$, $R_4$, $R_5$, $R_6$, and terminal group are independently selected as defined herein.
Compounds 13 and 14 are individually polymerized to form a polymer, e.g., compound 13a and 14a, as shown below:
where each Q, n, $R_2$, $R_4$, $R_5$, and terminal group are independently selected as defined herein.

Compounds 15 and 16 are individually polymerized to form a polymer, e.g., compound 15a and 16a, as shown below:

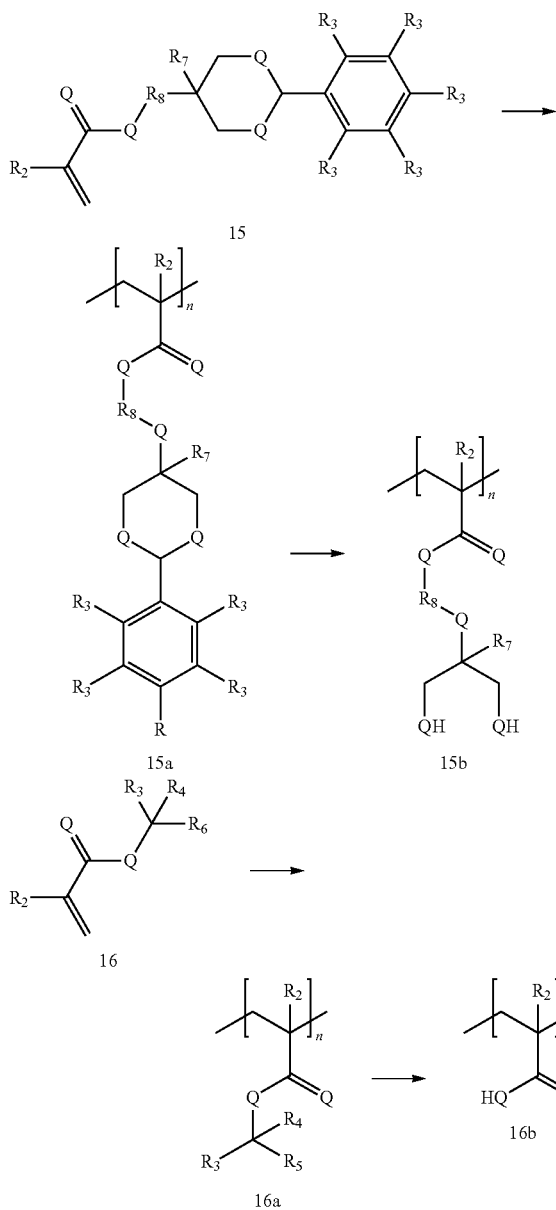

where each Q, n, $R_2$, $R_3$, $R_4$, $R_5$, $R_7$, $R_8$, and terminal group are independently selected as defined herein.

F. Vinyl Homopolymers and Copolymers

Provided herein are homopolymers prepared by polymerizing a compound of Formula I. In some embodiments, compounds of Formula I can be co-polymerized with any vinyl monomer described herein or known in the art. For example, Compound 1 can be co-polymerized with Compound 2. Compound 3 can be co-polymerized with any vinyl monomer known in the art, for example methyl methacrylate.

In other embodiments, any compounds of Formula I can be co-polymerized with any vinyl monomer described herein or known in the art to produce a random copolymer, a block copolymer, alternating copolymer, or a graft copolymer using any methods known in the art.

In additional embodiments, any compound of Formula I can be co-polymerized with any vinyl monomer described herein or known in the art to yield a linear, branched, star, or comb polymer, again, using any methods known in the art.

Any ratio of a single monomer relative to another monomer can be used to form a copolymer. Different ratios of monomer units impart different physical and chemical properties to the copolymer. Properties of interest include, but are not limited to, thermal transition temperature, bulk strength, crystallinity, flexibility, elasticity, and hydrophobicity. Thus, by varying monomer ratios, it is possible to afford a copolymer with desired characteristics. For example, introduction of a bulky hydrophobic side group will make the polymer more hydrophobic and reduce the rate of hydrolysis.

G. Additional Polymers such as Polyesters, Polyethers, and Polycarbonates

The following polyesters, polyethers, polyether-esters, polyamides, polycarbonates, and polyamino acids can be prepared according to the description provided below. These polymers can be used to make the films, particles, gels, and related compositions described herein, and can be used, e.g., to deliver various agents, e.g., bioactive agents.

As shown below, the chemical structures of various new polymers having Formulas XXI, XXII, XXIII, and XXIV:

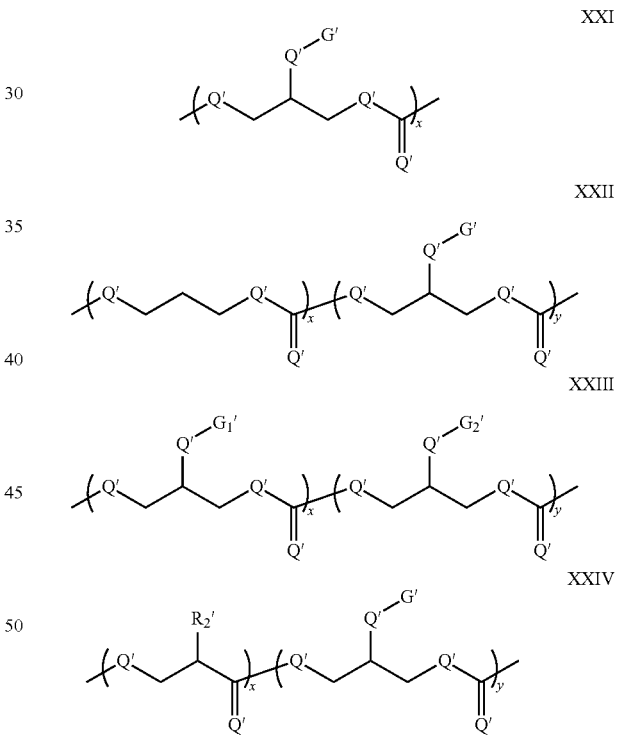

where each Q' is independently selected from among O, S, Se, or NH;

G', $G_1$', and $G_2$' are each independently selected from among:

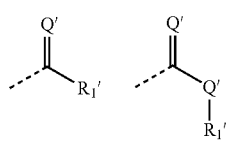

or $R_1$'; wherein $G_1$' and $G_2$' are not the same;

$R_1'$ is selected from among a straight or branched alkyl, cycloalkyl, aryl, olefin, silyl, alkylsilyl, arylsilyl, alkylaryl, arylalkyl or fluorocarbon chain of 3-50 carbons, wherein the alkyl, cycloalkyl, aryl, olefin, silyl, alkylsilyl, arylsilyl, alkylaryl, arylalkyl or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or $R_1'$ is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or $R_1'$ is selected from among a photocrosslinkable or ionically crosslinkable group; or $R_1'$ comprises a first group that is convertible to a second group different from the first group at a pH at or below about 6.0;

$R_2'$ is selected from among hydrogen, a straight or branched alkyl, cycloalkyl, aryl, olefin, silyl, alkylsilyl, arylsilyl, alkylaryl, arylalkyl, or fluorocarbon chain of 1-50 carbons, wherein the alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

x and y are each independently selected from an integer of 1-750; and each polymeric terminal group is selected from among amines, thiols, amides, phosphates, sulphates, hydroxides, metals, alkanes, alkenes, and alkynes.

Also provided are compounds of Formula XXV and XXVI, as shown below:

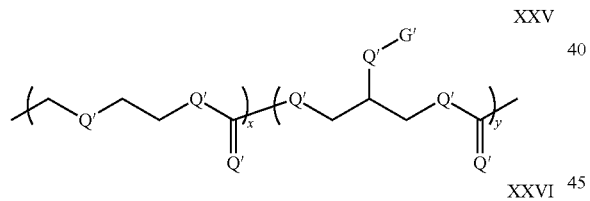

XXV

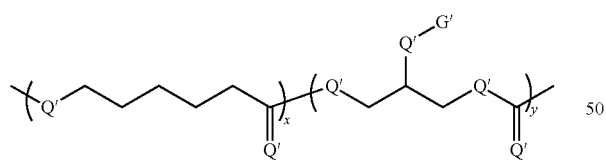

XXVI where each Q', x, y, and terminal group are independently selected as defined herein.

Also provided are compounds of Formula XXVII, XXVIII, XXIX, and XXX as shown below:

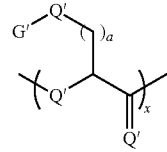

XXVII

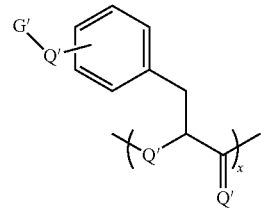

XXVIII

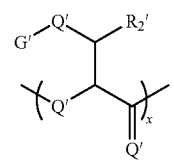

XXIX

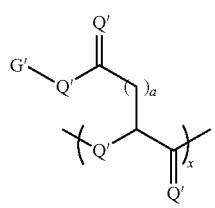

XXX where each Q', G', $R_2'$, x, and terminal group are independently selected as defined herein; and a is selected from an integer of 1-25.

Also provided are compounds of Formula XXXI, XXXII, XXXIII, XXXIV, and XXXV, as shown below:

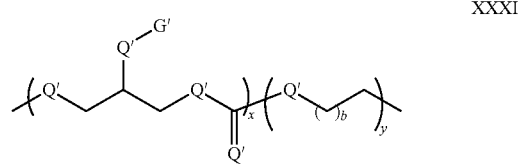

XXXI

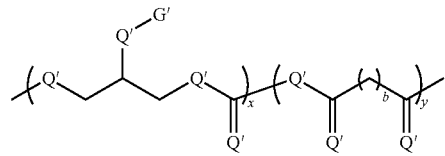

XXXII

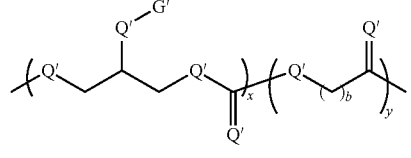

XXXIII

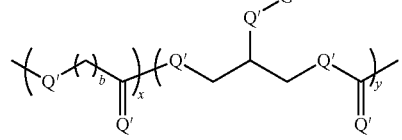

XXXIV

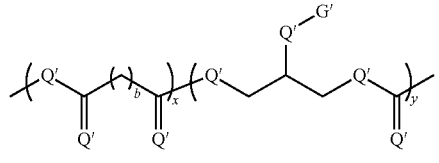

XXXV where each Q', G', x, y, and terminal group are independently selected as defined; and b is selected from an integer of 1-14.

Also provided are compounds of Formula XXXVI and XXXVII, as shown below:

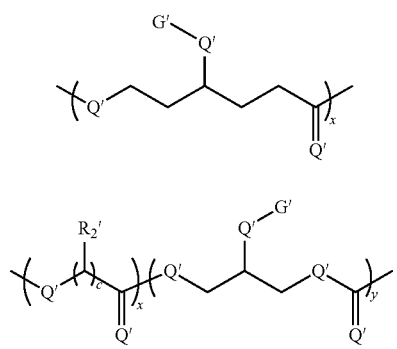

where each Q', G', $R_2'$, x, y, and terminal group are independently selected as defined;

and c is selected from an integer of 1-14.

In certain embodiments, the G' of Formula XXI-XXXVII is selected from among any group shown below:

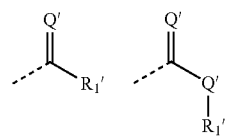

where each Q' and $R_1'$ are independently selected as defined herein.

In certain embodiments, each $R_1'$, $G_1'$, $G_2'$, and G' group of any of Formula XXI-XXXVII is independently selected from among a group shown below:

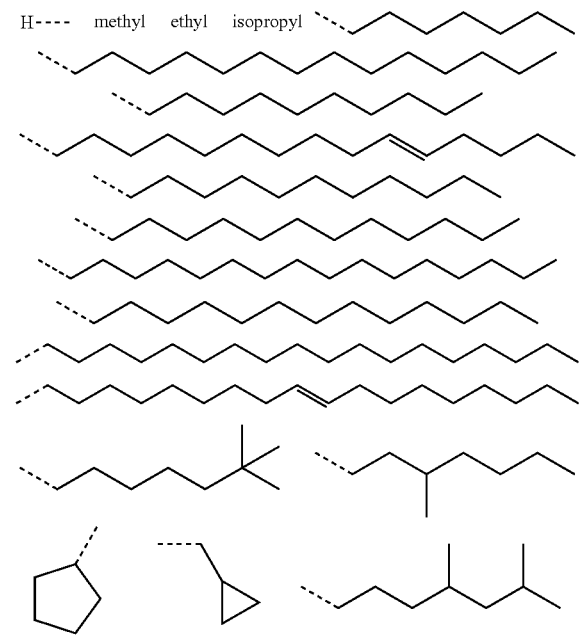

In certain embodiments, each $R_1'$, $G_1'$, $G_2'$, and G' group of any of Formula XXI-XXXVII is independently selected from among a group shown below:

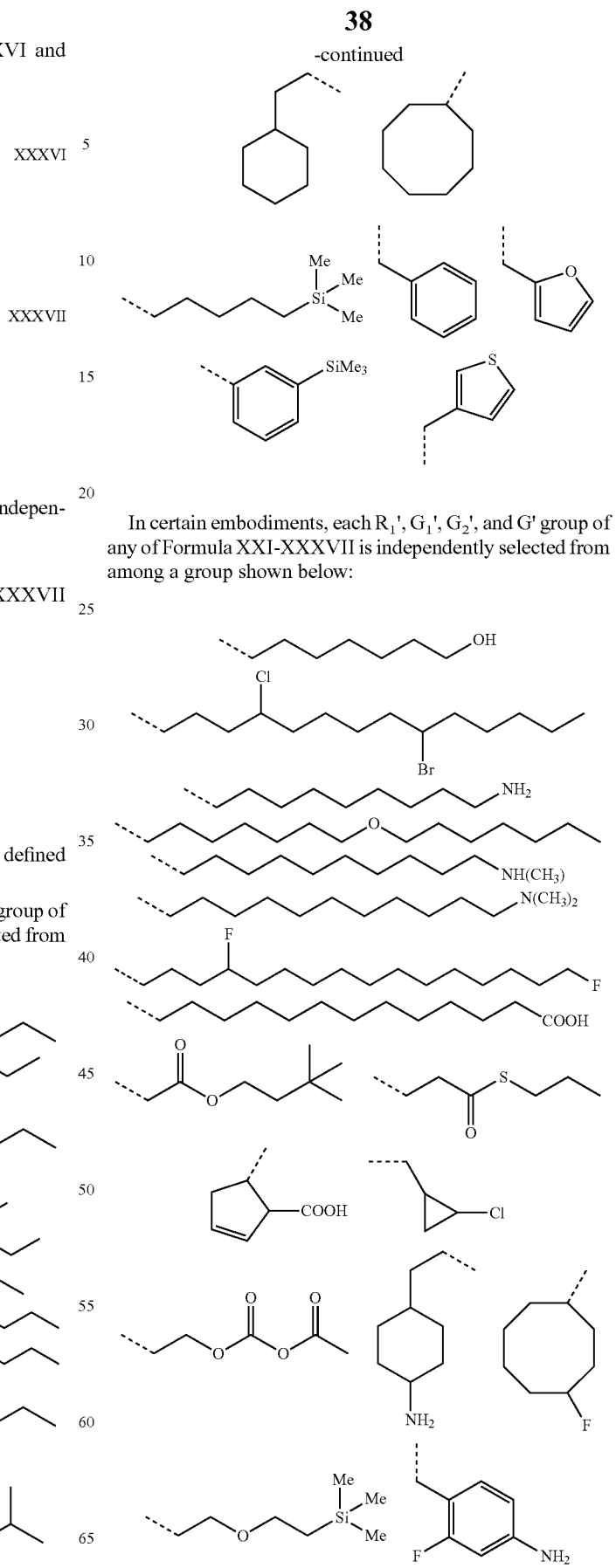

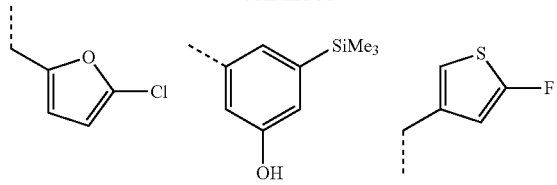

In certain embodiments, each $R_1'$, $G_1'$, $G_2'$, and $G'$ group of any of Formula XXI-XXXVII is independently selected from among a group as shown below:

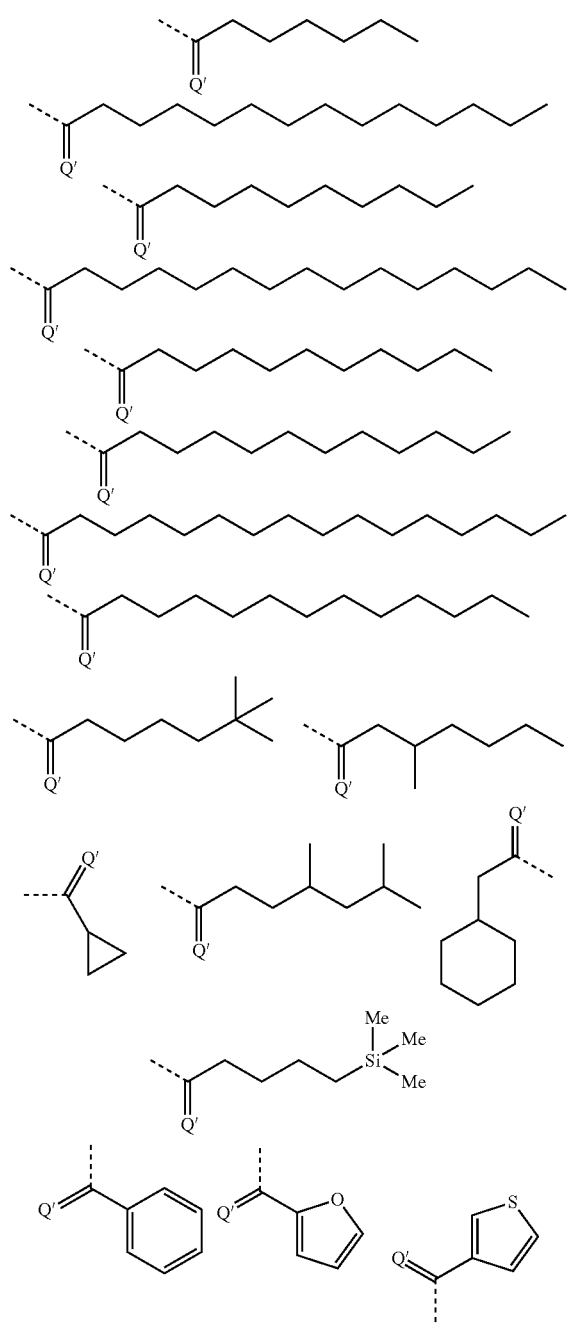

where each $Q'$ is independently selected from among O, S, Se, or NH.

In certain embodiments, each $R_1'$, $G_1'$, $G_2'$, and $G'$ group of any of Formula XXI-XXXVII is independently selected from among a group as shown below:

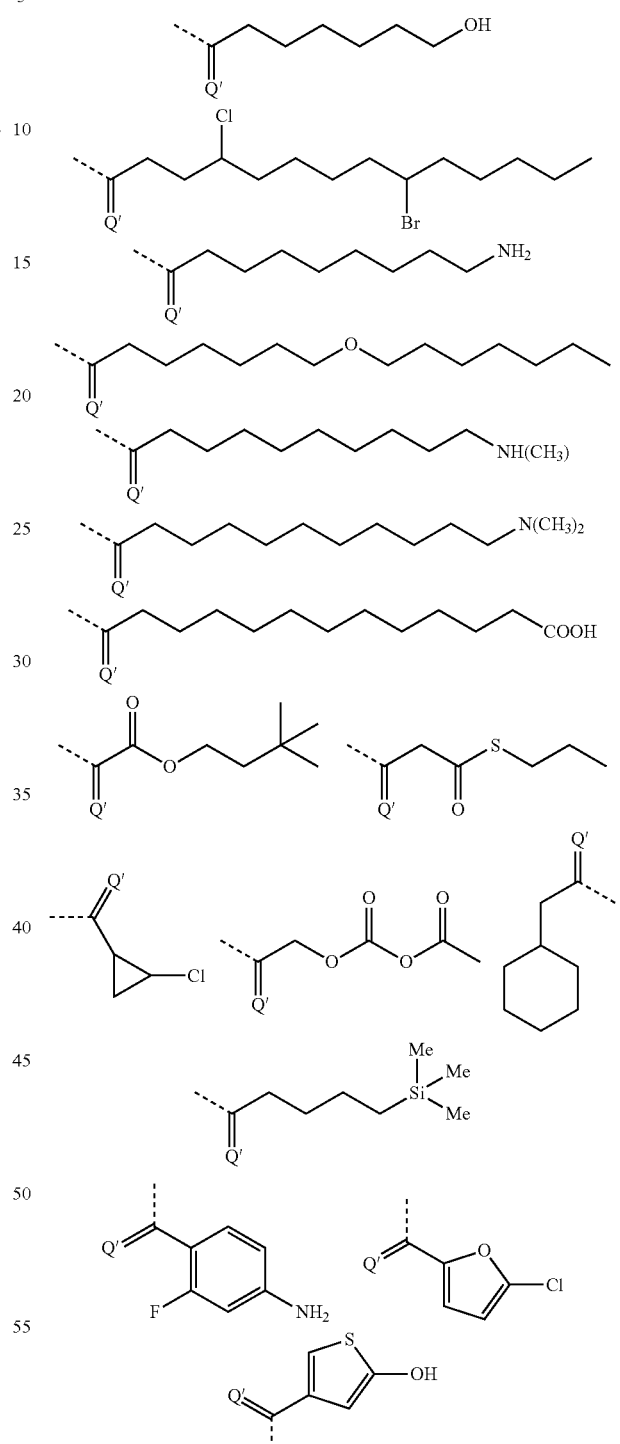

where each $Q'$ is independently selected from among O, S, Se, or NH.

In certain embodiments, each $R_1'$, $G_1'$, $G_2'$, and $G'$ group of any of Formula XXI-XXXVII is independently selected from among a group as shown below:

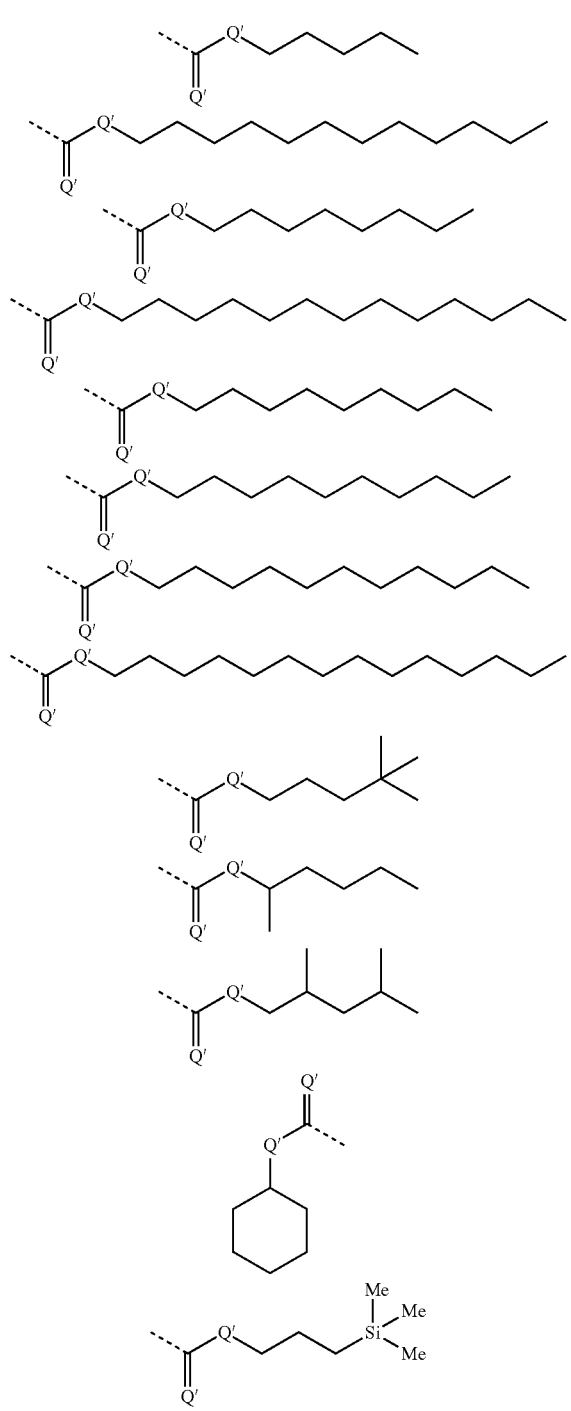

where each Q' is independently selected from among O, S, Se, or NH.

In certain embodiments, each $R_1'$, $G_1'$, $G_2'$, and G' group of any of Formula XXI-XXXVII is independently selected from among a group as shown below:

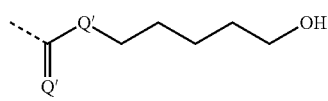

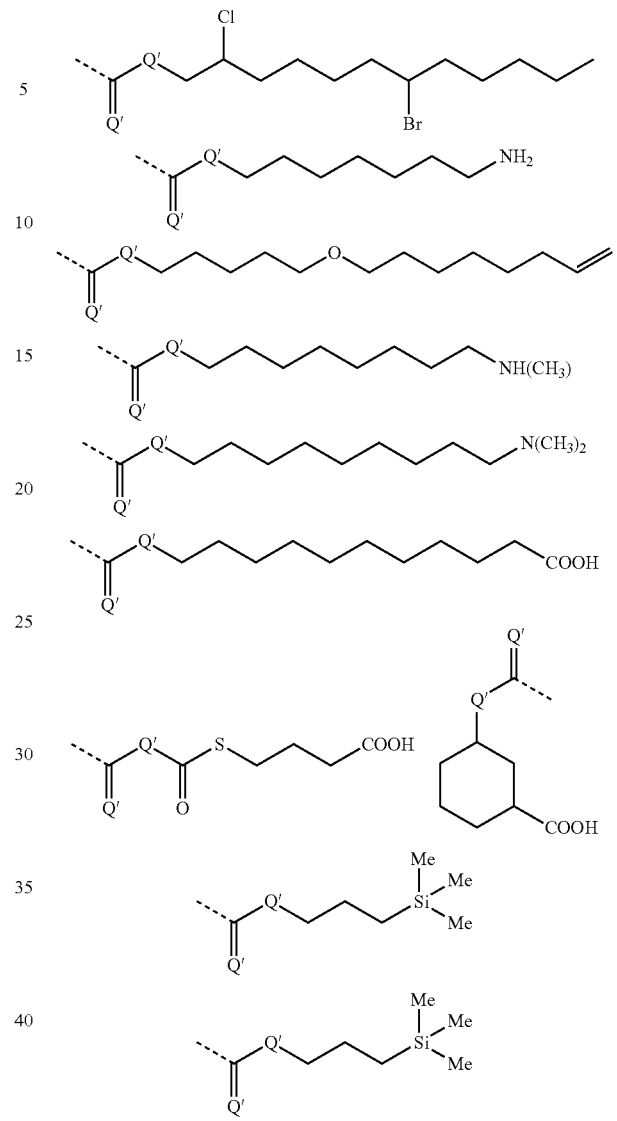

where each Q' is independently selected from among O, S, Se, or NH.

In certain embodiments, each $R_1'$, $G_1'$, $G_2'$, and G' group of any of Formula XXI-XXXVII is independently selected from among a group as shown below:

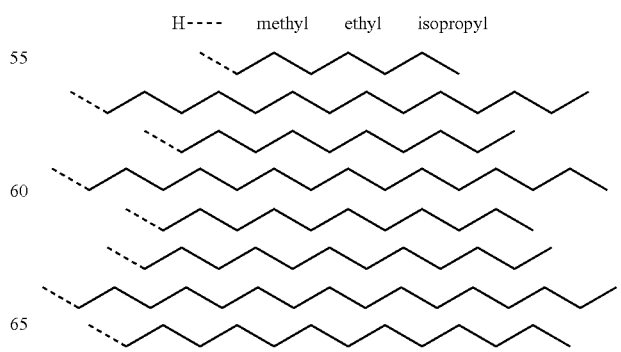

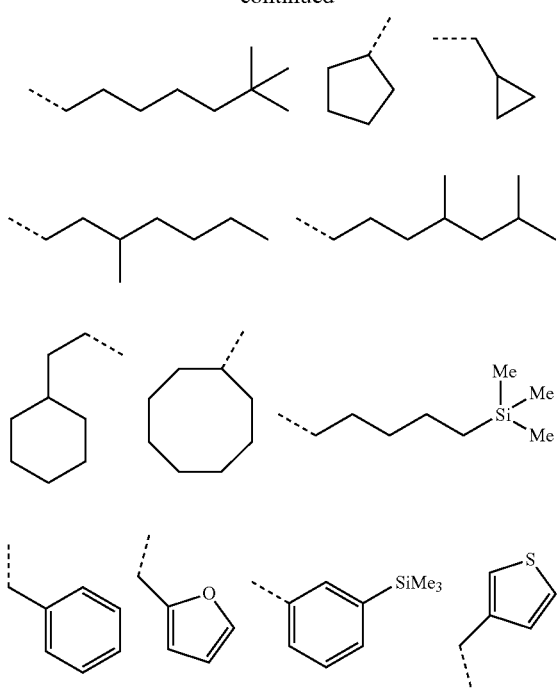

Also provided is compound of Formula XXXVIII, as shown below:

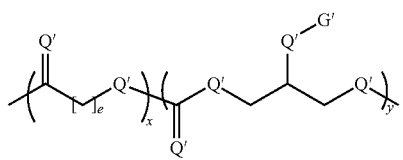
XXXVIII where each Q', G', x, y, and terminal group is independently selected as defined herein; and e is selected from an integer of 2-8.

In various embodiments, the compounds of Formula XXXVIII can be a random copolymer, a block copolymer, alternating copolymer, or a graft copolymer.

In one embodiment, the compound of Formula XXXVIII is a compound of Formula XXXIX, as shown below:

XXXIX where each Q', G', x, y, and terminal group are independently selected as defined herein.

In certain embodiments, the compound of Formula XXXVIII is selected from among a compound of Formula XL, XLI, XLII, or XLIII, as shown below:

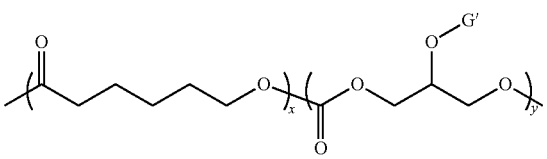
XL

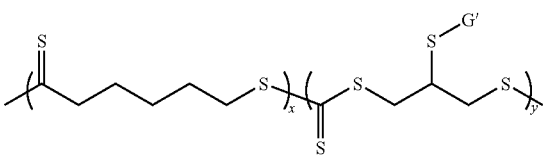
XLI

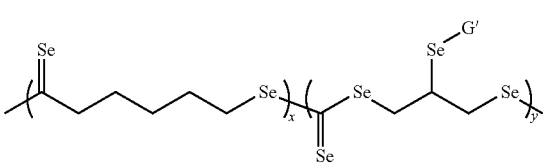
XLII

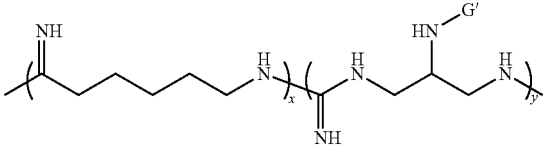
XLIII where each G', x, y, and terminal group are independently selected as defined herein.

In certain embodiments, a compound of Formula XXXVIII is selected from among a compound of Formula XL where Q' is oxygen. In certain embodiments, a compound of Formula XXXVIII is selected from among a compound of Formula XLI where Q' is sulfur. In certain embodiments, a compound of Formula XXXVIII is selected from among a compound of Formula XLII, where Q' is Se. In certain embodiments, a compound of Formula XXXVIII is selected from among a compound of Formula XLIII, where Q' is NH.

In certain embodiments, the compound of Formula XXXVIII is selected from among a compound of Formula XLIV, XLV, or XLVI, as shown below:

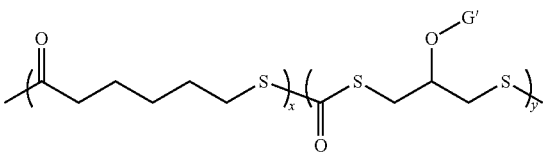
XLIV

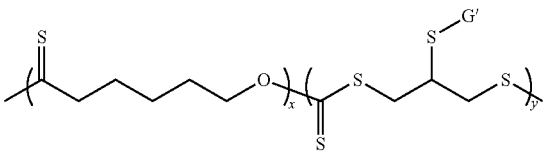
XLV

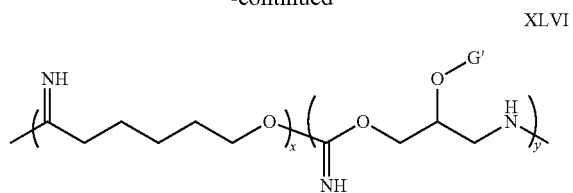

where each G', x, y, and terminal group are independently selected as defined herein.

In certain embodiments, a compound of Formula XXXVIII is selected from among a compound of Formula XLIV. In certain embodiments, a compound of Formula XXXVIII is selected from among a compound of Formula XLV. In certain embodiments, a compound of Formula XXXVIII is selected from among a compound of Formula XLVI.

H. Synthesis of Polymers of Formulas XXI-XLVI

Any method of polymerization can be used to produce the polymers of Formulas XXI-XLVI. For example, polymers of Formulas XXI-XLVI can be prepared by step-reaction polymerization, ring-opening polymerization, or by chain-reaction addition polymerization. As shown below, a polymer of Formula XXXVIII can be prepared by ring-opening polymerization of a lactone monomer and a carbonate monomer. The product of this reaction is a polymer of Formula XXXVIII where Q' is O, and G' is benzyl.

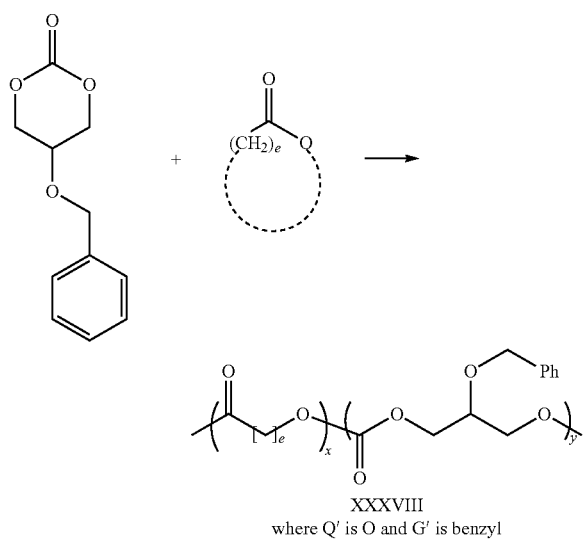

where x, y, e, and terminal group are independently selected as defined herein.

Any method of ring opening polymerization can be used for this reaction. For example, the ring opening polymerization may be induced by heating the reaction. In one embodiment, the reaction is catalyzed by a metal catalyst, such as $Sn(oct)_2$. The reaction can be performed neat, or in the presence of a solvent, such as toluene, dichloromethane, or diethyl ether. Any ratio of monomers can be used. For example, the ratio of carbonate monomer to lactone monomer can be 1:1, 1:2, 1:3, 1:4, 1:5, 1:6, 1:7, 1:8, 1:9, or 1:19.

Any lactone can be used for the polymerization shown above. As shown below, the lactone can be a four, five, six, or seven membered ring:

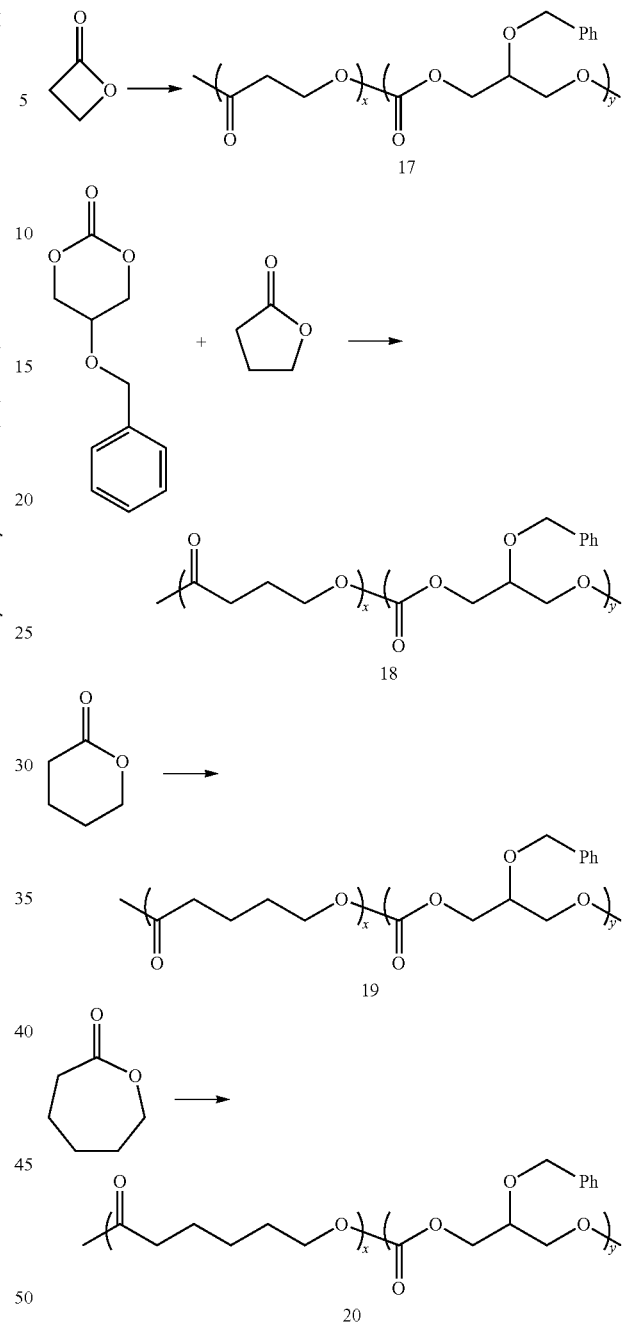

where x, y, e, and terminal group are independently selected as defined herein.

As shown above, Compound 17 is prepared by polymerizing a benzyloxy glycerol carbonate with oxetan-2-one. Compound 18 is prepared by polymerizing a benzyloxy glycerol carbonate with dihydrofuran-2(3H)-one. Compound 19 is prepared by polymerizing a benzyloxy glycerol carbonate with tetrahydro-2H-pyran-2-one. Compound 20 is prepared by polymerizing a benzyloxy glycerol carbonate with oxepan-2-one.

I. Chemical Modifications of Polymers of Formulas XXI-XLVI

Polymers of Formulas XXI-XLVI, wherein G' is a protecting group, can be further modified to contain various side chains and pendant groups. For example, G' can be any protecting group known in the art. In some embodiments, G' is a benzyl ether or benzylidene protecting group. Any method known in the art of adding a side chain or pendant group to a polymer can be used to modify the polymers of Formulas XXI-XLVI. for example, a polymer of Formulas XXI-XLVI can be modified to contain a side group selected from among a straight or branched alkyl, cycloalkyl, aryl, olefin, silyl, alkylsilyl, arylsilyl, alkylaryl, arylalkyl or fluorocarbon chain of 3-50 carbons, wherein the alkyl, cycloalkyl, aryl, olefin, silyl, alkylsilyl, arylsilyl, alkylaryl, arylalkyl or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

Other side chain groups can be selected from among poly(ethylene glycol), poly(ethylene oxide), poly(hydroxyacid), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor. Additionally, a functional side chain can be incorporated into a polymer of any one of Formulas XXI-XLVI, such as a photocrosslinkable or ionically crosslinkable group.

One method of modifying a polymer of Formula XXXVIII is shown below. The benzyl ether can be cleaved to afford a hydroxyl group. Any method of cleaving a benzyl ether known in the art can be used for this transformation. For example, the benzyl ether can be cleaved by catalytic hydrogenation. The resulting hydroxyl group can be reacted with reactants or reagents to produce the polymer of Formula XXXVIII with a non-hydrogen G' group. Any method of reacting an alcohol known in the art can be used for this transformation.

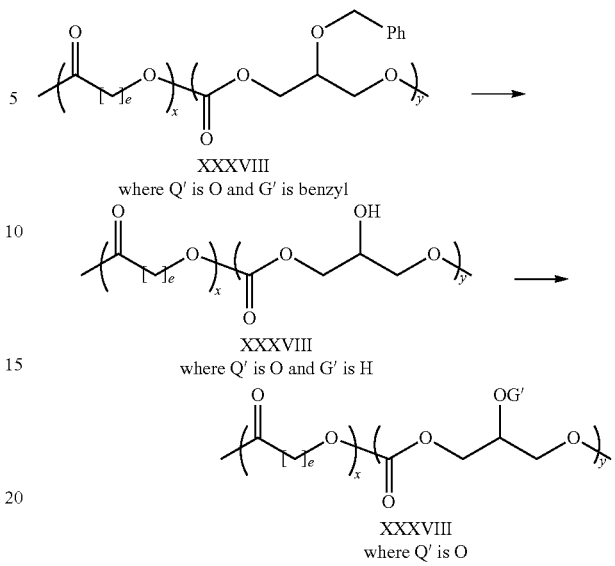

In the compounds shown above x, y, e, and the terminal group are independently selected as defined herein.

As shown below, the polymer of Formula XXXVIII containing a hydroxyl moiety can be modified to yield a polymer with various G' groups. For example, the alcohol can be reacted with a carboxylic acid, such as stearic acid, oleic acid, or myristic acid. In other embodiments, the alcohol is reacted with 6-benzyloxy-hexanoic acid, hexanedioic acid monobenzyl ester, or fmoc-6-amino-hexanoic acid. In various embodiments, the G' group is a carbonate, an ester, or an ether.

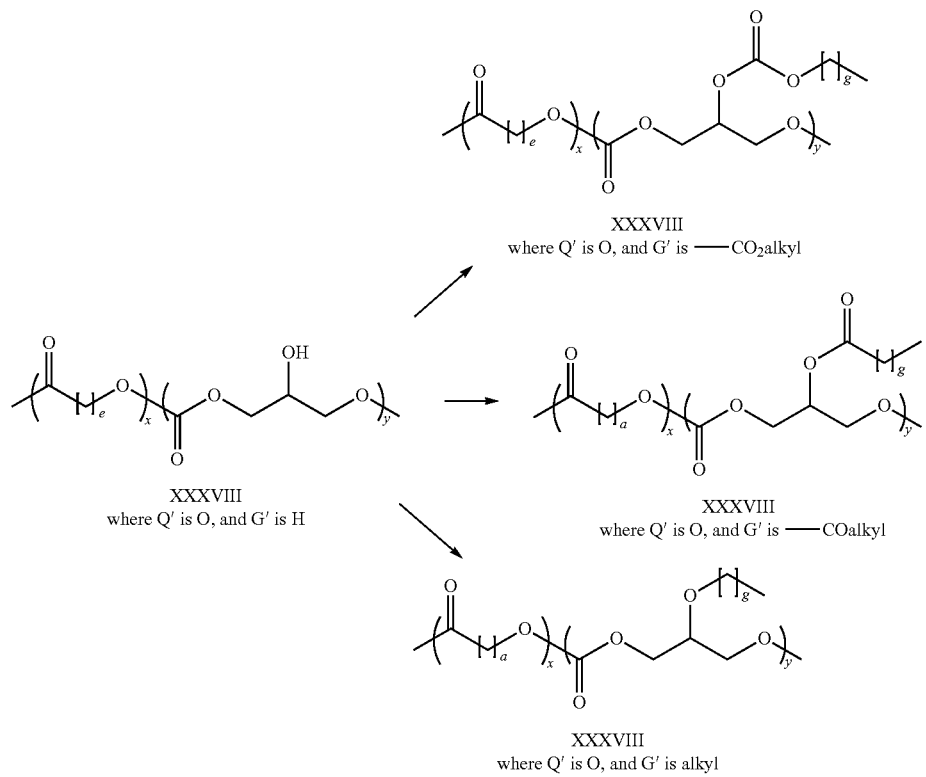

In the compounds shown above x, y, e, and the terminal group are independently selected as defined herein; and g is selected from an integer of 1-25.

As shown below, a polymer containing a hydroxyl moiety can be modified to produce a polymer with various groups. For example, the alcohol can be reacted with a carboxylic acid, such as stearic acid, oleic acid, or myristic acid. In other embodiments, the alcohol is reacted with a benzyloxy-alkyl acid, a alkyl acid monobenzyl ester, or a protected amino-alkyl acid. The benzyloxy, monobenzyl, and fmoc protecting groups can be removed by methods known in the art to produce an alcohol, a carboxylic acid, or an amine, respectively.

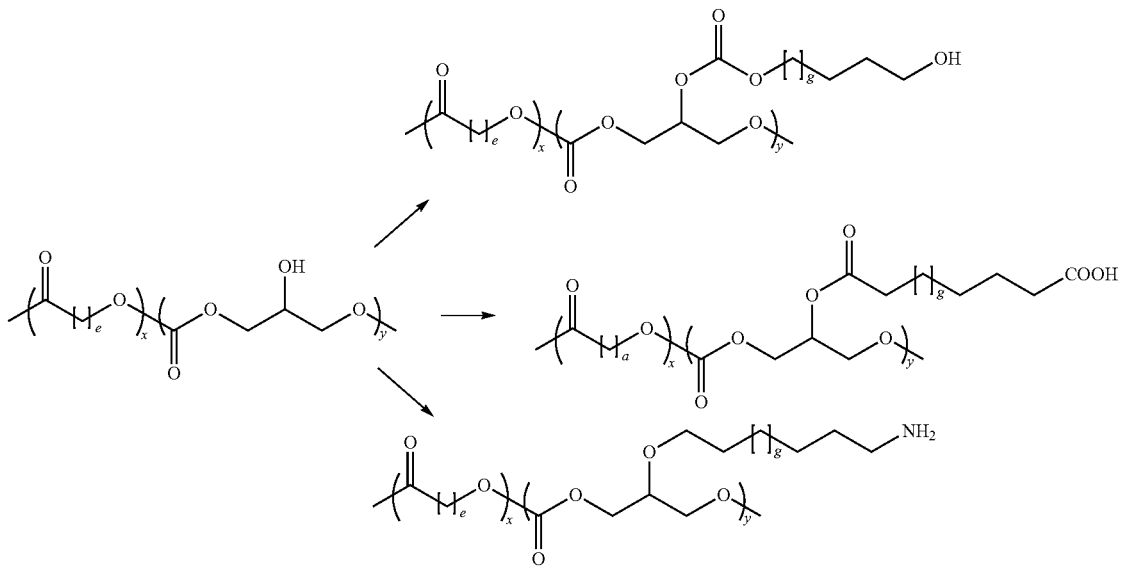

In the compounds shown above x, y, e, g, and the terminal group are independently selected as defined herein.

J. Methods of Forming Particles and Films

Various types of films and particles can be formed from polymers of Formulas XX-XLVI. As shown below, various types of films and particles, such as micro- or nanoparticles, can be made from polymers of Formula XX and XXXVIII. Any of the polymeric films and particles described herein can be made to incorporate bioactive, e.g., therapeutic, agents within the polymer structure to produce a polymer/agent complex. Any method known in the art can be used to form a polymer/agent complex from the monomers and polymers described herein.

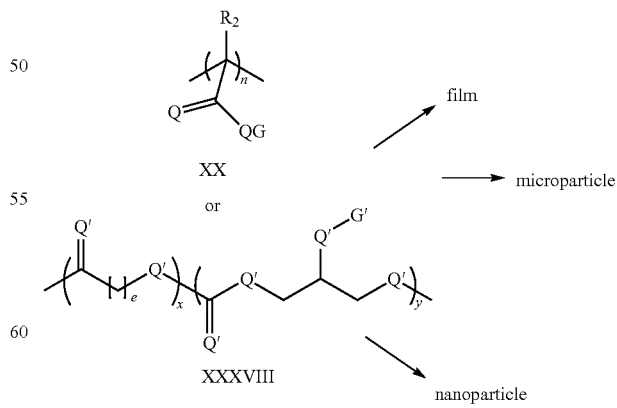

In the compounds shown above, each Q, Q', G, G', n, $R_2$, x, y, e, and terminal group are independently selected as defined herein.

Methods of Making Films

The polymers described herein can be used to produce films using techniques known in the art. For example, as shown above, a polymer of Formula XX or XXXVIII is dissolved in an organic solvent, e.g., dichloromethane, tetrahydrofuran, toluene, or an aqueous solution and deposited onto a solid surface, such as a glass surface. In certain embodiments, the polymer is dissolved in a solvent along with an agent, such as 10-hydroxycamptothecin, and deposited onto a solid surface, such as a glass surface. The solvent is then allowed to evaporate to afford a polymeric film either at ambient temperature or pressure, or at elevated or reduced temperatures and/or pressures. In certain embodiments, the polymer solution is deposited onto the solid surface using a syringe, e.g., a microsyringe. In other embodiments, the polymer solution is deposited onto the solid surface, e.g., glass, mica, polymer, collagen, pericardium, TEFLON®, metal, metal alloy, ceramic or an oxide, using a spraying device, such as an aerosol device. For example, films containing a polymer of Formula XX or XXXVIII can be formed by dissolving the polymer in an organic or aqueous solution, or a mixture of organic and aqueous solutions, and applying the solution to a surface.

In other embodiments, films containing a polymer of Formula XX or XXXVIII are formed by melting the polymer. The melted polymer can be applied to a solid surface, such as glass. In other embodiments, the polymer is applied to a solid surface and is then melted to form a polymeric film.

In certain embodiments, multi-layered films are prepared. For example, a polymer is deposited onto a solid surface as described above to produce a film A second polymeric solution is then deposited onto the first film. Polymer films of 1, 2, 3, 4, 5, and 6, or more layers can be produced by this method. In other embodiments, each polymer film is produced from a polymer of Formula XX or XXXVIII. In another embodiment, 1, 2, or 3 of the layers include a polymer of Formula XX or XXXVIII, and either 1, 2, or 3 other layers include a different polymer, such as poly(lactic acid), poly(glycolic acid), poly(lactic-co-glycolic acid), polycaprolactone, poly(trimethylene carbonate), polyester, polycarbonate, or polyamide.

The various layers or fillers can be selected to dissolve or biodegrade at different rates to produce devices in which different agents are included in different layers and are released at different rates. For example, a first agent can be included in a first surface layer designed to provide a rapid release, e.g., within a few hours or days, and a second agent can be included in a second layer designed to provide an extended release profile, e.g., 1 week, 2, 3, 4, 5 weeks, or even more. Alternatively, an other surface layer can be designed not to release any agent, but to mearly delay release of agents in subsequent layers.

In certain embodiments, a patterned polymer film is prepared by using a microprinter or a microsyringe. For example, a microprinter or microsyringe can be used to deposit a solution containing a polymer of Formula XX or XXXVIII onto a solid surface, such as a glass surface. The microprinter or microsyringe deposits the solution in a controlled manner to form patterns such as stripes and/or dots. The solvent is removed by evaporation. This method can be performed with more than one polymer simultaneously. A solution containing a polymer of Formula XX or XXXVIII and an agent, such as 10-hydroxycamptothecin, may be deposited onto a solid surface by this technique to afford a patterned agent containing film. Such patterned films can deliver agents to specific biological areas and tissues, as determined by the specific pattern of agent loaded within a film.

Methods of Making Particles

The polymers described herein can be used to produce micro- or nanoparticles using methods known in the art. For example, a water in oil emulsion technique is described by Edlund and co-workers (see Edlund et al., Adv. Polymer Sci., 157:67-112, 2001; and Wang et al., Chem. Pharm. Bull., (Tokyo) 44:1935, 1996). Briefly, a polymer is dissolved in dichloromethane using a vortexing device. In certain embodiments, the polymer is dissolved in dichloromethane along with an agent, such as paclitaxel. The solution is placed in a 5% polyvinyl alcohol surfactant and vortexed (or sonicated using a probe tip sonicator) and stirred for 16 hours to produce microparticles. The microparticles are collected and washed with distilled/deionized water and lyophilized.

To produce nanoparticles, one can for example, use a miniemulsion polymerization method (see, e.g., Landfester et al., Macromolecules, 32:5222-8, 1999). Briefly, a monomer as described herein and a free-radical initiator (such as $Cl_2$, 2,2'-azobis(2-methylpropionitrile) (AIBN), or di-t-butylperoxide) are dissolved in a solvent, such as hexane, benzene, toluene, diethyl ether, chloroform, ethyl acetate, dichloromethane, 1,4-dioxane, tetrahydrofuran (THF), acetone, acetonitrile (MeCN), dimethylformamide (DMF), or dimethyl sulfoxide. In certain embodiments, an agent, such as paclitaxel is also dissolved in the solvent. The solvent is removed via rotary evaporation until a viscous mixture remains. The viscous mixture is mixed with a stabilizing surfactant, such as a solution of sodium dodecyl sulfate, in a buffer solution. This mixture is sonicated for 1 hour (1 second pulses with a 2 second delay) with 30 W of power, which forms the miniemulsion and allows the solvent to evaporate. The miniemulsion is transferred into a temperature-controlled oil bath and stirred at 65° C. for 2 hours to initiate the free-radical polymerization. Optionally, the resulting polymeric nanospheres are dialyzed, e.g., against 5 mM pH 8 phosphate buffer, acetate buffer, bicarbonate buffer, or sodium citrate buffer, e.g., over two days, to remove excess surfactant and salts.

Alternatively, nanoparticles can be produced by photoinitiation. For example, a monomer as described herein can be dissolved in a solvent, such as hexane, benzene, toluene, diethyl ether, chloroform, ethyl acetate, dichloromethane, 1,4-dioxane, tetrahydrofuran (THF), acetone, acetonitrile (MeCN), dimethylformamide (DMF), or dimethyl sulfoxide. In certain embodiments, an agent, such as paclitaxel is also dissolved in the solvent. The solvent is removed via rotary evaporation until a viscous mixture remains. The viscous mixture is mixed with a stabilizing surfactant solution, such as sodium dodecyl sulfate, in a buffer solution. The mixture is then sonicated for 30 minutes (1 second pulses with a 2 second delay) with 30 W of power, forming the miniemulsion and allowing the solvent to partially evaporate. Eosin Y and 1-vinyl-2-pyrrolidone are added to the emulsion. The mixture is then exposed to light from a source such as a mercury arc lamp while the solution is stirred vigorously. The resulting particles are stirred overnight while open to the air to allow any remaining solvent to evaporate. Optionally, the polymeric nanoparticles are then dialyzed against a buffer solution to remove excess surfactant and salts.

Polymeric particles can also be prepared by a precipitation method. For example, a polymer of Formula XXXVIII is dissolved in a solvent, such as dichloromethane, along with an agent, such as paclitaxel. The solution is added to an aqueous surfactant solution, such as sodium dodecyl sulfate in water. The resulting mixture is sonicated to produce an emulsion. The mixture is stirred while open to the atmosphere to evaporate the excess solvent, such as dichloromethane. The resulting particles are collected and optionally dialyzed using a membrane with a molecular weight cutoff to remove excess surfactant.

In some embodiments, the diameter of the particles formed is between 1 nm and 50 microns, e.g., between 10 nm and 1 micron, between 50 nm and 1 micron, between 100 nm and 500 nm, or between 1 and 50 microns.

Encapsulation of an Agent within Polymeric Particles

Any method known in the art for encapsulating an agent within a polymeric particle can be used to form a polymer/agent complex. For example, an oil emulsion technique is used to form paclitaxel containing particles of Formula XX. A polymer of Formula XX can be dissolved in a solvent, such as dichloromethane, in the presence of an agent, such as paclitaxel. The polymer/paclitaxel solution is vortexed. A surfactant solution, such as 5% polyvinyl alcohol, is added to the polymer/paclitaxel solution, and the resulting solution is vortexed for about 15 minutes followed by stirring for about 16 hours. The resulting particles are collected, washed with water, and lyophilized. In certain embodiments, the encapsulation efficiency of paclitaxel by the particles using this technique is between 30-99%. In another embodiment, the encapsulation efficiency of paclitaxel by the particles using this technique is between 60-75%.

Agents that Can be Incorporated into Polymeric Films and Particles

Any agent can be incorporated within the polymer films and particles described herein. For example, a polymer film or particle described herein can incorporate a pharmaceutical agent selected from among (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) $H_1$-blocker antihistamines, such as clemastine and terfenadine; (5) $H_2$-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous beta-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alpha, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alpha, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) alpha-blocker sympatholytics, such as prazosin; (34) beta-blocker sympatholytics, such as atenolol; (35) adrenergic agonist sympathomimetics, such as albuterol and dobutamine; (36) cardiovascular agents, such as aspirin (ASA), plavix (Clopidogrel bisulfate) etc; (37) beta-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I anti-arrhythmics, such as lidocaine, mexiletine, phenyloin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) alpha-blocker antihypertensives, such as prazosin; (46) angiotensin-converting enzyme inhibitor (ACE inhibitor) antihypertensives, such as captopril and enalapril; (47) beta blocker antihypertensives, such as atenolol, metoprolol, nadolol, and propranolol; (48) calcium-channel blocker antihypertensive agents, such as diltiazem and nifedipine; (49) central-acting adrenergic antihypertensives, such as clonidine and methyldopa; (50) diuretic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as aminone, dobutamine, and dopamine; (56) cardiac glycoside inotropes, such as digoxin; (57) thrombolytic agents or enzymes, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical antiinfectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) immunosupressive agents, such as cyclosporine, steroids, methotrexate tacrolimus, sirolimus, rapamycin; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$-blocker anti-ulcer agents, such as cimetidine, famotidine, nizatidine, and ranitidine; (74) digestants, such as pancrelipase; (75) prokinetic, such as erythromycin; (76) opiate agonist intravenous anesthetics such as fentanyl; (77) hematopoietic antianemia agents, such as erythropoietin, filgrastim (G-CSF), and sargramostim (GM-CSF); (78) coagulation agents, such as antihemophilic factors 1-10 (AHF 1-10); (79) anticoagulants, such as warfarin, heparin, and argatroban; (80) growth receptor inhibitors, such as erlotinib and gefetinib; (82) abortifacients, such as methotrexate;

(83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadatropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenyloin, and valproic acid; (103) barbiturate anticonvulsants, such as phenobarbital and primidone; (104) benzodiazepine anticonvulsants, such as clonazepam, diazepam, and lorazepam; (105) anti-parkisonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) beta-blocker anti-glaucoma agents, such as timolol; (110) miotic anti-glaucoma agents, such as pilocarpine; (111) ophthalmic aminoglycoside antiinfectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfuram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; (129) vitamin D compounds, such as calcitriol; (130) vitamin A, vitamin E, and vitamin E compounds; (131) poisons, such as racin; (132) anti-bleeding agents, such as protamine; (133) antihelminth anti-infectives, such as metronidazole; and (134) sclerosants such as talc, alcohol, and doxycyclin.

In addition to the foregoing, the following less common drugs can also be used: chlorhexidine; estradiol cypionate in oil; estradiol valerate in oil; flurbiprofen; flurbiprofen sodium; ivermectin; levodopa; nafarelin; and somatropin. Further, the following drugs can also be used: recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); and topotecan. Further still, the following intravenous products can be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alpha; etoposide (VP-16); fluorouracil (5-FU); ganciclovir sodium; gentamicin sulfate; interferon alpha; leuprolide acetate; meperidine HCl; methadone HCl; methotrexate sodium; paclitaxel; ranitidine HCl; vinblastin sulfate; and zidovudine (AZT).

Further specific examples of useful pharmaceutical agents from the above categories include: (a) anti-neoplastics such as androgen inhibitors, antimetabolites, cytotoxic agents, receptor inhibitors, and immunomodulators; (b) anti-tussives such as dextromethorphan, dextromethorphan hydrobromide, noscapine, carbetapentane citrate, and chlorphedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines, and other bioactive peptidic compounds, such as interleukins 1-18 including mutants and analogues, RNase, DNase, luteinizing hormone releasing hormone (LHRH) and analogues, gonadotropin releasing hormone (GnRH), transforming growth factor-β. (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-alpha-1, gamma-globulin, superoxide dismutase (SOD), complement factors, hGH, tPA, calcitonin, ANF, EPO and insulin; (n) anti-infective agents such as antifungals, antivirals, antihelminths, antiseptics and antibiotics; and (m) oxygen, hemoglobin, nitric or sliver oxide.

Non-limiting examples of broad categories of useful pharmaceutical agents include the following therapeutic categories: anabolic agents, anesthetic agents, antacids, anti-asthmatic agents, anticholesterolemic and anti-lipid agents, anticoagulants, anti-convulsants, anti-diarrheals, antiemetics, anti-infective agents, anti-inflammatory agents, anti-manic agents, anti-nauseants, antineoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and prodrugs. Examples of specific drugs that can be used include: asparaginase, bleomycin, busulfan, capecitabine, carboplatin, carmustine, chlorambucil, cisplatin, cyclophosphamide, cytarabine, dacarbizine, dactinomycin, daunorubicin, dexrazoxane, docetaxel, doxorubicin, etoposide, floxuridine, fludarabine, fluoruracil, gemcitabine, hydroxyurea, idarubicin, ifosfamide, irinotecan, lomustine, mechlorethamine, melphalan, mercaptopurine, methotrexate, mitomycin, mitotane, mitoxantrone, paclitaxel, pentostatin, plicamycin, premextred procarbazine, rituximabe, streptozocin, teniposid, thioguanine, thiotepa, vinplastine, vinchristine, and vinorelbine. The currently preferred drugs for lung cancer treatment is paclitaxel, pemetrexed, 10-hydrocamptothecin, irinotecan, erlotinibil/gefetinib or derivates of these molecules.

Examples of anticancer, antineoplastic agents are camptothecins. These drugs are antineoplastic by virtue of their ability to inhibit topoisomerase I. Camptothecin is a plant alkaloid isolated from trees indigenous to China and analogs thereof such as 9-aminocamptothecin, 9-nitrocamptothecin, 10-hydroxycamptothecin, 10,11-methylenedioxycamptothecin, 9-nitro-10,11-methylenehydroxycamptothecin, 9-chloro-10,11-methylenehydroxycamptothecin, 9-amino-10,11-methylenehydroxycamptothecin, 7-ethyl-10-hydroxycamptothecin (SN-38), topotecan, DX-8951, Lurtotecan (GII147221C), and other analogs (collectively referred to herein as camptothecin drugs) are presently under study worldwide in research laboratories for treatment of colon, breast, and other cancers.

Additionally, the pharmaceutical agent can be a radiosensitizer, such as metoclopramide, sensamide or neusensamide (manufactured by Oxigene); profiromycin (made by Vion); RSR13 (made by Allos); THYMITAQ® (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); L1X (made by Terrapin); agents that minimize hypoxia, and the like.

The agent can be selected from a biologically active substance. The biologically active substance can be selected from the group consisting of peptides, poly-peptides, proteins, amino acids, polysaccharides, growth factors, hormones, anti-angiogenesis factors, interferons or cytokines, elements, and pro-drugs. In useful embodiments, the biologically active substance is a therapeutic drug or pro-drug, most preferably a drug selected from the group consisting of chemotherapeutic agents and other antineoplastics such as paclitaxel, antibiotics, anti-virals, antifungals, anesthetics, antihelminths, anti-inflammatories, and anticoagulants. In certain useful embodiments, the therapeutic drug or pro-drug is selected from the group consisting of chemotherapeutic agents and other antineoplastics such as paclitaxel, carboplatin and cisplatin; nitrosourea alkylating antineoplastic agents, such as carmustine (BCNU); fluorouracil (5-FU) and gemcitabine; hormonal antineoplastics, such as goserelin, leuprolide, and tamoxifen; receptor inhibitors such as erlotinib, gefetinib, sutent or anti-ckit inhibitors, such as GLEEVEC®; natural antineoplastics, such as aldesleukin, interleukin-2, docetaxel, etoposide (VP-16), interferon alpha, paclitaxel, and tretinoin (ATRA).

In another embodiment, the biologically active substance is a nucleic acid sequence. The nucleic acid sequence can be selected from among any DNA or RNA sequence. In certain embodiments, the biologically active substance is a DNA sequence that encodes a genetic marker selected from among luciferase gene, β-galactosidase gene, resistance, neomycin resistance, and chloramphenicol acetyl transferase. In certain embodiments, the biologically active substance is a DNA sequence that encodes a lectin, a mannose receptor, a sialoadhesin, or a retroviral transactivating factor. In certain embodiments, the biologically active substance is a DNA sequence that encodes a RNA selected from the group consisting of a sense RNA, an antisense RNA, siRNA and a ribozyme.

Biologically active agents amenable for use with the new polymers described herein include, without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Useful active agents amenable for use in the new compositions include growth factors, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are preferred. Members of the TGF supergene family include the beta-transforming growth factors (for example, TGF-b1, TGF-b2, and TGF-b3); bone morphogenetic proteins (for example, BMP-1, BMP-2, BMP-3, BMP-4, BMP-5, BMP-6, BMP-7, BMP-8, and BMP-9); heparin-binding growth factors (for example, fibroblast growth factor (FGF), epidermal growth factor (EGF), platelet-derived growth factor (PDGF), and insulin-like growth factor (IGF)); inhibins (for example, Inhibin A, Inhibin B); growth differentiating factors (for example, GDF-1); and activins (for example, Activin A, Activin B, and Activin AB).

K. Applications for Polymer/Agent Compositions

The polymers provided herein can be utilized to promote healing or treat or inhibit disease by targeting drug delivery to local and regional areas. The polymers provided herein can also be used for a variety of applications including, but not limited to, production of micro- and nanoparticles, films, tissue scaffolding, coatings, sutures, and orthopedic materials. The polymers can also be used in various cosmetic applications, such as tissue augmentation. Such materials can be used to repair an injured tissue, organ, bone, or genetic defect. Other uses of the polymers provided herein include treatment of early, late, or previously treated malignancies or to inhibit recurrence of cancers that have been surgically removed or locally treated, avoidance of locoregional lymph node metastasis, augmentation of local wound healing and decrease in infection, manipulation of structure and abnormal scar formation, and for the treatment of post-operative pain.

In some embodiments, the polymers provided herein are used to treat cancer. For example, the polymers provided herein can be used to treat lung, colon, prostate, pancreas, or breast cancer. They could also be used with bone marrow transplantation to target residual tumor cells in the graft, such as lymphomas and leukemias. The polymeric particles can be injected or infused into or around inoperable tumors to locally deliver drugs, such as chemotherapy or sensitizers, or injected or infused near the site of the operation incision to deliver agents such as antibiotics, anesthetics, or growth or healing factors, thereby avoiding side effects associated with systemic delivery. The polymeric particles provided herein can be administered at a site of surgery with the intent of the particles being carried by the lymph fluid to locoregional nodes. The particles can become trapped at the lymph nodes, allowing delivery of agents to tumor cells that also commonly migrate to lymph nodes. Cells that commonly migrate to lymph nodes include tumor cells and immune cells such as T cells or dendritic cells, and thus direct presentation of antigen by the particles can be utilized to enhance the immune system. Thus, the particles can be used to treat tumors systemically either by targeting the tumor cells directly or by upregulating the immune system to fight the tumor.

The polymeric particles and films provided herein can also be administered to sites where tumor regrowth is likely to occur. The particles and films can be administered to areas where, as a consequence of disease, such as COPD or inflammatory bowl disease, or systemic chemotherapy, poor healing will result in major complications. In addition, the particles and films can be administered to the margins of a surgical excision or resection, or to sites following local ablative therapy. For such applications, the polymeric particles are prepared to adhere to the surgical margin or be retained within the confines and perimeter of the mass. In other embodiments, the particles or films adhere to the pericardium, cartilage, or collagen for the delivery of anti-cancer or antineoplastic agents. In other embodiments, the films can be stapled, sutured, and/or glued in place at a site.

In other embodiments, the films and particles described herein can be used in cosmetic applications. In such an application, the swelling associated with pH changes can be advantageously utilized. For example, many of the acrylate polymers described herein upon delivery to a tissue site swell and increase in size and bulk, filling voids. Such polymers can be used without any agents to fill wrinkles or to increase the size of tissue, e.g., in the lips or cheeks. Optionally, the polymers could deliver cosmetic agents such as BOTOX® and/or analgesics. The net result of such a treatment could be, e.g., a smoothing of facial tissue. In some embodiments, the polymers used for such an application are, e.g., 2a-6a and 9a and 10a.

Any method of adhering particles to biological tissue can be used for this application. For example, the polymeric particles provided herein can be coated with Pluronic F127. In another embodiment, the particles are entrapped within a gel, hydrogel, adhesive, sealant or surgical reinforcement strip made from pericardium, TEFLON®, plastic, or other materials or particles that can utilize a specific bound such as biotin-avidin to increase there resident time at the implant site.

In addition, other types of surgery can benefit from the use of the polymeric particles and films described herein. For example, films and particles that contain antibiotics can be utilized for local delivery at a surgical site. The release rate of the antibiotics and/or analgesics can be prolonged to reduce the risk of post-surgical infection, such as *Clostridium difficile* infection. This method provides an alternative to the use and risk of systemic antibiotics. The films and particles can contain anesthetics, such as local amide anesthetics, IV narcotics, or anti-inflammatory agents, such as steroids or NSAIDS, to reduce the discomfort of patients. The use of such polymeric materials can reduce morbidity secondary to delirium and constipation, decrease the length of hospital stays for patients, and reduce overall health care costs.

In certain embodiments, the polymeric films and particles are in contact with aqueous or organic solutions, or combinations thereof. The aqueous solutions can be selected from among water, buffered aqueous media, saline, buffered saline, solutions of amino acids, solutions of sugars, solutions of vitamins, solutions of carbohydrates or combinations of any two or more thereof. The organic solutions can be selected from among DMSO, ethanol, methanol, THF, dichloromethane, DMF, hexane or toluene or combinations of any two or more thereof.

The polymeric particles and films can contain genetic materials, e.g., nucleic acid sequences. Such materials can be used to transfect cells in vitro, ex vivo, or in vivo. The polymeric particles and films can contain a receptor recognizing a targeting moiety, allowing specific entrance into a cell or activation or inhibition of a cell receptor or subsequent intracellular signaling or apopototic pathway. Thus, the polymeric materials described herein can be used to deliver nucleic acid sequences to a cell or to deliver agents that can be transported to the nucleus of a cell or effect transcription or translation within a cell, such as steroids or specific transcription factors.

The methods of using the polymeric particles and films described herein can be used separately or they can be combined with one or more therapies to treat a single patient. For example, particles containing one type of therapeutic agent can be designed and delivered in a manner that results in the particles becoming entrapped at lymph nodes, whereas other particles or films that contain either the same or a different therapeutic agent can be applied to surgical margins or suture sites. It should also be recognized that other agents besides chemotherapeutic agents, e.g., cytokines, growth factors, and anti-inflammatory agents, can be used in these methods and combinations of particles containing a variety of chemotherapeutic or other agents can be employed to both kill tumor, foster healing, and decrease pain.

The polymeric microparticles, nanoparticles, films, gels, and other polymer forms provided herein can be used for in vitro and in vivo manipulation of drug release kinetics. Depending upon the polymer selected, the rate of drug release can be delayed or immediate. In certain embodiments, the polymers provided herein can be used for prolonged drug delivery after an initial period of quiescence to permit surgical healing to occur. In other embodiments, the polymeric particles provided herein provide a dual mechanism of delivery where a drug is released from the particles and the particles swell to destabilize or destroy the cell or cellular compartment (e.g., endosome). Alternatively, the particles can swell and become lodged, embedded, or otherwise immobilized at a certain target location due to the enlarged size of the particle. For example, swelled particles can become lodged or embedded within a cavity, node, tubule, bronchus, or capillary and can be used to occlude blood flow as an embolization agent for bleeding, arteriovenous malformations, or tumor devascularization or can be used to prevent airflow to a specific portion of the lung as for endoscopic lung volume reduction surgery, to cite only two examples of potential uses of this property. Particle swelling can be triggered by pH change from an exogenous agent added to the polymer, a change within a cavity or vessel as can occur in a ischemic or infected tissue or cavity or within an intracellular compartment such as an endosome. Such particles can also be manufactured to release agents that manipulate healing or fibrosis to facilitate permanent or temporary closure of the occluded lumen or cavity.

Certain embodiments of the invention are directed towards polymeric films that are designed to deliver chemotherapeutic agents locally at surgical sites, with incorporation into the resection margin. These films are used, e.g., in the treatment of cancer patients, where delivering drugs locally has the advantage of avoiding side effects associated with systemic drug delivery. These films allow the delivery of agents at local concentrations that could not otherwise be achieved due to drug toxicity. The films can release agents at the site of surgery and the released agents can diffuse to areas of close proximity to the implantation site and to the site of metastatic tumor growth. The implanted polymeric films can deliver one or more anti-cancer agents, e.g., as described herein, that will act upon cancer or metastatic cells remaining at the surgical margins after tumor excision is performed. Thus, the films can reduce the incidence of tumor recurrence at a resection margin after removal of cancerous tissue.

An advantage of the films provided herein is the ability to cover larger areas uniformly. For example, the polymeric films can cover the chest wall to treat diseases such as mesothelioma or in other body cavities for diseases such as sarcomas. In addition, the polymeric films can incorporate local anesthetics or IV narcotics and be applied along an entire surgical incision for peri-operative analgesia, or incorporate growth factors, anti-inflammatory agents in order to manipulate wound healing and prevent hypertrophic scar or stricture formation.

Polymeric films containing a single or multiple agents can be applied to a solid surface in a controlled manner to form patterns such as stripes and dots. Single or multiple agents can be incorporated in any pattern to achieve precise therapeutic delivery of multiple agents simultaneously. More than one type of polymer film can be used to further tune or control the release of the drug. A further embodiment of the invention is the use of multi-layer films to alter the release of the agent(s).

For example, a film composed of a polyester-co-carbonate of 80:20 caproic acid and glycerol-stearic acid can be loaded with a drug, such as taxol, camptothecin, or pemetrexed. The film can then be coated with another polymer of the same or different composition that does not contain the drug, forming a multi-layered film. The top polymer layer, which does not have the drug, acts as a sacrificial layer that first inhibits the release of the drug from the underlying film, but as the top layer degrades, the bottom layer starts to release the drug. In this fashion, delayed and controlled release can occur and can be utilized to allow initial wound healing to occur before delivery of chemotherapy which can inhibit wound healing, as one example. Alternatively, different drugs can be released sequentially and either enhance or prolong the effect of the other drug or protect "normal" cells from the toxic effects of the second drug or to rescue cells from the effects of a second agent, for example pre-treatment with folate can limit toxicity of normal cells to anti-folate chemotherapies and yet tumor cells remain susceptible.

The polymers provided herein can be used to deliver any agent. The agent can be in any pharmaceutically acceptable form, including pharmaceutically acceptable salts. A large number of pharmaceutical agents are known in the art and are amenable for use in the pharmaceutical compositions of the polymeric materials described herein. Acceptable agents are described elsewhere herein, and include, but are not limited to, chemotherapeutic agents, such as radiosensitizers, receptor inhibitors and agonists or other anti-neoplastic agent; immune modulators and bioactive agents, such as cytokines, growth factors or steroids with or without the co-incorporation of tumor or pathogen antigens to increase the anti-neoplastic response as a means of vaccine development; local anesthetic agents; antibiotics; or nucleic acids as a means of local gene therapy.

The biologically active substances and agents are used in amounts that are therapeutically effective. While the effective amount of a biologically active substance will depend on the particular material being used, amounts of the biologically active substance from about 1% to about 65% can be desirable. Lesser amounts can be used to achieve efficacious levels of treatment for certain biologically active substances.

The amount of drug delivered per area of film or per particle will depend on the therapeutic range of the drug, its toxicity when delivered locally, and the clinical characteristics of the patient being treated. The number of particles or amount of film delivered to a site is selected depending on factors such as 1) the amount of agent delivered per particle, 2) the therapeutic range of the agent, 3) the local toxicity of the agent, and 4) the clinical characteristics of the patient being treated. The development of dosages based on these parameters is routinely performed by those skilled in the art of pharmacology and clinical medicine. For example, between $1 \times 10^4$ and $1 \times 10^9$ particles/cm can be administered to a biological area.

The release kinetics of a given polymer film or particle can be fine-tuned and adjusted by varying the ratio of monomer units and/or by modifying the side chains of a given copolymer. In this manner, a family of copolymers with varying release kinetics can be used to accommodate the delivery of several different drugs with differing desired release kinetics. For example, making more side chains along the polymer that are hydrophilic will generally make the polymer more hydrophilic overall and will also generally increase the release rate of an agent from the polymer.

In certain embodiments, the polymeric particles or films delay release of chemotherapeutic agents. The delayed release can coincide with wound healing. In certain embodiments, drug delivery is delayed for a period of approximately 0-6 weeks. In other embodiments, the drug is released over a period of 1-6 weeks. In another embodiment, the drug is released over a period of 2 weeks. In other embodiments, the drug is released for up to 3 months. One method of controlling the rate of release from the particles is by varying the ratio of different monomer units during polymerization. For example, a ratio of 20:80 of glycerol and caproic acid provides polymers and resulting microparticles that release drug over five days.

Provided herein are particles, including microparticles and nanoparticles. In certain embodiments, the size of the polymer particles described herein are between 2 and 100 nm in diameter. In other embodiments, the size of the polymer particles are between 0.02-10 micrometers in diameter. In other embodiments, the size of the polymer particles are between 1-50 micrometers in diameter. Other polymeric particles of a larger size can be useful at specific sites, such as where tumor regrowth is prevalent. For example, polymeric particles of a larger size can be useful at a surgical margin, where suturing or stapling has occurred, or within a naïve or treated tumor such as an ablated cavity secondary to radiofrequency ablation or other therapy, or within a spontaneous cavity such as occurs in squamous cell carcinoma. Placement of polymeric particles within other spontaneous cavities could be utilized to result in sclerosis of the cavity, either with release of specific sclerosing agents such as talc powder, alcohol or doxycyclin as examples or other inflammatory agents. This approach can then be utilized in the treatment of bullous disease in emphysema or infectious diseases such as ecchinococcal cysts, for example.

The new monomers and polymers can also be used to prepare biodegradable oligomers, polymers, macromolecules, and copolymers using standard techniques. The oligomers, polymers, macromolecules and copolymers can contain alkyl side chains formed between [1] a monomer or macromolecular unit containing at least one functional side group; [2] alkyl chains containing 1-50 carbon units; and, in certain embodiments, [3] a structurally different monomer or macromolecular unit. In certain embodiments, the macromolecular materials can be elastic solids or viscoelastic solids. In various embodiments, the macromolecular materials provided herein are hydrophobic or hydrophilic. In other embodiments, a macromolecular material provided herein undergoes a change from hydrophobic to hydrophilic in response to a change in pH. In certain embodiments, the macromolecular materials provided herein swell to a size that destabilizes or destroys a cell or cellular compartment.

EXAMPLES

The invention is further described in the following examples, which do not limit the scope of the invention described in the claims.

Example 1

Synthesis of 5-Methyl-2-(2,4,6-trimethoxyphenyl)-[1,3]-5-dioxan-5-yl-methyl methacrylate

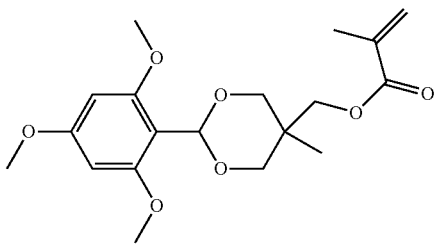

5-Methyl-2-(2,4,6-trimethoxyphenyl)-[1,3]-5-dioxan-5-yl-methanol was prepared according a modification of a previously reported method (Gillies et al., J Am Chem Soc 126: 11936-43, 2004). First, 1,1,1-tris(hydroxymethyl)ethane and 2,4,6-trimethoxybenzaldehyde were dissolved in tetrahydrofuran, and 5 Å molecular sieves were added as a desiccant. A catalytic amount of p-toluenesulfonic acid was then added to the mixture, and the reaction was allowed to proceed at room temperature. When the reaction was complete, triethylamine was added to quench the acid. The molecular sieves were then removed using filtration. The solvent was removed via rotary evaporation under reduced pressure, and the residue dissolved in dichloromethane. This mixture was then washed three times with 100 mM pH 8.0 phosphate buffer and dried over anhydrous sodium sulfate. The solvent was subsequently removed using rotary evaporation under reduced pressure, and the residue was purified using silica gel chromatography.

5-Methyl-2-(2,4,6-trimethoxyphenyl)-[1,3]-5-diox-anyl-methanol and triethylamine were dissolved in dichloromethane and chilled to 0° C. Methacryloyl chloride was then added drop wise to the mixture. After mixing for 16 h, the mixture was then washed three times with 100 mM pH 8.0 phosphate buffer and dried over anhydrous sodium sulfate. The solvent was subsequently removed using rotary evaporation under reduced pressure, and the residue, and the title compound was isolated using silica gel chromatography.

Example 2

Synthesis of 5-Methyl-2-phenyl-[1,3]-5-dioxanylmethanol

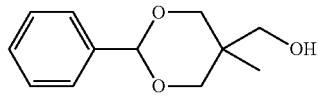

1,1,1-Tris(hydroxymethyl)ethane (2.61 g, 21.7 mmol) and p-toluenesulfonic acid (0.339 g, 1.97 mmol) were dissolved in benzaldehyde (2.8 mL, 2.9 g, 28 mmol) and stirred at 45° C. for 1 h. At this time, toluene (1.0 mL) was added to the solution, and toluene/water was distilled out of the mixture at 95° C. Fresh toluene was added, and distillation was carried out again. This process was repeated until no water was observed in the distillate. Sodium bicarbonate was added to quench the acid, and excess sodium bicarbonate was removed using filtration. The remaining toluene was removed via rotary evaporation, leaving a slightly yellow oil. This mixture was then separated using silica gel chromatography. The product was obtained as a white solid at 41.8% yield.

Example 3

Synthesis of 5-Methyl-2-phenyl-[1,3]-5-dioxanylmethyl Methacrylate

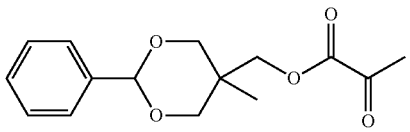

5-Methyl-2-phenyl-[1,3]-5-dioxanylmethanol (0.504 g, 2.42 mmol) and triethylamine (0.68 mL, 0.49 g, 4.8 mmol) were dissolved in dichloromethane and chilled to 0° C. Methacryloyl chloride (0.35 mL, 0.37 g, 3.6 mmol) was then added drop wise to the mixture. After mixing for 16 hours, the mixture was then washed 100 mM pH 8.0 phosphate buffer (50 mL×3) and dried over anhydrous sodium sulfate. The solvent was subsequently removed using rotary evaporation under reduced pressure, and the product was isolated using silica gel chromatography at 83.9% yield.

Example 4

Synthesis of 1,3-bis(benzyloxy)propan-2-yl Methacrylate

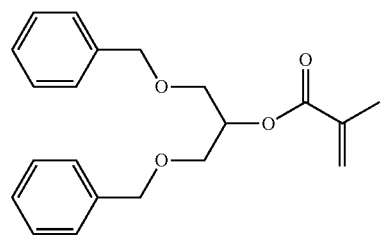

1,3-bis(benzyloxy)propan-2-ol (0.45 mL, 0.50 g, 1.8 mmol) and triethylamine (0.52 mL, 0.37 g, 3.7 mmol) were dissolved in dichloromethane and chilled to 0° C. Methacryloyl chloride (0.27 mL, 0.29 g, 2.8 mmol) was then added drop wise to the mixture. After mixing for 16 h, the mixture was then washed 100 mM pH 8.0 phosphate buffer (50 mL×3) and dried over anhydrous sodium sulfate. The solvent was subsequently removed using rotary evaporation under reduced pressure, and the product was isolated using silica gel chromatography at 81.0% yield.

Example 5

Poly(benzyloxy glycerol carbonate-co-ε-caprolactone)

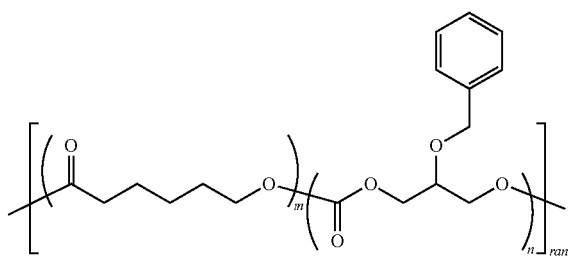

5-(benzyloxymethyl)-1,3-dioxan-2-one (624 mg, 3 mmol) and ε-caprolactone were combined of varying ratios (to a total of 10.0 mmol) in a 10 mL schlenk flask and subsequently evacuated and flushed with $N_2$ three times. Meanwhile, the catalyst $(Sn(oct)_2, 6.5$ μL, 0.02 mmol, monomer/initiator ratio=500) was evacuated in a small flask for 60 minutes. The Schlenk flask was partially submerged in a thermostatted oil bath, preheated to 140° C. Toluene (400 μL) was added to the catalyst and the mixture was injected via syringe to the monomers. The reaction was stirred for 48 hours, removed from heat, and cooled to room temperature. The polymer was dissolved in dichloromethane (10 mL) and precipitated in cold methanol. The solvent was decanted and subsequently dried by evaporation. The resulting polymer formed either a viscous oil or white solid precipitate depending on the carbonate content of the copolymer. Copolymers were formed with the following carbonate mole fractions: 0.05, 0.10, 0.20, 0.30, 0.40, 0.50, 1.00.

Example 6

Poly(hydroxy glycerol carbonate-co-ε-caprolactone)

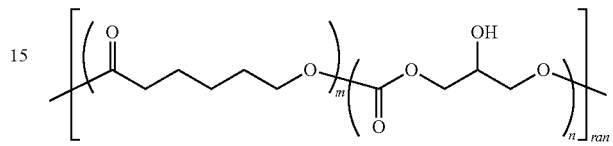

Poly(benzyloxy glycerol carbonate-co-ε-caprolactone) (1.0 g, 2.02 mmol) was dissolved in 50 mL dry dichloromethane inside a Parr bottle. 10% Pd/C (50 mg) and 20% $Pd(OH)_2/C$ (50 mg) were then added to the solution. The reaction mixture was evacuated and purged with hydrogen three times. The flask was then pressurized to 60 psi with hydrogen and shaken for 24 hours. The reaction mixture was filtered through Celite and the filter cake washed with 50 mL dichloromethane. The solvents were then evaporated to yield the final polymer. The resulting polymer formed either a viscous oil or white solid precipitate depending on the carbonate content of the copolymer. Copolymers were formed with the following carbonate mole fractions: 0.05, 0.10, 0.20, 0.30, 0.40, 0.50, 1.00.

Table 1 below indicates the composition, molecular weight, and thermal data of the different copolymers, which are illustrated by structural formulas below the table. In Table 1, CL=caprolactone; CG carbonate of glycerol $f_{cg}$=mole percent carbonate monomer in polymerization feed; $F_{cg}$=mole percent carbonate monomer in copolymer; $M_n$=number average molecular weight; PDI=polydispersity index; $T_g$=glass transition temperature, $T_c$=crystallization temperature; $T_m$=melting temperature; $H_f$=heat of fusion.

TABLE 1

| | | | Molecular Weights | | | Thermal Properties | | | |
|---|---|---|---|---|---|---|---|---|---|
| Polymer | $f_{cg}$ | $F_{cg}$ | $M_n$ (theo.) | $M_n$ (SEC) | $M_w/M_n$ | $T_g$ (° C.) | $T_c$ (° C.) | $T_m$ (° C.) | $\Delta H_f$ (J/g) |
| CL-CG-100-0 | 0 | 0 | 57,000 | 22,700 | 1.47 | −64 | 36 | 57 | 61.5 |
| CL-CG-90-10-Bn | 10 | 11 | 61,700 | 13,300 | 1.67 | −54 | 8 | 40 | 38.5 |
| CL-CG-90-10-OH | 10 | 11 | 57,200 | 12,200 | 1.67 | −59 | 7 | 35 | 32.6 |
| CL-CG-80-20-Bn | 20 | 23 | 66,400 | 10,200 | 1.96 | −49 | −4 | 31 | 25.4 |
| CL-CG-80-20-OH | 20 | 23 | 57,400 | 8,600 | 1.96 | −56 | 0 | 23 | 8.5 |
| CL-CG-80-20-C6-OH | 20 | 23 | 68,800 | 10,100 | 1.91 | −47 | −1 | 43 | 33 |
| CL-CG-80-20-C5-COOH | 20 | 23 | 70,200 | 10,400 | 1.96 | −46 | −5 | 40 | 33 |
| CL-CG-80-20-C6-NH$_2$ | 20 | 23 | 68,700 | 10,100 | 1.94 | −44 | 8 | 44 | 35 |
| CL-CG-70-30-Bn | 30 | 30 | 71,100 | 9,300 | 1.78 | −43 | 3 | 22 | 13.4 |

TABLE 1-continued
| Polymer | $f_{cg}$ | $F_{cg}$ | Molecular Weights | | | Thermal Properties | | | |
| --- | --- | --- | --- | --- | --- | --- | --- | --- | --- |
| | | | $M_n$ (theo.) | $M_n$ (SEC) | $M_w/M_n$ | $T_g$ (°C.) | $T_c$ (°C.) | $T_m$ (°C.) | $\Delta H_f$ (J/g) |
| CL-CG-60-40-Bn | 40 | 42 | 75,800 | 7,900 | 1.94 | −38 | none | none | none |
| CL-CG-0-100-Bn | 100 | 100 | 104,000 | 3,600 | 3.16 | −10 | none | none | none |
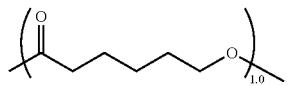
CL-CG-100-0
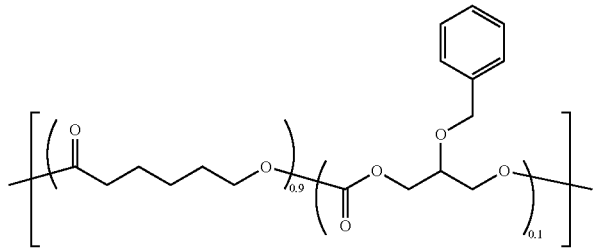
CL-CG-90-10-Bn
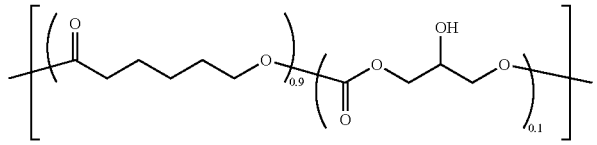
CL-CG-90-10-OH
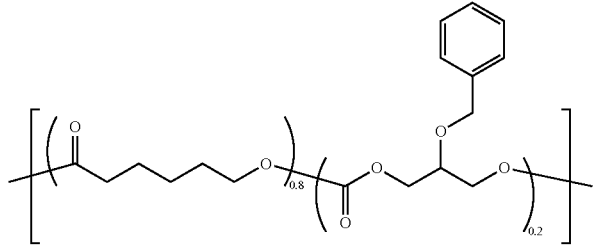
CL-CG-80-20-Bn
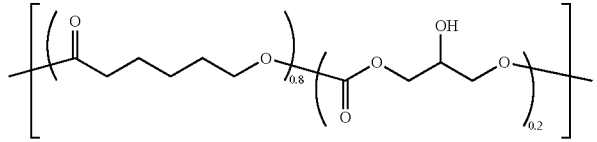
CL-CG-80-20-OH
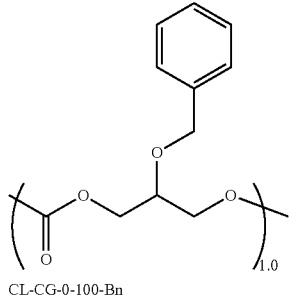
CL-CG-0-100-Bn
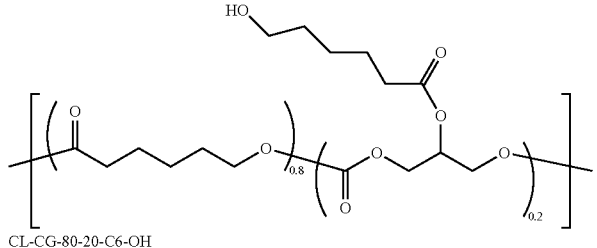
CL-CG-80-20-C6-OH TABLE 1-continued

| | | | Molecular Weights | | | Thermal Properties | | | |
|---|---|---|---|---|---|---|---|---|---|
| Polymer | $f_{cg}$ | $F_{cg}$ | $M_n$ (theo.) | $M_n$ (SEC) | $M_w/M_n$ | $T_g$ (°C.) | $T_c$ (°C.) | $T_m$ (°C.) | $\Delta H_f$ (J/g) |

CL-CG-80-20-C5-COOH

CL-CG-80-20-C6-NH2

CL-CG-70-30-Bn

CL-CG-60-40-Bn

Example 7

Poly(myristic acid carbonate-co-ε-caprolactone)

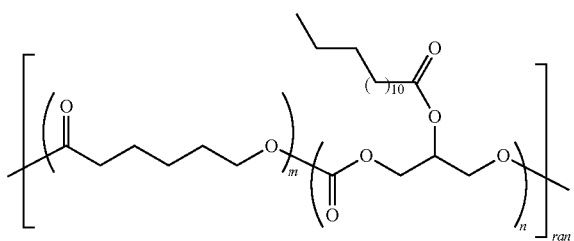

Poly(benzyloxy glycerol carbonate-co-ε-caprolactone) (1.0 g, 2.02 mmol), myristic acid (0.690 g, 3.03 mmol) and dimethylaminopyridine (DMAP) (0.123 g, 1.01 mmol) were dissolved in 100 mL dry dichloromethane. Dicyclohexylcarbodiimide (DCC) (0.500 g, 2.42 mmol) was added to the reaction mixture and a white precipitate formed. The mixture was stirred for 24 hours at room temperature under nitrogen. The precipitate compound was isolated by filtration and the filtrate was concentrated. The concentrated filtrate was dissolved in dichloromethane and precipitated in cold methanol (25 mL). The solvent was decanted and subsequently dried by evaporation. The resulting polymer was a white solid precipitate.

Example 8

Poly(stearic acid carbonate-co-ε-caprolactone)

Poly(benzyloxy glycerol carbonate-co-ε-caprolactone) (1.0 g, 2.02 mmol), stearic acid (0.859 g, 3.03 mmol) and DMAP (0.123 g, 1.01 mmol) were dissolved in 100 mL dry dichloromethane. DCC (0.500 g, 2.42 mmol) was added to the reaction mixture and a white precipitate formed. The mixture was stirred for 24 hours at room temperature under nitrogen. The precipitate compound was isolated by filtration and the filtrate was concentrated. The concentrated filtrate was dissolved in dichloromethane and precipitated in cold methanol (25 mL). The solvent was decanted and subsequently dried by evaporation. The resulting polymer was a white solid precipitate.

Example 9

Poly(oleic acid carbonate-co-ε-caprolactone)

Poly(benzyloxy glycerol carbonate-co-ε-caprolactone) (250 mg, 0.43 mmol) was dissolved in 25 mL of pyridine and cooled to 0° C. Oleoyl chloride (183 mg, 0.65 mmol) was added drop by drop. The mixture was stirred for 24 hours at room temperature under nitrogen. The pyridine was removed under vacuum, the crude product was dissolved in dichloromethane, and precipitated in cold methanol (25 mL). The solvent was decanted and subsequently dried by evaporation. The resulting polymer was a white solid precipitate.

Example 10

Amine Functionalized Poly Carbonate of Glycerol-co-caprolactone

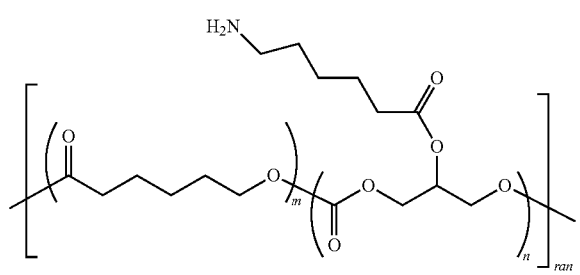

An amine-derivatized copolymer poly(6-amino-hexanoic acid 2-oxo-1,3-dioxan-5-yl ester-co-ε-caprolactone) was prepared using the following methods.

Synthesis of poly(fmoc-6-amino-hexanoic acid 2-oxo-1,3-dioxan-5-yl ester-co-ε-caprolactone)

Fmoc-6-amino-hexanoic acid (0.277 g, 0.78 mol), poly(5-hydroxy-1,3-dioxan-2-one-co-ε-caprolactone) (1.5 g, 2.6 mmol, 22 mol % carbonate), DCC (0.129 g, 0.63 mmol), and DMAP (0.032 g, 0.26 mmol) were dissolved in DCM (20 mL). The solution was stirred at RT for 18 h. The DCU was filtered and the solvent evaporated. The product was dissolved in dichloromethane (10 mL) and precipitated in cold methanol. The solvent was decanted and subsequently dried by evaporation (85% yield). Addition of the amine side chain was determined by the presence of the methylene group nearest the Fmoc protecting group, as well as the Fmoc protecting group itself, with peaks in the $^1$H NMR spectrum at 3.10-3.19 (m, 2H, OCH$_2$), and 4.45 (s, 2H, PhCH$_2$), 7.24-7.38 (m, 5H, aromatic), respectively.

Deprotection of poly(fmoc-6-Amino-hexanoic acid 2-oxo-1,3-dioxan-5-yl ester-co-ε-caprolactone)

The copolymer (300 mg) was dissolved in a 40% mixture of piperidine (16 mL) and dry dimethyl formamide (24 mL) and the reaction was stirred for 90 min. The solvents were evaporated under reduced pressure. The product was dissolved in dichloromethane (10 mL) and precipitated in cold methanol. The solvent was decanted and subsequently dried by evaporation (quantitative yield). Complete deprotection was determined by the absence of the Fmoc protecting group peaks in the $^1$H NMR spectrum at 4.88-4.95 (m, 2H, CH$_2$), and 7.24-7.75 (m, 5H, aromatic).

Example 11

Hydroxyl Functionalized Poly Carbonate of Glycerol-co-caprolactone

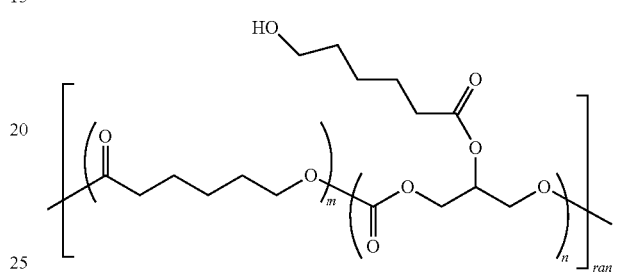

A primary alcohol-derivatized copolymer poly(6-hydroxy-hexanoic acid 2-oxo-1,3-dioxan-5-yl ester-co-ε-caprolactone) was synthesized using the following steps.

Synthesis of 6-benzyloxy-hexanoic acid

ε-caprolactone (10 mL, 0.18 mol), benzyl bromide (13.4 mL, 0.11 mol), and potassium hydroxide (11.3 g, 0.281 mol) were dissolved in toluene (200 mL). The reaction flask was placed in a 120° C. pre-heated oil bath and refluxed overnight under stirring. The mixture was then neutralized using 1 M HCl (300 mL), the toluene evaporated off, and the product extracted using dichloromethane (3×300 mL) to afford a mixture of mono and di-protected 6-hydroxy-hexanoic acid. The crude product was saponificated with 1M sodium hydroxide (200 mL) and methanol (200 mL), extracted with dichloromethane (3×200 mL), and the solvent was evaporated under reduced pressure to afford pure 6-benzyloxy-hexanoic acid (72% yield). $^1$H NMR (CDCl$_3$) 1.38-1.46 (m, 2H, CH$_2$), 1.57-1.68 (m, 4H, CH$_2$CH$_2$), 2.32-2.38 (m, 2H, CH$_2$COOH), 3.42-3.46 (m, 2H, OCH$_2$), 4.48-4.53 (s, 2H, PhCH$_2$), 7.27-7.31 (m, 5H, aromatic).

Poly(6-benzyloxy-hexanoic acid 2-oxo-1,3-dioxan-5-yl ester-co-ε-caprolactone)

6-Benzyloxy-hexanoic acid (0.173 g, 0.78 mmol), poly(5-hydroxy-1,3-dioxan-2-one-co-ε-caprolactone) (1.5 g, 2.6 mmol, 22 mol % carbonate), DCC (0.129 g, 0.63 mmol), and DMAP (0.032 g, 0.26 mmol) were dissolved in DCM (20 mL). The solution was stirred at RT for 18 h. The DCU was filtered and the solvent evaporated. The product was dissolved in dichloromethane (10 mL) and precipitated in cold methanol. The solvent was decanted and subsequently dried by evaporation (86% yield). Addition of the alcohol side chain was determined by the presence of the methylene group nearest the benzyl protecting group, as well as the benzyl protecting group itself, with peaks in the $^1$H NMR spectrum at 3.40-3.44 (m, 2H, OCH$_2$), and 4.48-4.53 (s, 2H, PhCH$_2$), 7.27-7.31 (m, 5H, aromatic), respectively.

Deprotection of poly(6-benzyloxy-hexanoic acid 2-oxo-1,3-dioxan-5-yl ester-co-ε-caprolactone)

The copolymer (300 mg) was dissolved in 50 mL dry dichloromethane inside a Parr bottle. 10% Pd/C (50 mg) and 20% Pd(OH)$_2$/C (50 mg) were then added to the solution. The reaction mixture was evacuated and purged with hydrogen three times. The flask was then pressurized to 60 psi with hydrogen and shaken for 24 hours. The reaction mixture was filtered through Celite and the filter cake washed with 50 mL dichloromethane. The solvents were then evaporated to yield the final polymer (quantitative yield). Complete deprotection was determined by the absence of the benzyl protecting group peaks in the $^1$H NMR spectrum at 4.48-4.53 (s, 2H, PhCH$_2$), 7.27-7.31 (m, 5H, aromatic).

Example 12

Carboxylic Acid Functionalized Poly Carbonate of Glycerol-co-caprolactone

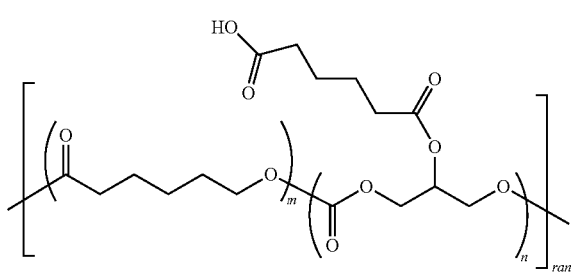

A carboxylic acid-derivatized copolymer poly(hexanedioic acid mono-(2-oxo-1,3-dioxan-5-yl) ester-co-ε-caprolactone) was synthesized using the following steps.

Synthesis of Hexanedioic Acid Monobenzyl Ester

DOWEX® 50W-X2 (2 g), benzyl formate (10 mL, mol), and adipic acid (2 g, mol) were added to octane (10 mL). The mixture was refluxed for 4 hours at 100° C., and the crude product was purified via silica chromatography to yield a clear, colorless liquid (87% yield). $^1$H NMR (CDCl$_3$) 1.59-1.78 (m, 4H, CH$_2$CH$_2$), 2.33-2.39 (m, 4H, CH$_2$COOH), 5.09 (s, 2H, PhCH$_2$), 7.25-7.30 (m, 5H, aromatic).

Poly(hexanedioic acid mono-(2-oxo-1,3-dioxan-5-yl) ester-co-ε-caprolactone)

Hexanedioic acid monobenzyl ester (0.184 g, 0.78 mmol), poly(5-hydroxy-1,3-dioxan-2-one-co-ε-caprolactone) (1.5 g, 2.6 mmol, 22 mol % carbonate), DCC (0.129 g, 0.63 mmol), and DMAP (0.032 g, 0.26 mmol) were dissolved in dichloromethane (20 mL). The solution was stirred at RT for 18 h. The DCU was filtered and the solvent evaporated. The product was dissolved in dichloromethane (10 mL) and precipitated in cold methanol. The solvent was decanted and subsequently dried by evaporation (83% yield). Addition of the carboxylic acid side chain was determined by the presence of the benzyl protecting group, with peaks in the $^1$H NMR spectrum at 5.06 (s, 2H, PhCH$_2$), 7.27-7.33 (m, 5H, aromatic).

Deprotection of poly(6-benzyloxy-hexanoic acid 2-oxo-1,3-dioxan-5-yl ester-co-ε-caprolactone)

The copolymer (300 mg) was dissolved in 50 mL dry dichloromethane inside a Parr bottle. 10% Pd/C (50 mg) and 20% Pd(OH)$_2$/C (50 mg) were then added to the solution. The reaction mixture was evacuated and purged with hydrogen three times. The flask was then pressurized to 60 psi with hydrogen and shaken for 24 hours. The reaction mixture was filtered through Celite and the filter cake washed with 50 mL dichloromethane. The solvents were then evaporated to yield the final polymer (quantitative yield). Complete deprotection was determined by the absence of the benzyl protecting group peaks in the $^1$H NMR spectrum at 5.06 (s, 2H, PhCH$_2$), 7.27-7.33 (m, 5H, aromatic).

Example 13

Poly(benzyloxy glycerol thiol carbonate-co-ε-caprolactone)

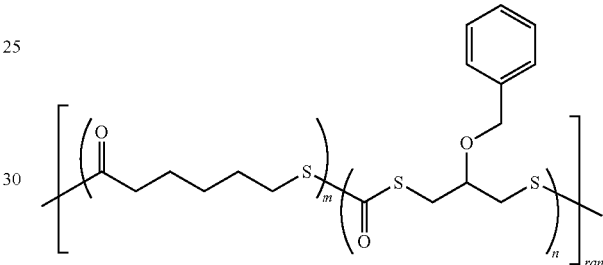

5-(benzyloxymethyl)-1,3-dithian-2-one and ε-capro-thiol-lactone are combined with varying ratios (to a total of 10.0 mmol) in a 10 mL schlenk flask and subsequently evacuated and flushed with N$_2$ three times. Meanwhile, the catalyst (Sn(oct)$_2$, 6.5 μL, 0.02 mmol, monomer/initiator ratio=500) is evacuated in a small flask for 60 minutes. The Schlenk flask is partially submerged in a thermostatted oil bath, preheated to 140° C. Toluene (400 μL) is added to the catalyst and the mixture injected via syringe to the monomers. The reaction is stirred for 48 hours, removed from heat, and cooled to room temperature. The polymer is dissolved in dichloromethane (10 mL) and precipitated in cold methanol. The solvent is decanted and subsequently dried by evaporation. The resulting polymer forms either a viscous oil or white solid precipitate depending on the carbonate content of the copolymer.

Example 14

Poly(hydroxy glycerol thiol carbonate-co-ε-caprolactone)

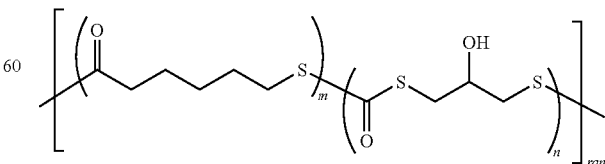

Poly(benzyloxy glycerol thiol carbonate-co-ε-caprolactone) is dissolved in 50 mL dry dichloromethane inside a Parr bottle. 10% Pd/C (50 mg) and 20% Pd(OH)$_2$/C (50 mg) are added to the solution. The reaction mixture is evacuated and purged with hydrogen three times. The flask is pressurized to 60 psi with hydrogen and shaken for 24 hours. The reaction mixture is filtered through Celite and the filter cake washed with 50 mL of dichloromethane. The solvents are evaporated to yield the final polymer.

Example 15

Poly(stearic acid thiol carbonate-co-ε-caprolactone)

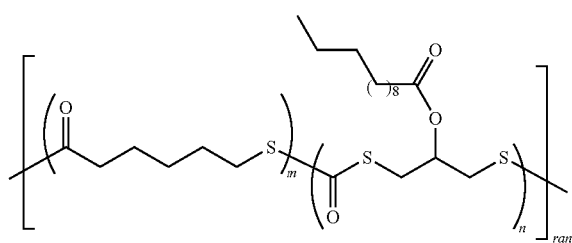

Poly(benzyloxy glycerol thiol carbonate-co-ε-caprolactone), stearic acid, and DMAP are dissolved in 100 mL dry dichloromethane. DCC is added to the reaction mixture and a white precipitate forms. The mixture is stirred for 24 hours at room temperature under nitrogen. The precipitate compound is isolated by filtration and the filtrate was concentrated. The concentrated filtrate is dissolved in dichloromethane and precipitated in cold methanol (25 mL). The solvent is decanted and subsequently dried by evaporation.

Example 16

Fabrication of Paclitaxel Containing PLGA Microparticles

Bioabsorbable poly D,L-lactide-co-glycolide (PLGA) microparticles can be used for the delivery of paclitaxel. The fabrication techniques used to create PLGA microparticles were modified from Edlund & Albertsson and Wang et. al. (Edlund et al., Adv. Polymer Sci., 157:67-112, 2001; Wang et al., Chem. Pharm. Bull., (Tokyo) 44:1935, 1996) and utilized a water in oil emulsion technique. First, 0.5 g of 75:25 PLGA (Absorbable Polymer International, Birmingham, Ala.) tablets (the greater the ratio of lactic acid to glycolic acid the slower the release) were dissolved in 4 mL dichloromethane (Sigma Aldrich, St. Louis, Mo.) using a vortexing device. After the plastic was completely dissolved, 50 mg of paclitaxel (Taxol, MP Biomedical Irvine, Calif.) previously solubilized in ~100 μl of dimethyl sulfoxide (DMSO, Fisher Hampton, N.H.), was added and further vortexed. In the fabrication of control PLGA beads only DMSO was added. The solution was placed in 10 ml of 5% polyvinyl alcohol surfactant (Fisher) and vortexed for 15 minutes (or sonicated using a probe tip sonicator) and stirred overnight. The microparticles were collected and washed three times in 50 mL of distilled/deionized water. Following washing, the microparticles were lyophilized (freeze dried) and stored at −20° C. to insure the stability of Paclitaxel. The encapsulation efficiency of taxol by the microparticles was determined to be 74%+/−4% by HPLC analysis.

Example 17

Synthesis of Nanoparticles by Miniemulsion

Nanoparticles were prepared using a modification of a miniemulsion polymerization method previously reported (Landfester et al., Macromolecules 32:5222-8, 1999). Briefly, 5-methyl-2-(2,4,6-trimethoxyphenyl)-[1,3]-5-dioxanylmethyl methacrylate and 2,2'-azobis(2-methylpropionitrile) (AIBN), a free-radical initiator, were dissolved in dichloromethane, followed by removal of the solvent via rotary evaporation until a viscous mixture remained. Alternatively, 5-methyl-2-(2,4,6-trimethoxyphenyl)-[1,3]-5-dioxanylmethyl methacrylate, 0.25 mg of paclitaxel, and 2,2'-azobis(2-methylpropionitrile) (AIBN), a free-radical initiator, were dissolved in dichloromethane, followed by removal of the solvent via rotary evaporation until a viscous mixture remained. This viscous mixture was then mixed with a solution of sodium dodecyl sulfate, a stabilizing surfactant, in 10 mM pH 8 phosphate buffer. This mixture was then sonicated for 1 hour (1 second pulses with a 2 second delay) with 30 W of power, forming the miniemulsion and allowing the solvent to evaporate. Following sonication, the miniemulsion was transferred onto a temperature-controlled oil bath and stirred at 65° C. for 2 hours to initiate the free-radical polymerization. The resulting polymeric nanoparticles were then dialyzed against 5 mM pH 8 phosphate buffer over two days to remove excess surfactant and salts.

Example 18

Synthesis of Nanoparticles Using Photoinitiation

5-Methyl-2-(2,4,6-trimethoxyphenyl)-[1,3]-5-dioxan-5-yl-methyl methacrylate was dissolved in dichloromethane, followed by removal of the solvent via rotary evaporation until a viscous mixture remained. Alternatively, methyl-2-phenyl-[1,3]-5-dioxanylmethyl methacrylate and 0.25 mg of paclitaxel was dissolved in dichloromethane, followed by removal of the solvent via rotary evaporation until a viscous mixture remained. This viscous oil was then mixed with a solution of sodium dodecyl sulfate, the stabilizing surfactant, in 20 mM triethanolamine buffer. This mixture was then sonicated for 30 min (1 s pulses with a 2 s delay) with 30 W of power, forming the miniemulsion and allowing the solvent to partially evaporate. Following sonication, Eosin Y and 1-vinyl-2-pyrrolidone were added to the emulsion to give final concentrations of 0.2 mM and 2 mM, respectively. This mixture was then exposed to light from a mercury arc lamp operating at 300 W for 10 min while being stirred vigorously, causing polymerization. Following photopolymerization, the particles were stirred overnight while open to the air to allow any remaining solvent to evaporate. The resulting polymeric nanoparticles were then dialyzed against 5 mM pH 8 phosphate buffer over two days to remove excess surfactant and salts.

Example 19

Nanoparticles Prepared by a Precipitation Method

5-Methyl-2-(2,4,6-trimethoxyphenyl)-[1,3]-5-dioxanylmethyl methacrylate (0.45 g, 1.2 mmol) and benzoyl peroxide (2.6 mg, 0.011 mmol) were dissolved in dry toluene (10 mL). The flask was evacuated and refilled with nitrogen three times to remove oxygen. The mixture was then stirred at 70° C. for 14 hours. The solvent was removed by rotary evaporation, and the remaining material was dissolved in CH$_2$Cl$_2$ (5 mL) and precipitated in cold diethyl ether (50 mL). The solid precipitate was collected by vacuum filtration. The product was obtained as a white powder at 36.5% yield.

Nanoparticles were prepared by first dissolving the polymer (50 mg) in CH$_2$Cl$_2$ (1.0 mL) and dissolving sodium dodecyl sulfate (50 mg) in deionized water (10 mL). Alternatively, nanoparticles were prepared by first dissolving the polymer (50 mg) and paclitaxel (0.5 mg) in CH$_2$Cl$_2$ (1.0 mL) and dissolving sodium dodecyl sulfate (50 mg) in deionized water (10 mL). The organic solution was then added to the aqueous surfactant solution, and this mixture was sonicated at 30 W of power for 5 minutes to produce the emulsion. The mixture was stirred while open to the atmosphere overnight to evaporate the excess CH$_2$Cl$_2$. Dialysis using a membrane with a 3400 molecular weight cutoff was used to remove excess surfactant. Nanoparticles prepared using this monomer do not swell at pH>1.

Example 20

Fabrication of Poly(hydroxy glycerol carbonate-co-ε-caprolactone) Drug-Eluting Microparticles Poly(hydroxy glycerol carbonate-co-ε-caprolactone) microparticles were used for the delivery of pemetrexed. The fabrication techniques used to create the microparticles utilize a water in oil in water emulsion technique. First, 0.5 g of 20:80 poly(hydroxy glycerol carbonate-co-ε-caprolactone) was dissolved in 4 mL dichloromethane (Sigma Aldrich, St. Louis, Mo.) using a vortexing device. After the polymer was completely dissolved, 50 mg of pemetrexed previously solubilized in 0.9% NaCl, was added and further vortexed. In the fabrication of control poly(hydroxy glycerol carbonate-co-ε-caprolactone) beads only 0.9% NaCl was added. The solution was placed in 10 ml of 5% poly vinyl alcohol surfactant (Fisher) and vortexed for 15 minutes (or sonicated using a probe tip sonicator) and stirred overnight. The microparticles were collected and washed three times in 50 ml of distilled/deionized water. Following washing, the microparticles were lyophilized (freeze dried) and stored at −20° C. to insure the stability of pemetrexed.

Example 21

Fabrication of Poly(hydroxy glycerol carbonate-co-ε-caprolactone) Nanoparticles with Fluorescent Tag 7-(diethylamino)coumarin-3-carboxylic acid (0.005 g, 19.5 nmol), poly(5-hydroxy-1,3-dioxan-2-one-co-ε-caprolactone) (1.5 g, 2.6 mmol, 22 mol % carbonate), DCC (0.129 g, 0.63 mmol), and DMAP (0.032 g, 0.26 mmol) were dissolved in DCM (20 mL). The solution was stirred at RT for 18 hours. The DCU was filtered and the solvent evaporated (quantitative yield). The crude product was redissolved in THF, purified using Sephadex LH-20 chromatography and further dialyzed (Pierce, 3,500 MWCO) for approximately 48 hours to ensure all residual unbound dye was removed.

Coumarin-bound copolymer particles were prepared by an emulsion/solvent evaporation method. Briefly, 1.0 g of copolymer was dissolved in 20 mL dichloromethane. The solution was poured into a mixture of 200 mL deionized water containing 0.5% w/v SDS. The emulsion was stirred for 5 minutes before being sonicated (~30 W) for 30 minutes, and finally dialyzed for approximately 48 hours to remove the SDS.

The nanoparticle stock solution (5 mg/mL) was diluted to a final concentration of 0.01 mg/mL with serum-free medium (Dulbecco's Modified Eagle Medium). A549 human lung carcinoma cells (American Type Culture Collection, Manassas, Va.) were plated onto a 96 well plate at a density of 5,000 cells/well and incubated overnight, or until about 90% confluence. The medium from each well was removed and replaced with 100 μL of 0.01 mg/mL nanoparticle solution and the cells were subsequently incubated with the particles for 2 hours. The nanoparticle suspension was then removed, the cells were washed directly three times with PBS, and the cells were imaged immediately via fluorescence microscopy with a FITC filter.

Example 22

Fabrication of Poly(stearic acid carbonate-co-ε-caprolactone) Nanoparticles

The nanoparticles were prepared by an emulsion/solvent evaporation method. Briefly, poly(stearic acid carbonate-co-ε-caprolactone) was dissolved in 20 mL dichloromethane. Alternatively, poly(stearic acid carbonate-co-ε-caprolactone) was dissolved in 20 mL dichloromethane containing either 1 or 10 wt % paclitaxel per weight of polymer. The solution was poured into a mixture of 200 mL deionized water containing 0.5% w/v SDS. The emulsion was stirred for 5 minutes before being sonicated (~30 W) for 30 minutes, and finally dialyzed for approximately 1 hour to remove the SDS.

Example 23

Nanoparticle Expanding in Acidic but not Neutral Conditions

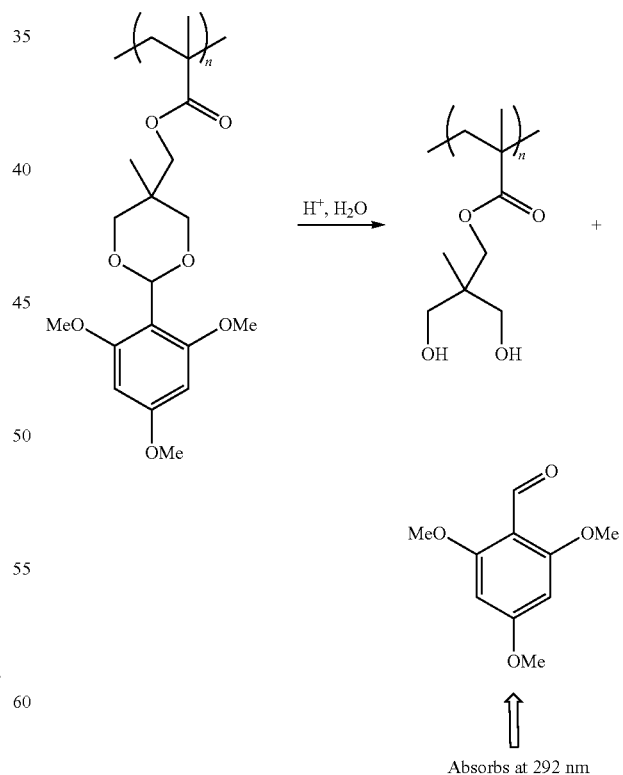

Absorbs at 292 nm

Figure 9:
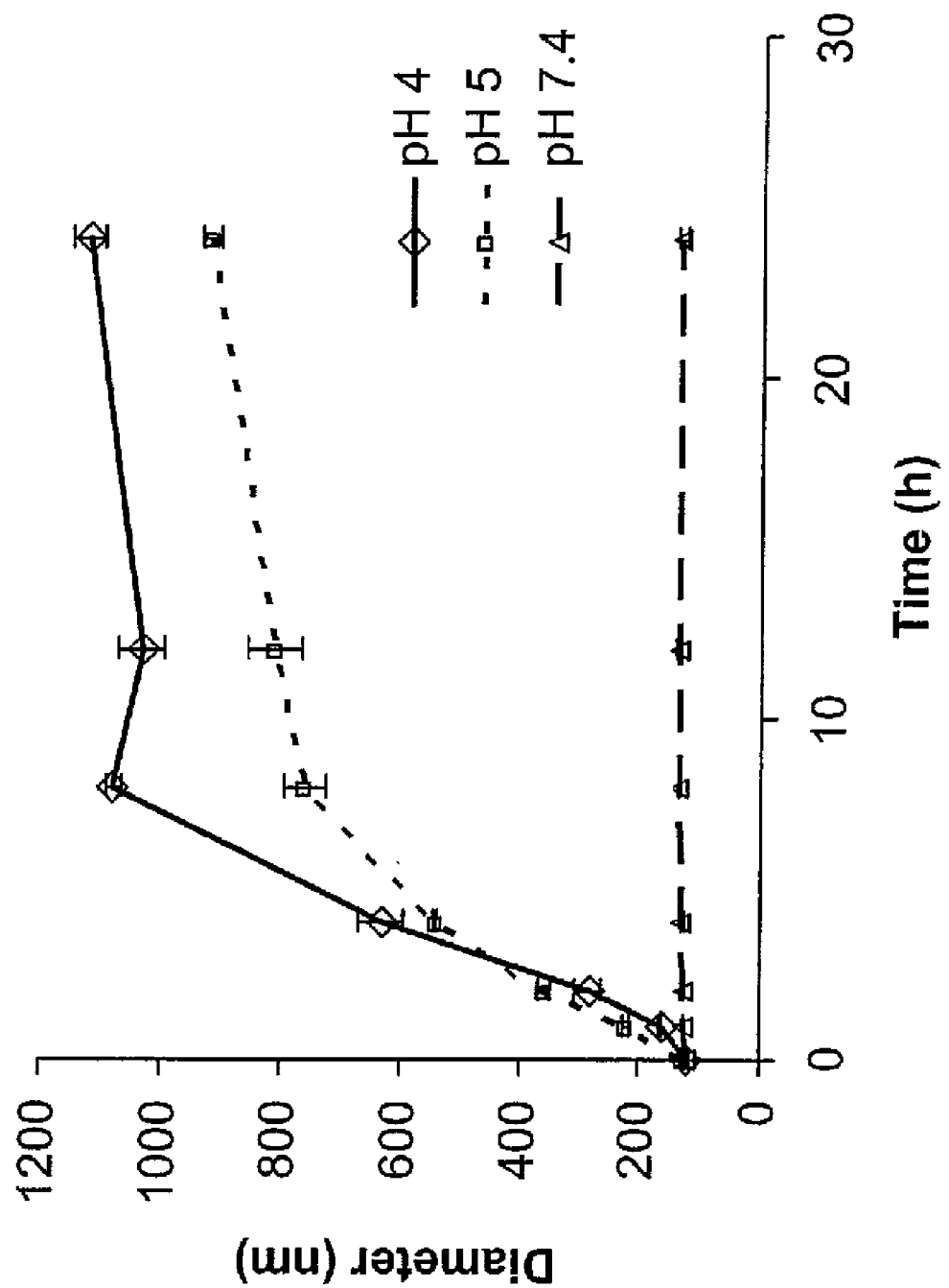
FIG. 9 is a graph showing particle swelling at various pHs.
Figure 10:
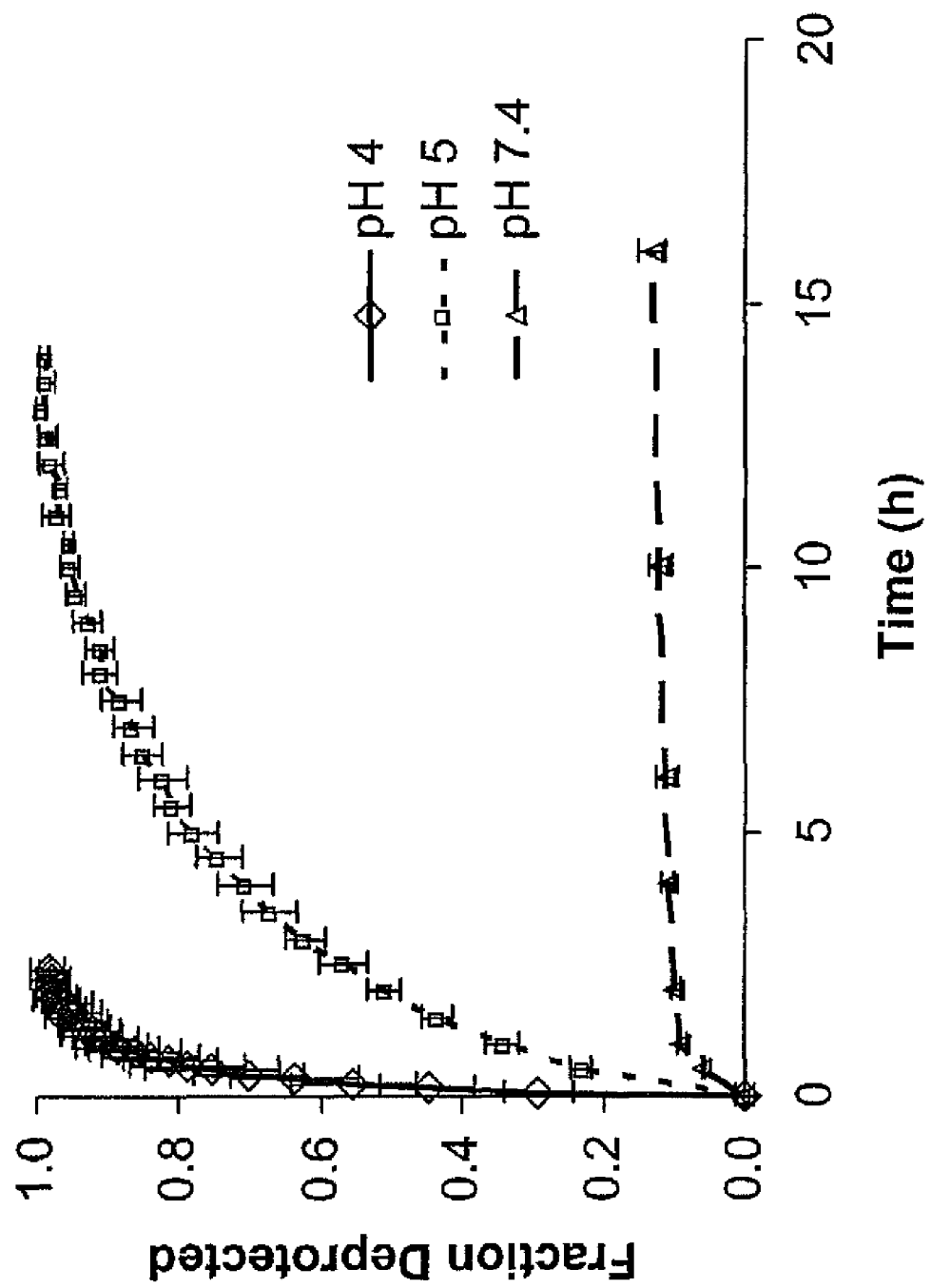
FIG. 10 is a graph showing the deprotection observed by absorbance using UV/Vis spectroscopy at a wavelength of 292 nm.

A sample of the nanoparticles from Example 18 was diluted in buffer at a pH 4, 5, or 7.4 and maintained at 37° C. The diameter of the particles was then measured at regular time intervals using dynamic light scattering (DLS), showing how the particles increased in size over time. Prior to each DLS measurement, the samples were sonicated for 5 seconds to break up aggregates. Particle swelling from 100 nm in diameter to near 1 μm in diameter was observed (see FIG. 9). In addition, the release of free 2,4,6-trimethoxybenzaldehyde was observed using UV/Vis spectroscopy at a wavelength of 292 nm, also indicating deprotection of the polymer side groups (see FIG. 10).

These particles are useful for controlled release applications as well as for cosmetic applications in which the increase in volume could reduce wrinkles of increase the sized of tissue into which these polymers are injected.

Example 24

Nanoparticle and Swelling from a Sugar Analog

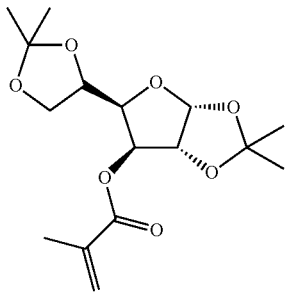

Synthesis of 1,2:5,6-di-O-isopropylidene-3-O-methacryloyl-α-D-glucofuranose: The synthesis of this compound was carried out as described by Black et al. and is described briefly. (Black et al., Journal of the Chemical Society, 4433-4439, 1963). 1,2:5,6-di-O-isopropylidene-α-D-glucofuranose (1.00 g, 3.86 mmol) and methacrylic anhydride (1.2 mL, 1.2 g, 8.1 mmol) were dissolved in pyridine (5 mL) and stirred at 65° C. for 3.5 hours. Then water (2.5 mL) was added, and stirring at 65° C. was continued for another 1.5 hours and then at room temperature overnight. The mixture was extracted with hexanes (5 mL×3), and the combined hexanes extracts were then washed with 1 M NaOH (15 mL×3) and deionized water (15 mL), followed by drying over $Na_2SO_4$. The solvent was removed using rotary evaporation, and the remaining compound was dried under high vacuum. The product was obtained as a clear oil at 74.2% yield.

Figure 12:
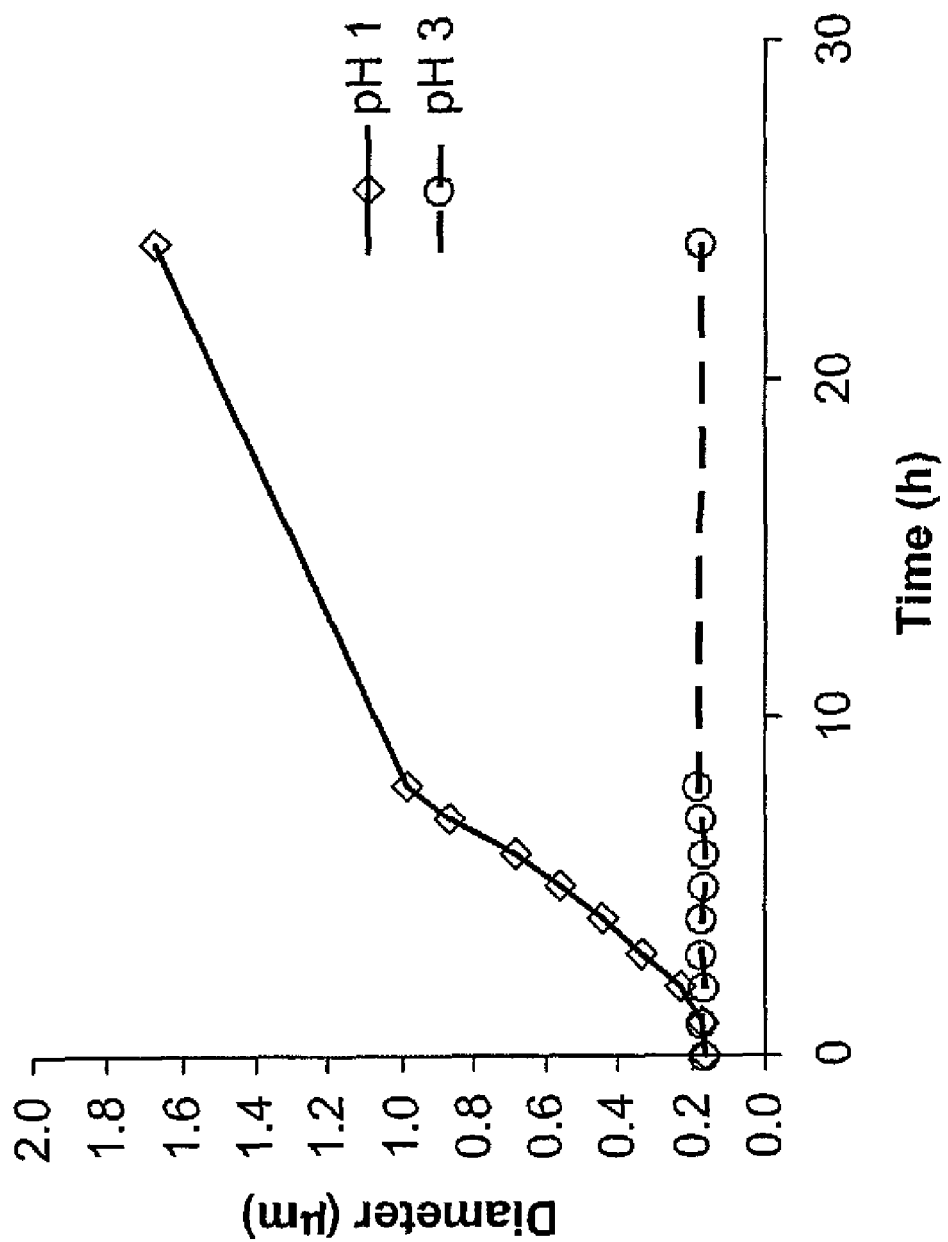
FIG. 12 is a graph of the diameter of sugar derived nanospheres at various pHs.

Nanoparticles were prepared from the resulting product by methods described herein. A sample of the nanoparticles was diluted in 0.1 M HCl and maintained at 25° C. The diameter of the particles was then measured at regular time intervals using dynamic light scattering (DLS), showing how the particles increased in size over time (FIG. 12). FIG. 12 shows that at a pH of about 1.0, the particle size changes from about 200 nm to about 1600 nm over the course of about 24 hours, whereas at a pH of about 3.0, the particle size is stable over the same time period.

Example 25

Formation of Single-Layer Polymer Films

Polymer films were cast onto glass by depositing a polymer solution comprised of an individual copolymer including but not limited to poly(stearic acid carbonate-co-ε-caprolactone), dissolved in dichloromethane, tetrahydrofuran, or toluene, using a microsyringe. The solvent was removed by slow evaporation overnight and then placed under reduced pressure for 24 hours.

Example 26

Formation of Multi-Layered Polymer Films

Poly(stearic acid carbonate-co-ε-caprolactone) films were adhered between poly(lactic-co-glycolic acid) films A poly (lactic-co-glycolic acid)/dichloromethane solution was deposited onto glass using a microsyringe to form a film. A poly(stearic acid carbonate-co-ε-caprolactone)/dichloromethane solution was deposited onto the poly(lactic-co-glycolic acid) film using a microsyringe to form a second layer. A poly(lactic-co-glycolic acid)/dichloromethane solution was deposited onto the poly poly(stearic acid carbonate-co-ε-caprolactone) film using a microsyringe to form a third layer.

Example 27

Deposition of Polymer Films on a Substrate

Polymer films were cast onto substrates composed of either glass, collagen, pericardium, TEFLON®, or titanium by depositing a polymer solution comprised of an individual copolymer including but not limited to poly(stearic acid carbonate-co-ε-caprolactone), dissolved in dichloromethane, tetrahydrofuran, or toluene, using a microsyringe. The solvent was removed by slow evaporation overnight and then placed under reduced pressure for 24 hours.

Example 28

Incorporation 10-hydroxycaptothecin into Polymer Films

Drug loaded polymeric films were cast or sprayed onto glass by depositing a polymer solution of poly(stearic acid carbonate-co-ε-caprolactone), dichloromethane, and 10-hydroxycamptothecin, using a microsyringe or aerosol device. The solvent was removed by slow evaporation overnight and then placed under reduced pressure for 24 hours.

Example 29

Incorporation and Patterning of 10-Hydroxycaptothecin into Polymer Films

Patterned drug loaded polymeric films were cast onto glass by using a microprinter or microsyringe by depositing a polymer solution of poly(stearic acid carbonate-co-ε-caprolactone), dichloromethane, and 10-hydroxycamptothecin, in a controlled manner to form patterns such as stripes and dots. The solvent was removed by slow evaporation overnight and then placed under reduced pressure for 24 hours. This method can also be used with more than one polymer simultaneously.

Example 30

Release of 10-Hydroxycamptothecin from Poly(ε-caprolactone)

Drug-loaded polymer films were cast onto glass by depositing a polymer solution comprised of poly(caprolactone) (5 mg), dichloromethane (50 μL), and 10-hydroxycamptothecin (100 μg), using a microsyringe. The solvent was removed by slow evaporation over night and then placed under reduced pressure for 24 hours. An initial burst was seen over the first two days, releasing at a rate of about 5 μg/day.

Drug-loaded polymer films were also cast onto glass by depositing a polymer solution comprised of poly(stearic carbonate-co-ε-caprolactone) (5 mg), dichloromethane (50 μL), and paclitaxel (100 μg), using a microsyringe. The solvent was removed by slow evaporation over night and then placed under reduced pressure for 24 hours. The resulting films were homogenous and opaque, with good adherence to the glass substrate. The films released taxol over time.

Example 31

Release of 10-Hydroxycamptothecin or Paclitaxel from Poly(stearic acid carbonate-co-ε-caprolactone)

Drug-loaded polymer films were cast onto glass by depositing a polymer solution comprised of poly(stearic acid carbonate-co-ε-caprolactone) (5 mg), dichloromethane (50 μL), and 10-hydroxycamptothecin (100 μg), using a microsyringe. The solvent was removed by slow evaporation over night and then placed under reduced pressure for 24 hours. A slight initial burst was seen over the first two days, releasing at a rate of about 3 μg/day. Continuous release occurred over at least 30 days at a nearly constant rate of about 1 μg/day.

Alternatively, drug-loaded polymer films were cast onto glass by depositing a polymer solution comprised of poly (stearic carbonate-co-ε-caprolactone) (5 mg), dichloromethane (50 μL), and paclitaxel (100 μg), using a microsyringe. The solvent was removed by slow evaporation over night and then placed under reduced pressure for 24 hours. The resulting films were homogenous and opaque, with good adherence to the glass substrate. The films released taxol over time.

Example 32

Release of 10-Hydroxycamptothecin from Poly(hydroxy glycerol carbonate-co-ε-caprolactone)

Drug-loaded polymer films were cast onto glass by depositing a polymer solution comprised of poly(hydroxy glycerol carbonate-co-ε-caprolactone) (5 mg), dichloromethane (50 μL), and 10-hydroxycamptothecin (100 μg), using a microsyringe. The solvent was removed by slow evaporation over night and then placed under reduced pressure for 24 hours. An initial burst was seen over the first day, releasing at a rate of about 18 μg/day. Continuous release occurred over at least 30 days, beginning at a rate of 3 μg/day and slowly decreasing to less than 1 μg/day at four weeks.

Example 33

Figure 3:
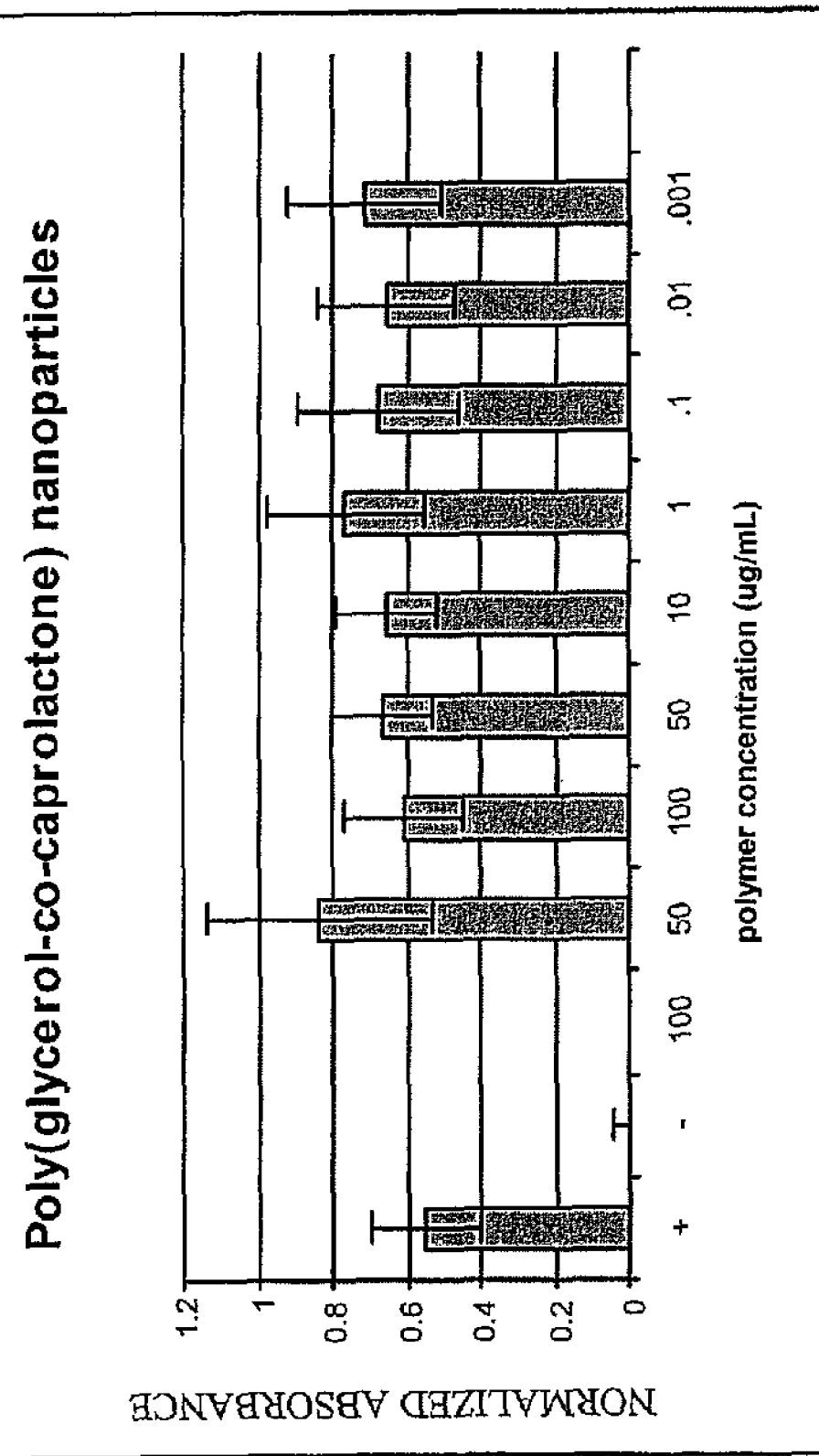
FIG. 3 is a bar graph showing the cytotoxicity of poly (glycerol-co-caprolactone) nanoparticles.
Figure 4:
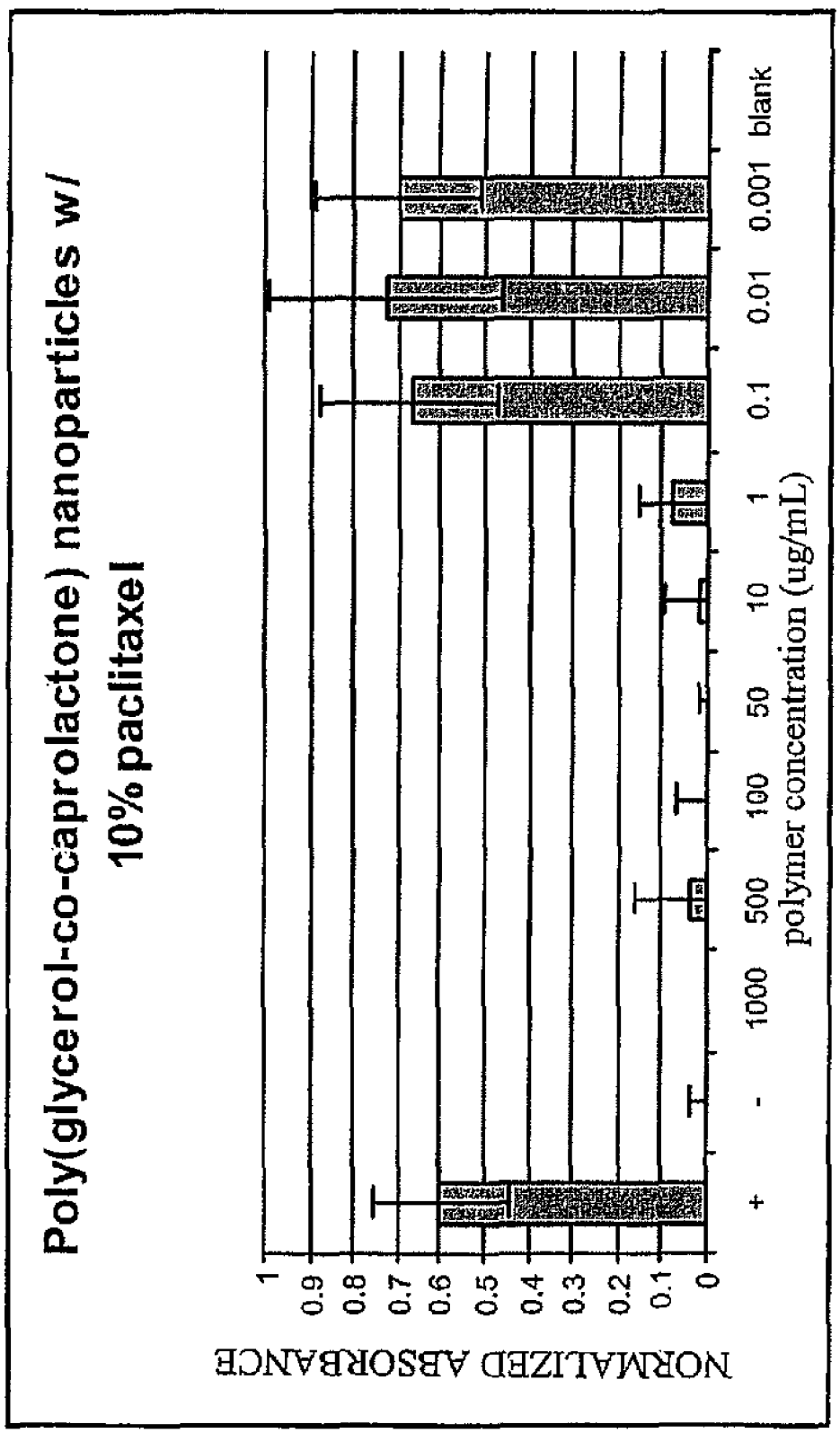
FIG. 4 is a bar graph showing the cytotoxicity of poly (glycerol-co-caprolactone) nanoparticles with 10% paclitaxel.
Figure 5:
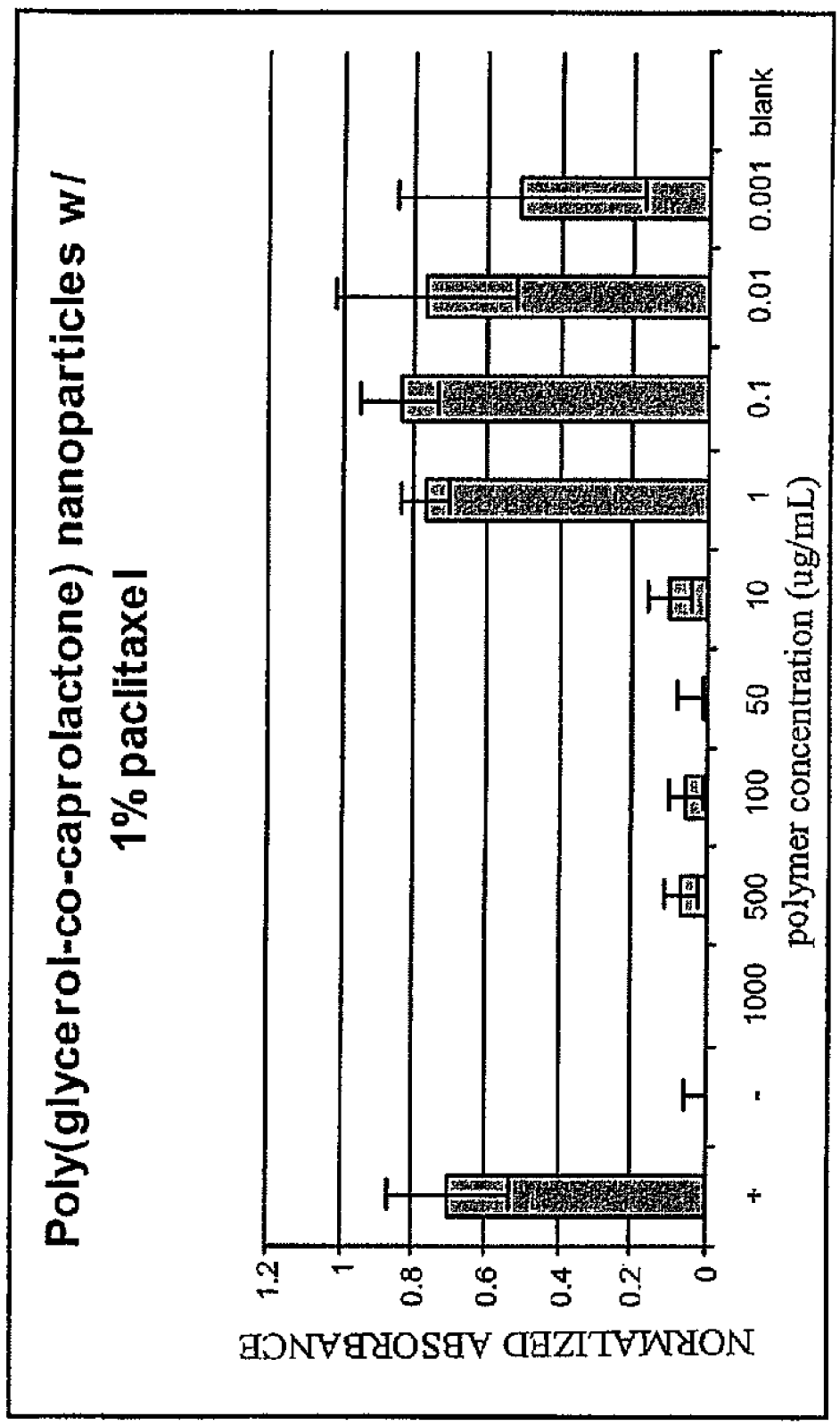
FIG. 5 is a bar graph showing the cytotoxicity of poly (glycerol-co-caprolactone) nanoparticles with 1% paclitaxel.

In Vitro Tumor Cytoxicity with Paclitaxel-Loaded Poly(stearic acid carbonate-co-ε-caprolactone) Nanoparticles Lewis Lung Carcinoma (LLC) cells were washed with sterile phosphate buffered saline (PBS) and trypsinized. The cells were then counted using a Coulter counter and plated 3,000 cells/well in 96 well plates. Cells were serum starved overnight and then treated with empty nanoparticles, paclitaxel-loaded nanoparticles (10% paclitaxel), and paclitaxel-loaded nanoparticles (1% paclitaxel) for a five day period. A positive control contained 10% FBS or the same concentration of FBS provided for treated cells, while a negative control lacked FBS. At the completion of the assay the cells were incubated with 50 μL of 1× Thiazolyl Blue Tetrazolium Bromide (MTT, Sigma) dissolved in PBS at 37° C. for two hours. The media was then aspirated and 100 μL of DMSO was added to each well. The plates were then placed on a shaking device for 10 minutes and the wells turned purple, corresponding with the numbers of viable mitochondria in the well. The plates were placed on an ELISA reader and scanned at a wavelength of 570 nm. The absorbance values were normalized to values from a known number of stained cells. No cytotoxicity was observed with the empty nanoparticles (as a control, FIG. 3), whereas cytotoxicity was observed with the taxol loaded nanoparticles, as shown in FIGS. 4 and 5.

Example 34

Release of 10-Hydroxycamptothecin from Poly((lauric, myristic, palmitic, or stearic) glycerol carbonate-co-ε-caprolactone)

Figure 6:
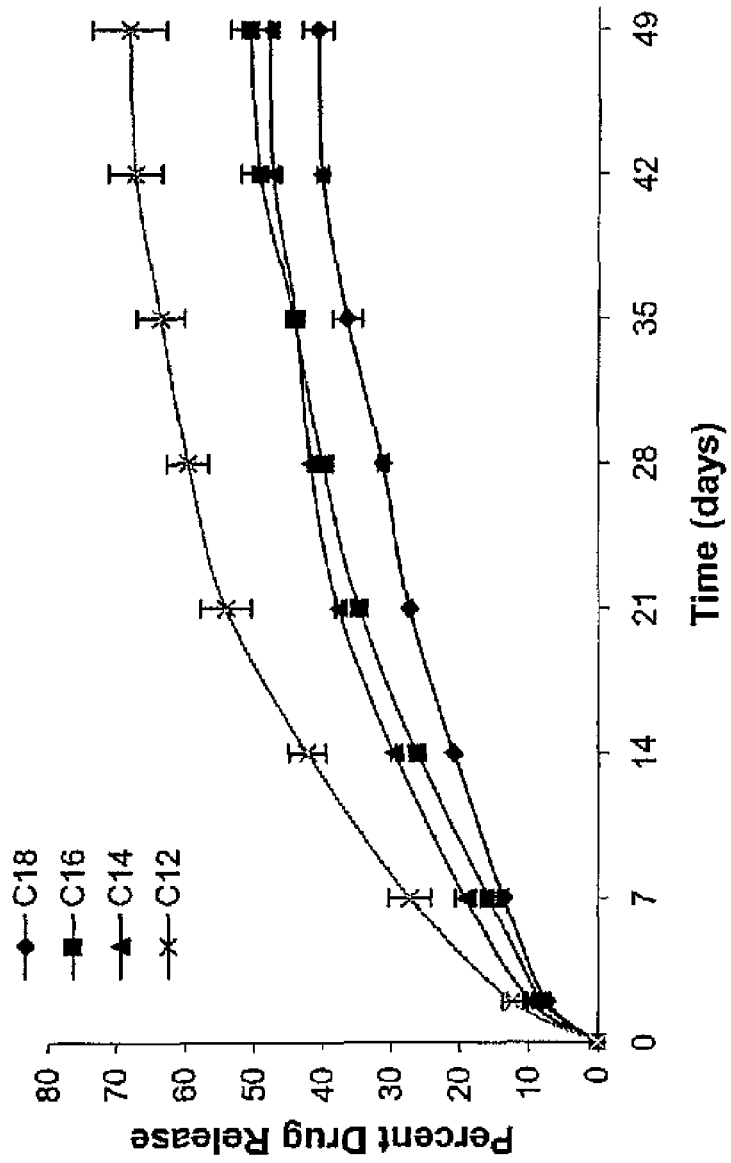
FIG. 6 is a graph showing the release of 10-hydroxycamptothecin from poly(lauric, myristic, palmitic, or stearic glycerol carbonate-co-caprolactone) films.

Drug-loaded polymer films were cast onto glass by depositing a polymer solution comprised of poly((lauric, myristic, palmitic, or stearic) carbonate-co-ε-caprolactone) (5 mg), dichloromethane (50 μL), and 10-hydroxycamptothecin (100 μg), using a microsyringe. The solvent was removed by slow evaporation over night and then placed under reduced pressure for 24 hours. An initial burst was seen over the first day, releasing at a rate of about 8-10 μg/day. Continuous release occurred over at least 49 days, beginning at a rate of 1-3 μg/day and slowly decreasing to less than 1 μg/day at four weeks (see FIG. 6). FIG. 6 shows that increasing the hydrophobicity of the polymer decreases release from the polymers. Intermediate release profiles to those shown can be obtained by mixing or blending the polymers.

Example 35

Figure 7:
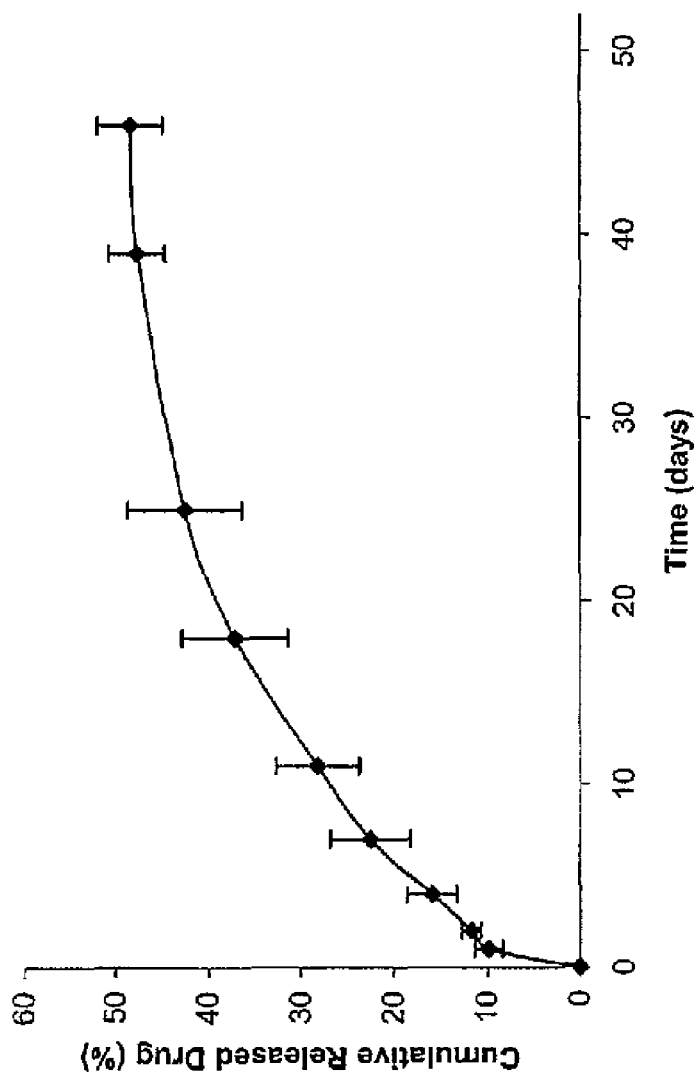
FIG. 7 is a graph showing 10-hydroxycamptothecin release from poly(stearic glycerol carbonate-co-caprolactone) films on pericardium strips.

Release of 10-Hydroxycamptothecin from Poly(stearic glycerol carbonate-co-ε-caprolactone) on Pericardium Strips Drug-loaded polymer films were cast onto pericardium by depositing a polymer solution comprised of poly(stearic acid carbonate-co-ε-caprolactone) (5 mg), dichloromethane (50 μL), and 10-hydroxycamptothecin (100 μg), using a microsyringe. The solvent was removed by slow evaporation overnight and then placed under reduced pressure for 24 hours. An initial burst was seen over the first day, releasing at a rate of about 10 μg/day. Continuous release occurred over at least 40 days, beginning at a rate of 3 μg/day and slowly decreasing to less than 1 μg/day at four weeks (see FIG. 7).

Example 36

Cell Culture and Cell Proliferation Assays

Melanoma B16 (murine), Calu 6 (human lung carcinoma), A549 (human lung carcinoma), and LLC (murine Lewis Lung Carcinoma) were incubated (37° C., 5% $CO_2$) with MEM (with 10% fetal bovine serum (FBS) and 1% essential amino acids. The media was change once every three days. When not cultured, all cell lines were stored in RPMI freezing media at −80° C. (with 50% FBS, 40% RPMI and 10% dimethyl sulfoxide (DMSO)). Cell lines were trypsinized from 15 cm plates and seeded into 96 well plates at a concentration of 3000 cells per well. All cell lines were cultured for a period of at least three days before being tested in cell proliferation assays.

Tumor cells were washed with sterile phosphate buffered saline (PBS) and trypsinized. The cells were then counted using a Coulter counter and plated 3,000 cells/well in 96 well plates. Cells were serum starved overnight and then treated with paclitaxel, control microparticles, or paclitaxel loaded microparticles the next day. A positive control contained 10% FBS or the same concentration of FBS provided for treated cells, while a negative control lacked FBS. At the completion of the assay the cells were incubated with 50 μl of 1× Thiazolyl Blue Tetrazolium Bromide (MTT, Sigma) dissolved in PBS at 37° C. for two hours. The media was then aspirated and 100 μl of DMSO was added to each well. The plates were then placed on a shaking device for 10 minutes and the wells turned purple, corresponding with the numbers of viable mitochondria in the well. The plates were placed on an ELISA reader and scanned at a wavelength of 570 nm. The absorbance values were normalized to values from a known number of stained cells. The dose of paclitaxel at which 50% of cells are killed, or LD50, was determined to be between 1-10 ng/mL. Approximately 125,000 paclitaxel loaded microparticles/mL were necessary to achieve similar paclitaxel concentrations and cell death.

Example 37

Anti-Tumor Response In Vitro

Cell proliferation assays testing the effects of paclitaxel were performed using three tumor cell lines. Lewis Lung Carcinoma (LLC), Melanoma and Calu6 (human lung cancer) cell lines were plated at 3,000 cells/well and when established, cultured in media with/without paclitaxel. Some cultures were maintained with optimal growth factors (serum) whereas others were serum starved (non-growing) cultures. At the end of 5 days, tumor cell proliferation was assessed via MTT analysis. Data was plotted by normalization to the positive and negative control cultures as 0% and 100% inhibition, respectively. The results indicated that media containing paclitaxel at a concentration of 1-10 ng/mL reliably inhibits growth of the LLC, melanoma, and Calu6 tumor cell lines in proliferation assays. This data was obtained using media containing 10% FBS (positive control).

Cell proliferation assays were utilized to study the effects of paclitaxel-loaded microparticles on tumor growth. Tumor cells were plated at 3000 cells/well and positive (serum-rich) and negative (serum-poor) cultures were used to signify 0% and 100% growth inhibition respectively. It was found that the addition of 100,000-500,000 microparticles/ml results in inhibition equal to paclitaxel concentrations of ~10 ng/mL despite the presence of serum rich media. Inhibition of tumor growth was not present with control (DMSO) microparticles that do not contain paclitaxel. These results demonstrate that paclitaxel-loaded microparticles are an effective means of drug delivery and specifically result in an effective anti-tumor response in vitro.

To determine the kinetics of the anti-tumor response elicited by paclitaxel-loaded microparticles and to assess for a potential "burst effect" of drug release, a cell proliferation assay comparing paclitaxel-loaded microparticles and DMSO (control) microparticles using the melanoma cell line was run for five consecutive days with a plate undergoing MTT analysis each day for days 2-5. Paclitaxel loaded microparticles and DMSO microparticles were added to serum rich media and individually assessed on tumor cells of the same plate. The results demonstrate a dose-dependent inhibition with the administration of paclitaxel microparticles, but little difference in inhibition for a given dose on day 2 vs. day 5. These findings confirm that paclitaxel microparticles inhibit tumor growth quickly with little difference in growth inhibition following the initial exposure. This is consistent with an immediate release of drug and maximum burst effect.

Example 38

Nanoparticle Uptake by Cells

Fluorescent nanoparticles were created as describe herein with the addition of 2 mol % of a fluorescent co-monomer. Non-small cell lung cancer A549 cells were seeded onto a 96-well plate (20,000 cells/well) and incubated overnight at 37° C. and 5% carbon dioxide. The media was then removed from the wells and replaced with a buffered saline solution containing fluorescent nanoparticles at a concentration of 0.5, 1, or 5 mg/mL. Controls not containing nanoparticles were also performed. After incubation at 37° C. and 5% carbon dioxide for 0.5, 1, 2, or 4 hours, the particle suspension was removed, and the cells were washed twice with buffered saline and then lysed with 100 μL of 0.5% Triton X-100® in 0.2 M sodium hydroxide. Measuring the fluorescence of the cell lysate samples (excitation wavelength=470 nm, emission wavelength=518 nm) and comparing to a standard curve gave the concentration of nanoparticles in the samples. The cells showed increasing uptake over time and with decreased nanoparticle concentration in the buffer.

Example 39

Cell Culture

Mesothelioma cell line (MSTO-211H) is incubated (37° C., 5% $CO_2$) with MEM (with 10% fetal bovine serum (FBS), 1% essential amino acids, and 1% Penicillin/Streptomyocin with L glutamine (Pen/Strep), F-12 HAM (with 10% FBS and 1% Pen/Strep) and DMEM (with 10% FBS and 1% Pen/Strep) media respectively, with media changes once every three days. When not cultured, all cell lines were stored in RPMI freezing media at −80° C. (with 50% FBS, 40% RPMI and 10% dimethyl sulfoxide (DMSO)). Cell lines were trypsinized from 15 cm plates and seeded into 96 well plates at a concentration of 3000 cells per well. All cell lines were cultured for a period of at least three days before being tested in cell proliferation assays.

Example 40

Pemetrexed In Vitro Mesothelioma Tumor Cell Proliferation Assays

Cells were washed with sterile phosphate buffered saline (PBS) and trypsinized. The cells were then counted using a Coulter counter and plated 3,000 cells/well in 96 well plates. Cells were serum starved overnight and then treated with pemetrexed, control poly(hydroxy glycerol carbonate-co-ε-caprolactone) microparticles or pemetrexed loaded poly(hydroxy glycerol carbonate-co-ε-caprolactone) microparticles the next day. A positive control contained 10% FBS or the same concentration of FBS provided for treated cells, while a negative control lacked FBS. At the completion of the assay the cells were incubated with 500 of 1× Thiazolyl Blue Tetrazolium Bromide (MTT, Sigma) dissolved in PBS at 37° C. for two hours. The media was then aspirated and 100 μl of DMSO was added to each well. The plates were then placed on a shaking device for 10 minutes and the wells turned purple, corresponding to the number of viable mitochondria in the well. The plates were placed on an ELISA reader and scanned at a wavelength of 570 nm. The absorbance values were normalized to values from a known number of stained cells. The dose of pemetrexed at which 50% of cells were killed, or LD50, was determined to be between 0.1-1.0 µg/mL. Approximately 250,000-500,000 pemetrexed loaded microparticles/well or ~100 microparticles/tumor cell were necessary to achieve similar pemetrexed concentrations and cell death.

Example 41

Figure 2:
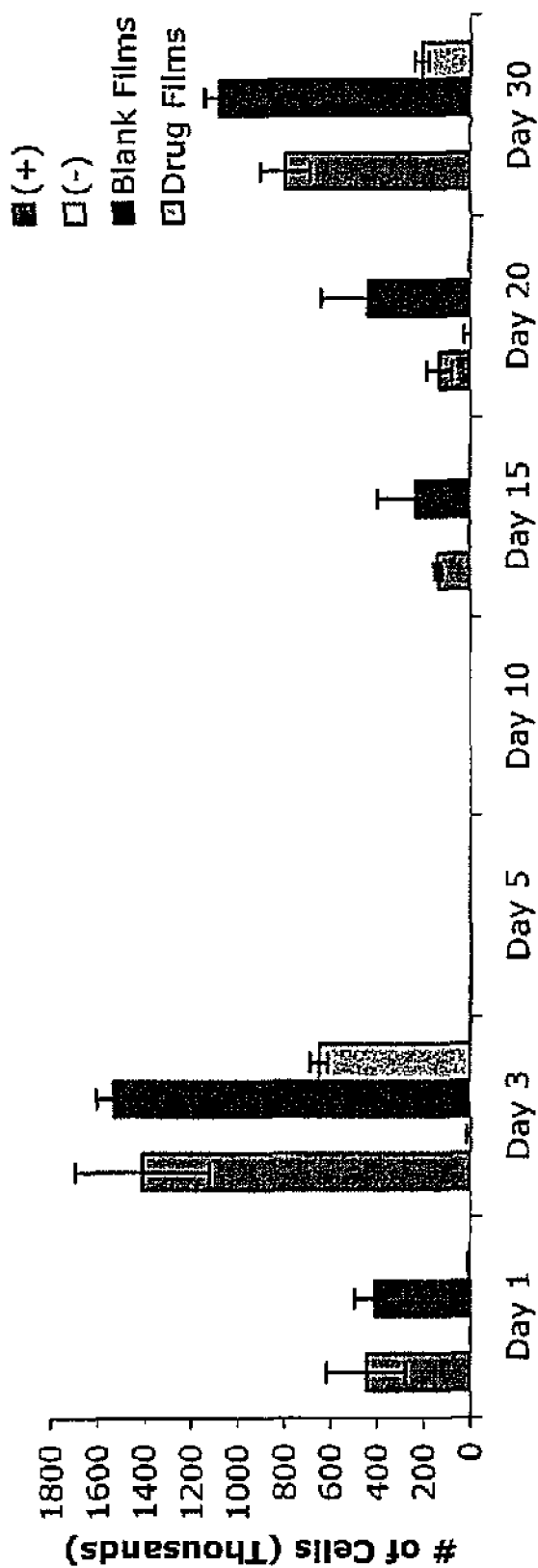

Release of 10-Hydroxycamptothecin from Films for In Vitro Tumor Cell Proliferation Assays Polymer films containing 10-hydroxycamptothecin (10-HCPT) were cast onto glass by depositing a polymer solution comprised of poly(stearic acid carbonate-co-ε-caprolactone) (5 mg), dichloromethane (50 µL) and 10-hydroxycamptothecin (100 µg) using a microsyringe. Films were exposed to Ultraviolet (UV) radiation overnight prior to being placed into 12-well plates containing 3,000 Lewis Lung Carcinoma (LLC) cells per well. Cell cultures were incubated with films for multiday exposure (FIG. 1) or 24-hour (FIG. 2) periods and then assayed for viability using MIT staining protocols. Both exposure durations provided effective inhibition of tumor cell proliferation out to 25 days and the multidayexposure period continued to effectively kill tumor cells as late as Day 30. By comparison, exposure to films containing no drug (unloaded films) under the same exposure conditions generated no cytotoxic effects (see FIGS. 1 and 2). These results indicate that our polymer films containing 10-hydroxycamptothecin (10-HCPT) can effectively kill tumor cells for as long as thirty days.

Example 42

In Vitro Tumor Cytoxicity with Paclitaxel-Loaded Nanoparticles

Cultured tumor cell lines for lung (murine LLC and human A549 and NCI-H460), melanoma (B16), mesothelioma (human MSTO-211H), breast (human MCF7), human esophageal sarcoma (LMS05) cancers were cultured at 37° C./5% $CO_2$ in the appropriate media supplemented with 10% Fetal Bovine Serum (FBS) and 1% penicillin/streptomycin with L-glutamine, with the exception of MEM media which also contained 1% essential amino acids and 1 mg/mL of bovine insulin. Each cell line was seeded at concentrations of 3,000 (LLC, B16, A549, MSTO-211H, NCI-H460), 5,000 (MCF7) or 10,000 (LMSO5) cells/well into 96-well assay plates in order to establish the appropriate tumor cell plating density. Cells were co-cultured for 7 days with paclitaxel-loaded and unloaded 5-methyl-2-(2,4,6-trimethoxyphenyl)-1,3-dioxan-5-yl-methyl methacrylate nanoparticles (fabrication described above). After the incubation period, cells were assayed for viability via MTT analysis and plotted as the percentage of viable cells using a positive control (culture containing no nanoparticles) to represent 100% viability.

Figure 16:
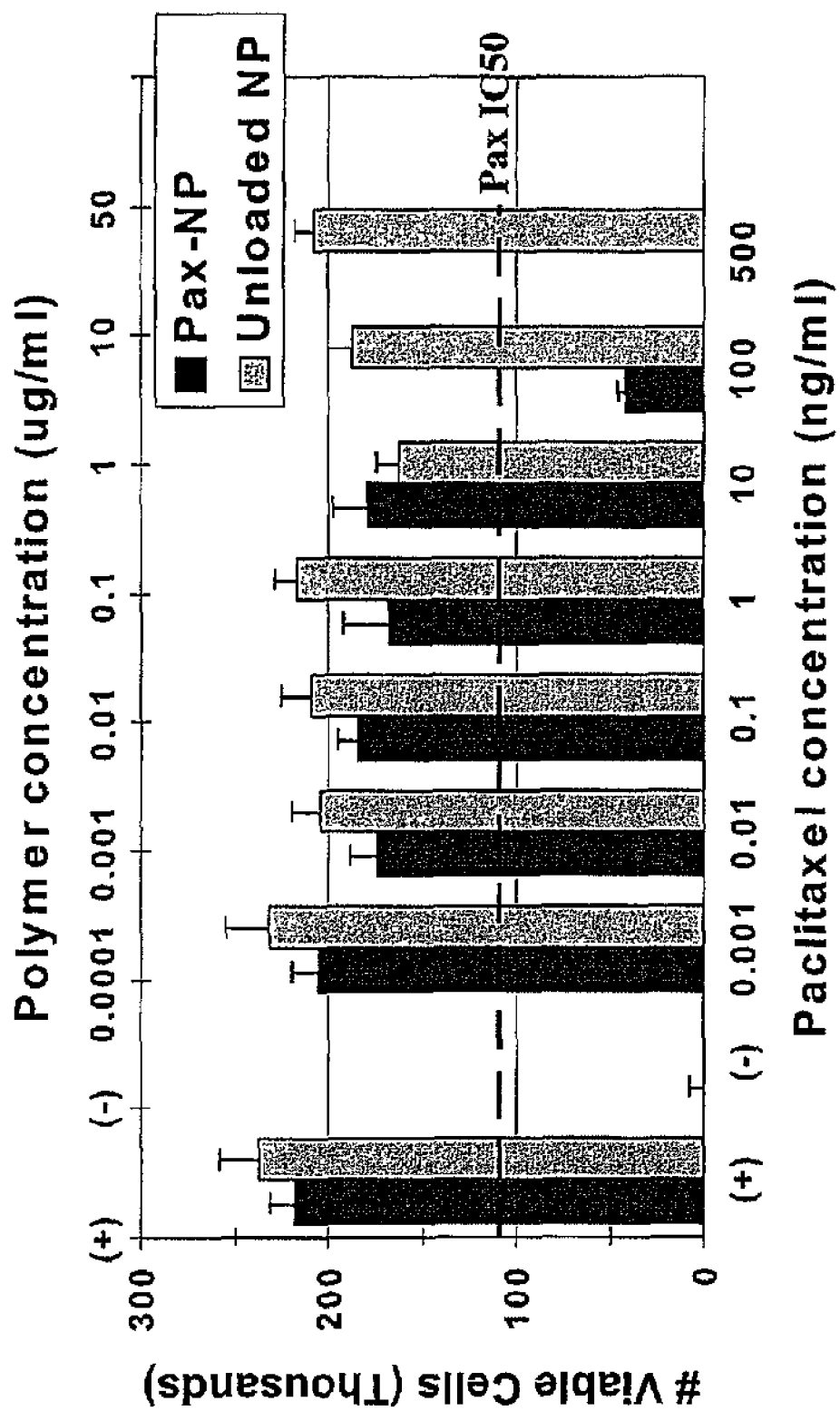
FIG. 16 is a bar graph showing the anti-cancer activity of paclitaxel loaded nanoparticles with LLC (lung cancer) cells in vitro.
Figure 17:
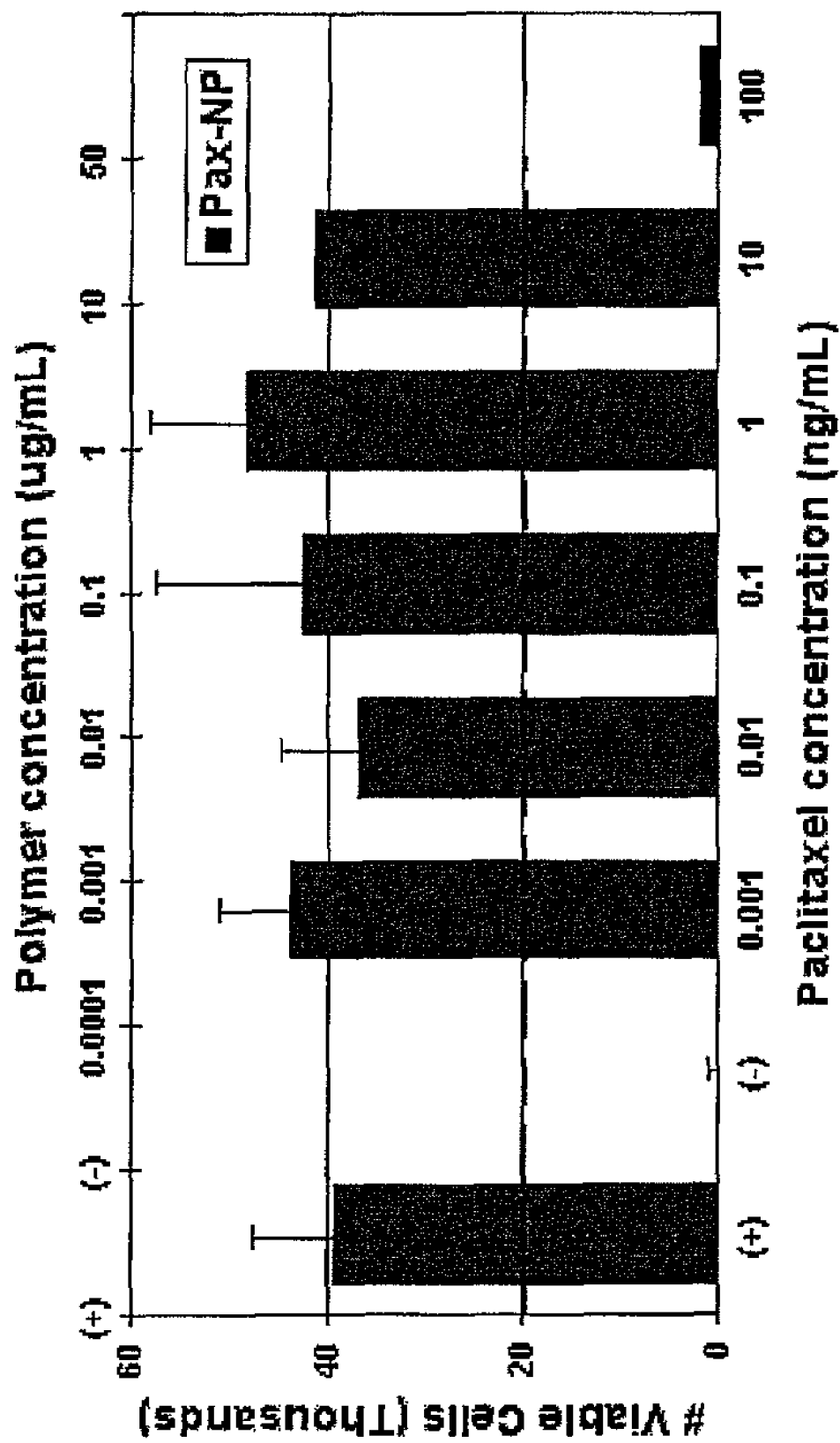
FIG. 17 is a bar graph showing the activity of paclitaxel loaded nanoparticles with mesothelioma cells in vitro.
Figure 18:
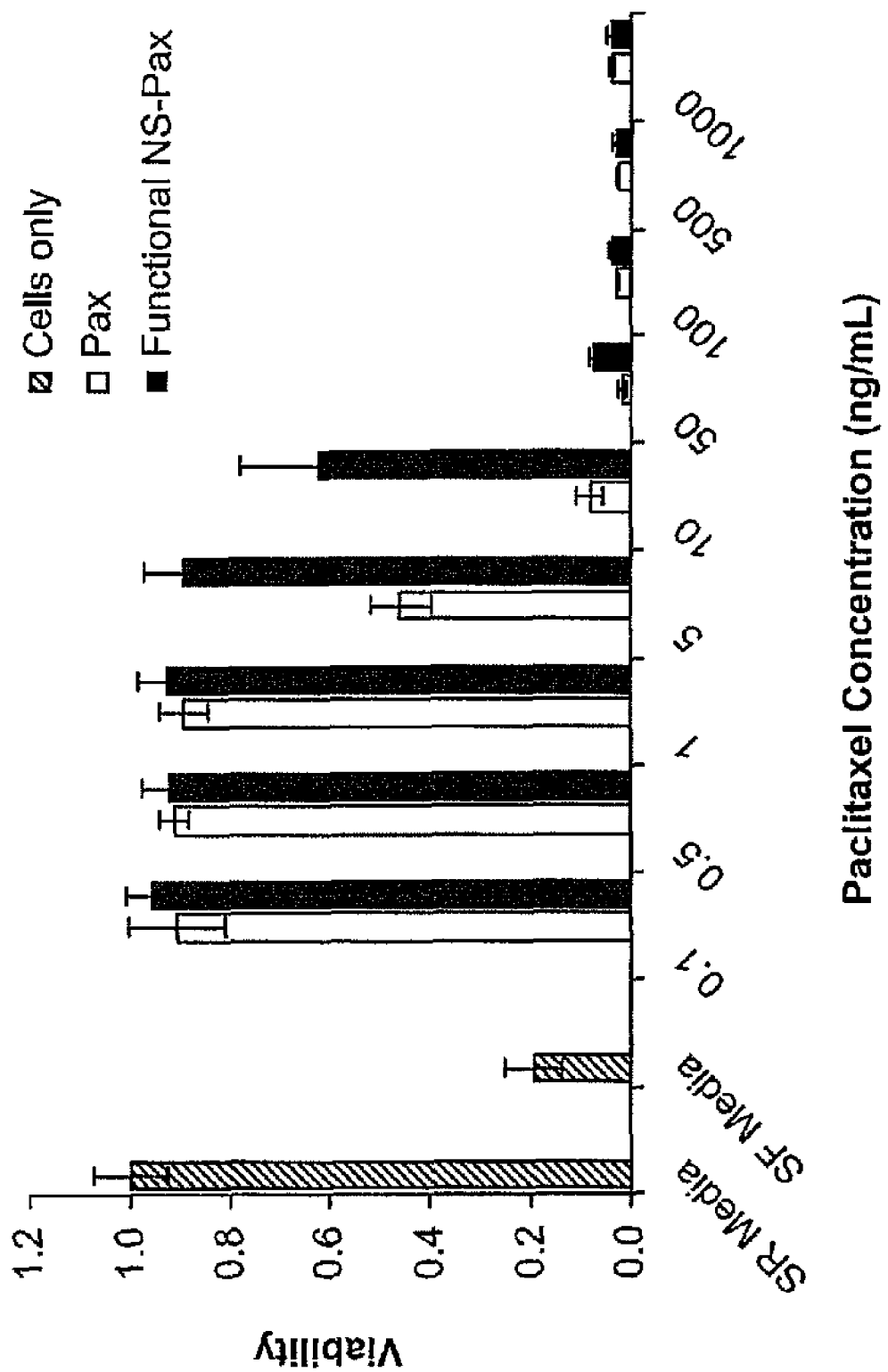
FIG. 18 is a bar graph showing the anti-cancer activity of paclitaxel loaded nanoparticles with A459 human lung cancer cells in vitro.

FIG. 16 shows the results for LLC and FIG. 17 shows the results for MSTO-211H experiments and indicate that paclitaxel-loaded, but not unloaded, nanoparticles reduce cell proliferation for several different cancer lines at a concentrations as low as 10 µg/mL of polymer nanoparticles (containing approximately 100 ng/mL of Paclitaxel, consistent with the $IC_{50}$ of free paclitaxel). FIG. 18 shows the anti-cancer activity of paclitaxel loaded nanoparticle with LLC cells in vitro. These results indicate that our polymers have sustained release, and that when loaded with an anti-cancer agent can actively kill cancer cells for sustained periods of time, which we believe may inhibit recurrence of the cancer.

Example 43

Quantification of Microparticle Adherence to Lung

To investigate microparticle attachment to lung tissue, PLGA microparticles were suspended in Pluronic NF-127 or water and each solution was painted onto the intact mouse lungs. The lungs were rocked side-to-side in PBS, simulating the coating of pleural fluid, for differing time periods and the percent of adherent microparticles was determined using a coulter counter. After a one hour exposure to PBS wetting the lung, the supernatant was removed and counted for adherent microparticles. Plates were thoroughly rinsed to avoid counting adhesion to the plate rather then lung. The percent of microparticles adhering to lung was found by averaging the number of microparticles released to the supernatant. It was found that there is a much higher percent attachment (89.9+/−10) of microparticles loaded in Pluronic NF127 gel than with microparticles loaded in a water control (28.3+/−28). The difference in these attachment percentages is statistically significant ($P<0.05$), and indicates that adhesives such as PLURONIC® NF127 gel can be used to adhere microparticles to tissue, such as lung tissue.

Example 44

Anti-Tumor Response In Vivo

Lewis Lung Carcinoma cells (LLC) (750,000) were injected with or without 50 million PLGA-Paclitaxel loaded microparticles subcutaneously in C57BL6 mice. It is well established that this tumor dose results in subcutaneous tumor nodules within 1 week with rapid growth requiring sacrifice within 2-3 weeks. In the time following injection it was found that tumor size was significantly decreased in animals receiving LLC cells and PLGA-paclitaxel microparticles vs. LLC cells alone. At sacrifice, untreated tumors weighed 3.8±0.9 grams whereas tumors co-injected with PLGA-paclitaxel loaded microparticles (n=7) weighed 1.0±1.4 grams (Day 13-17, $p<0.05$). The majority of PLGA-paclitaxel loaded microparticle treated animals developed minimal evidence of tumor implantation or growth. No toxicity from PLGA-paclitaxel administration was noted. Thus, the data suggests that locally delivered chemotherapy via microparticles can deter the growth and establishment of lung carcinoma in vivo in this subcutaneous model of tumor implantation.

Fabricated microparticles were 1-5 µm in diameter, smooth, and lack porosity suggesting that they will maintain a relatively constant drug release for a long period of time. It is estimated that paclitaxel has tumoricidal effects in the 5-10 ng range, which is estimated to be about 3 microparticles per cell. In vivo co-injection of tumor cells and Paclitaxel loaded microparticles demonstrate that a dose of 100 million microparticles completely inhibits growth and establishment of tumor cells. Proliferation assays and in vivo injections have also demonstrated that the control PLGA microparticles are inert and without effect on tumor growth.

Example 45

Anti-Tumor Response of Functional Loaded Nanoparticles In Vivo

Figure 13:
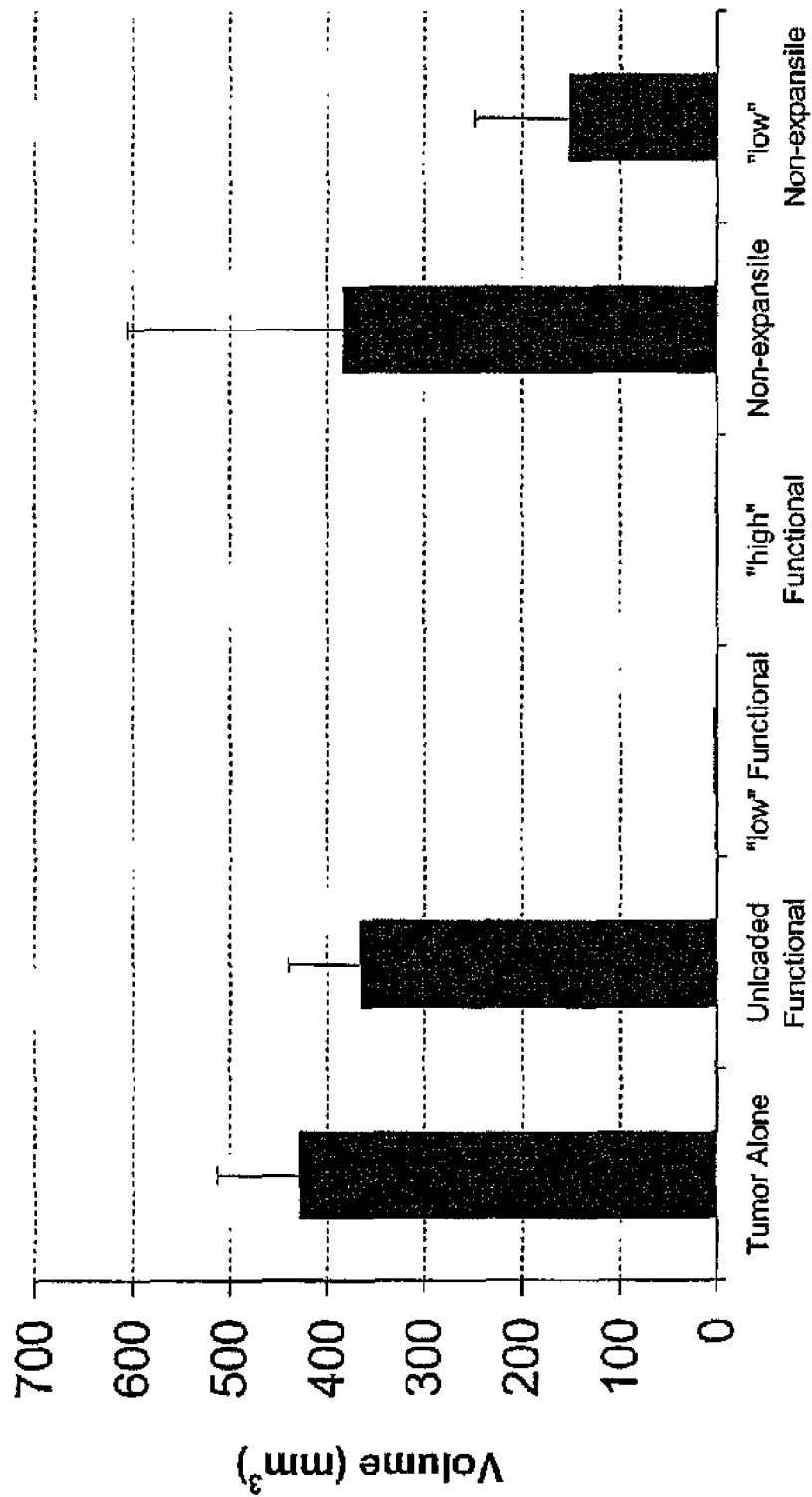
FIG. 13 is a bar graph showing tumor volume in response to chemotherapy-loaded nanoparticles.

The anti-tumor effects of chemotherapy-loaded nanoparticles from Example 18 were evaluated in well-established subcutaneous tumor models. Mouse LLC or human MSTO-211H cancer cell lines were implanted into C57BL6 or nude mice, respectively. Cultured tumor cell suspensions were co-injected with drug-loaded nanoparticles into the subcutaneous tissues of the back of mice. Both "high" (25 microgram paclitaxel) and "low" (2.5 microgram paclitaxel) doses of nanoparticles were evaluated. Animals injected with tumor cells alone in PBS, tumor with identical doses of unloaded functional or loaded non-functional (non-expansile) nanoparticles served as controls. Tumor size was monitored biweekly and animals were euthanized if tumors reached 2 cm in size. As demonstrated FIG. 13, both the high and low doses of paclitaxel-loaded functional nanoparticles inhibited tumor growth in mice ($p<<0.0001$), and were much more effective than even the paclitaxel-loaded but non-expansile nanoparticles. These data clearly demonstrate that the anti-tumor effects of paclitaxel-loaded functional nanoparticles seen in vitro translates to suppression of tumor growth in vivo.

Example 46

Anti-Tumor Response of Subcutaneous Polymer Film Implantation In Vivo

The anti-tumor effects of chemotherapy-loaded polymer film implants were also evaluated using a subcutaneous tumor model. After induction of anesthesia, C57BL/6 mice were shaved and skin on the back of the mouse was prepped in a sterile fashion. An incision of 0.8 cm was made between the shoulders of the mice. The connective tissue under the skin was dissected with a pair of sterilized tweezers to make a subcutaneous pocket. A piece of sterilized polymer film dried on a pericardium strip (0.8×0.8 cm) was inserted into the subcutaneous pocket with the drug-loaded side of the film placed upward towards the skin, and the incision was closed with 5-0 sutures. Mice were monitored until fully recovered from anesthesia, given analgesics and were housed in a SPF (specific pathogen free) grade animal facility. Two days were allowed for healing of the incision, before 750,000 mouse LLC tumor cells were injected subcutaneously on top of the implanted film via a 27-gauge needle.

Figure 14:
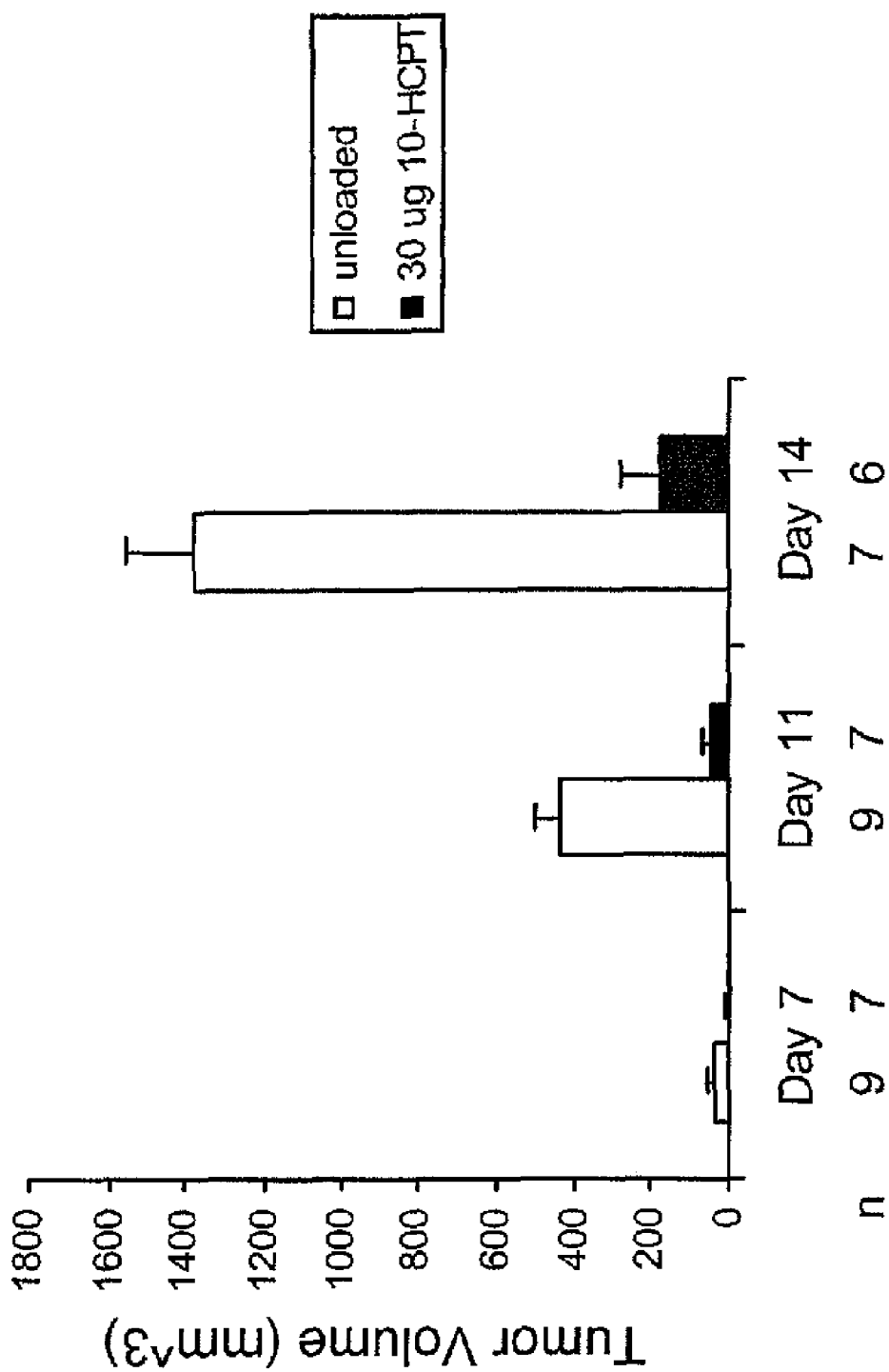
FIG. 14 is a bar graph showing tumor volume in response to subcutaneous polymer film implantation.
Figure 15:
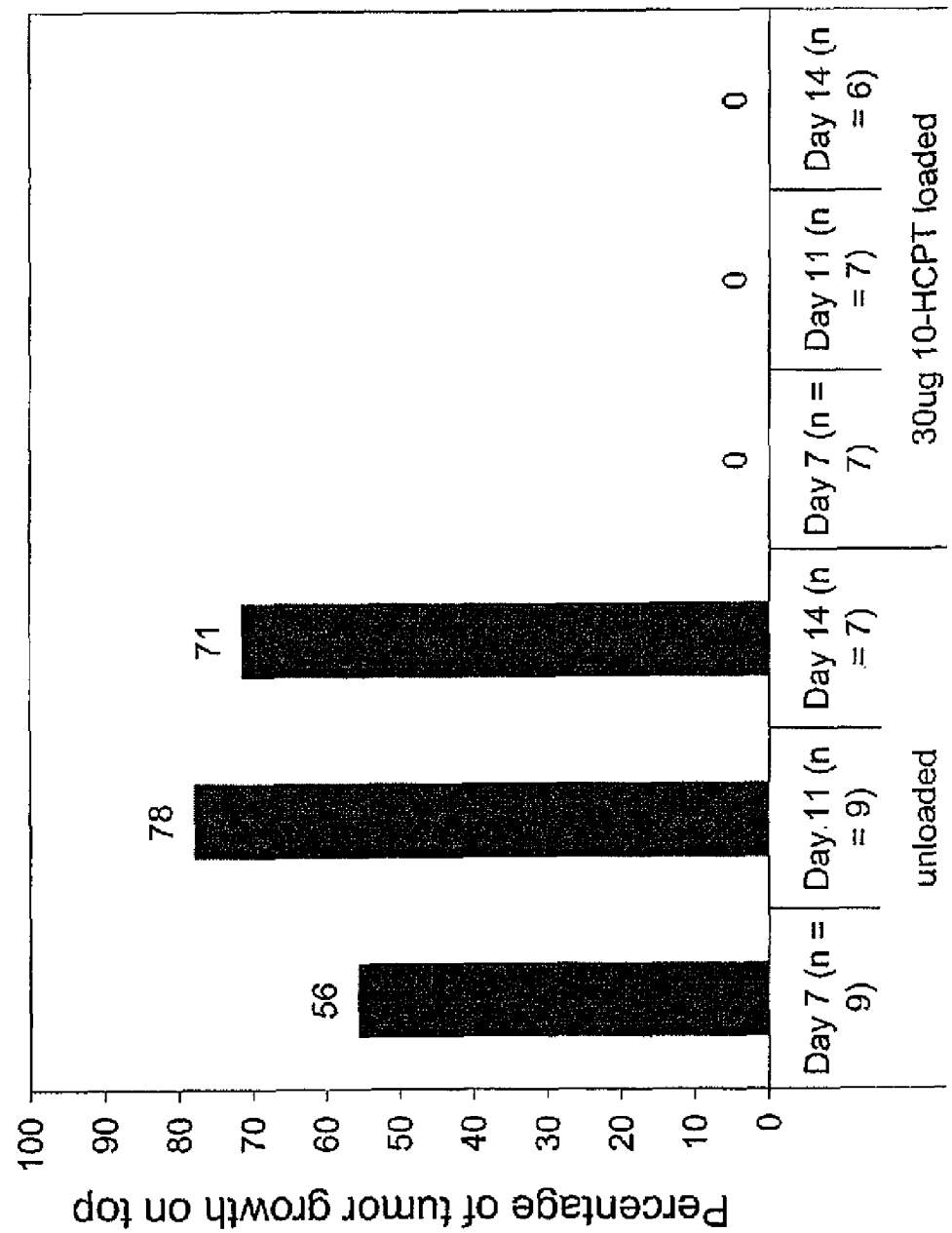
FIG. 15 is a bar graph showing the percentage of tumor growth in response to loaded 10-HCPT and unloaded films.

Tumor size was monitored biweekly and animals were euthanized if tumors reached 2 cm in size. Tumor growth did not occur overtop of polymer films loaded with 30 µg 10-hydroxycamptothecin (10-HCPT) in any of the experimental mice (see FIG. 14). This is in contrast to the significant tumor growth that occurred directly on the unloaded polymer films in over 75% of the animals tested. Some animals that had received 10-HCPT loaded polymer films did develop tumors with delayed follow-up but these tumors were always in the periphery of the pocket and away from the film itself (see FIG. 15). In addition to the delay in tumor appearance, these tumors were significantly smaller in size ($p<0.005$), confirming that the 10-HCPT loaded films prevented and/or delayed local tumor growth in the in vivo tumor model.

Example 47

No Delay in Wound Healing in the Presence of Subcutaneous Chemotherapy-Loaded Polymer Films Polymer films were subcutaneously implanted on the back of C57BL/6 mice under anesthesia as described herein. Healing was assessed by inspection in animals that received 10-HCPT loaded polymer films, unloaded polymer films or sham surgery where subcutaneous pockets were prepared but no film was implanted. All incisions were closed with 5-0 suture. There was no evidence of wound dehiscence early or late (up to 21 days) in animals that received loaded or unloaded films. In addition, there was no difference in erythema or wound appearance among animals with films versus sham surgery.

Example 48

Local Drug Release of Subcutaneous Polymer Film Implantation In Vivo

The local drug release pattern of subcutaneously implanted drug-loaded polymer films in vivo was examined. Polymer films were subcutaneously implanted on the back of C57BL/6 mice under anesthesia as described above. At weekly intervals following implantation of the films, the surrounding tissues were harvested. These tissues were cut in a radial fashion away from the film and sequentially segmented at 1 mm distances away from the film, thus providing tissue for assessment at various distances and directions away from the drug-loaded film. The concentration of the drug eluted at the various distances was then ascertained within each tissue segment using HPLC for the specific drug of interest. The gradient of drug concentration within a 2 cm diameter of the center of the film was then plotted to establish the drug release kinetics and drug distribution into the surrounding tissues in vivo.

Example 49

Tumor Recurrence Model of Subcutaneous Tumor Resection

The suppression of tumor recurrence by drug-loaded nanoparticles and drug-loaded polymer films are also being examined using a well established in vivo tumor model (Qadri et al., Aim Thorac Surg 80:1046-51, 2005). Similar to the subcutaneous tumor model utilized in Example 48, 750,000 LLC tumor cells were injected subcutaneously and allowed to grow. The tumor was subsequently resected through a 1.0 cm incision parallel to the tumor and the entire tumor is removed and the incision closed in control animals. Unloaded or drug-loaded nanoparticles or polymer films are applied onto the tumor bed of experimental animals and the skin incision is similarly closed. Animals are assessed biweekly for evidence of recurrent tumor growth which our pilot studies have demonstrated occurs aggressively in control animals that do not receive drug-loaded nanoparticles or polymer films.

Example 50

In Vivo Intraperitoneal Mesothelioma Animal Experiment with Paclitaxel-Loaded Nanoparticles The ability of drug-loaded nanoparticles to inhibit the growth of human tumor cells in vivo within the intraperitoneal cavity has also been investigated using a murine model of mesothelioma using a well established in vivo tumor model (Adusumilli et al., J Thorac Cardiovasc Surg. 132:1179-88, 2006). Cultured mesothelioma tumor cells (5 million MSTO-211H) were co-injected with paclitaxel-loaded functional nanoparticles via an i.p. injection into the lower abdomen of NU/J (nude) mice Animals injected with tumor cells alone in PBS or tumor with identical doses of loaded non-functional (non-expansile) nanoparticles served as controls for tumorigenicity and nanoparticle toxicity, respectively.

Example 51

SEM of Films

Figure 8B:
FIGS. 8A and 8B are scanning electron micrographs of 10-hydroxycamptothecin-loaded poly(stearic glycerol carbonate-co-ϵ-caprolactone) films.
Figure 8A:
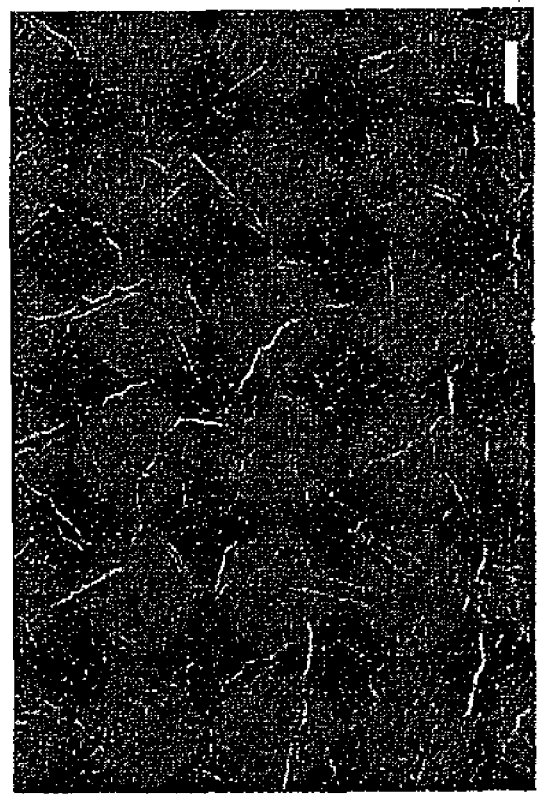

Drug-loaded polymer films were cast onto glass by depositing a polymer solution comprised of poly(stearic carbonate-co-ε-caprolactone) (5 mg), dichloromethane (50 μL), and 10-hydroxycamptothecin (100 μg), using a microsyringe. The solvent was removed by slow evaporation over night and then placed under reduced pressure for 24 hours. Prior to imaging, the films were coated with 7 nm of Au/Pd. The films were imaged using scanning electron microscopy. The surfaces of the films appeared smooth and non-porous with fibrous-like microtexture. As shown in FIG. 8, cross-section images also revealed a smooth, non-porous interior with consistent thicknesses throughout the length of the film of approximately 40 microns.

Example 52

SEM of Nanoparticles

Figure 11:
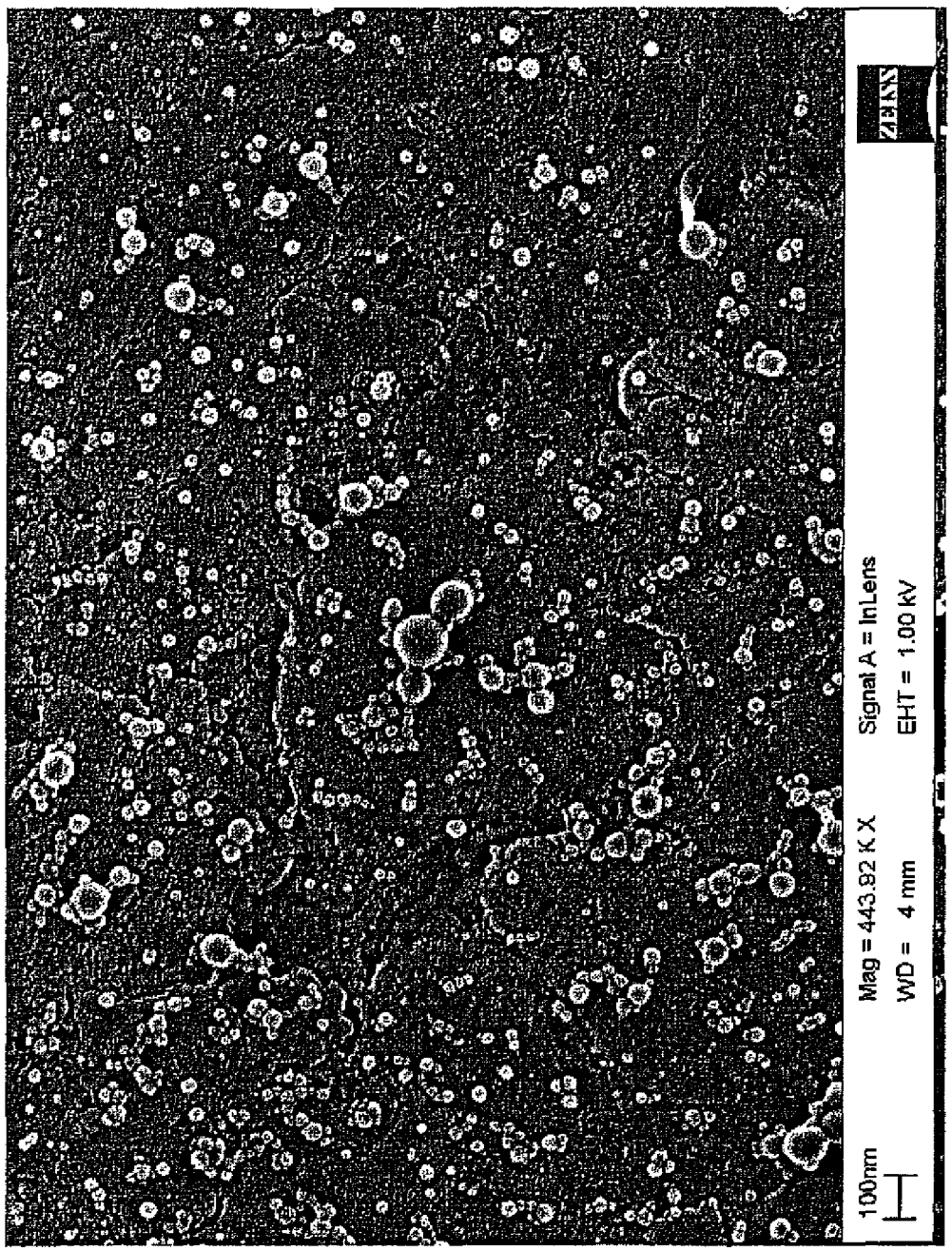
FIG. 11 is a scanning electron microscope (SEM) image of nanoparticles.

Samples for scanning electron microscope (SEM) imaging were prepared by diluting a sample of nanoparticles to a concentration of 0.25 mg/mL with deionized water. A 10 μL portion of the diluted sample was then placed on a clean aluminum stub and allowed to air dry. Prior to imaging, the samples were coated with a 5 nm layer of Au/Pt. Samples were then imaged on a Zeiss SUPRA 40VP field emission SEM using an accelerating voltage of 1 kV. The image in FIG. 11 shows particles from about 1 to 50 microns with most of the particles between 5 and 20 microns.

Example 53

Contact Angle Measurements

Polymer films were cast onto glass substrates and the contact angle of each film was determined using contact angle goniometry. Contact angles ranged from 75-120°. For example, the contact angle of poly(stearic acid carbonate-co-ε-caprolactone) was 118°. The contact angle of glass is about 35°.

Example 54

Thermal Transition Measurements

Thermal transitions of each polymer were measured using differential scanning calorimetry. Polymers composed of ε-caprolactone and benzyloxy glycerol carbonate monomers were formed with the following carbonate mole fractions: 0.05, 0.10, 0.20, 0.30, 0.40, 0.50, 1.00. Glass transition temperatures ranged from −64° C. to −10° C. and melting temperatures ranged from 22° C.-57° C. Some copolymers were semi-crystalline and other copolymers were amorphous.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A polymeric article applicable proximate a lymph node in a subject, the polymeric article comprising a therapeutic agent releasable into the lymph node, wherein the polymeric article comprises an oligomer or polymer represented by Formula XXXVIII:

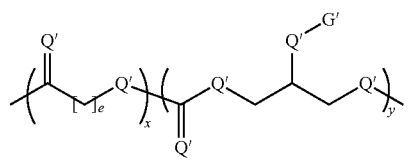

XXXVIII wherein:
Q' is independently selected from O, S, Se, and NH;
G' is selected from

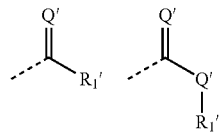

and $R_1'$;
$R_1'$ is selected from a straight or branched alkyl, cycloalkyl, aryl, olefin, silyl, alkylsilyl, arylsilyl, alkylaryl, and fluorocarbon chain of 3-50 carbons, wherein each alkyl, cycloalkyl, aryl, olefin, silyl, alkylsilyl, arylsilyl, alkylaryl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or
$R_1'$ is selected from poly(ethylene glycol), poly(ethylene oxide), poly(hydroxyacid), a carbohydrate, a protein, a polypeptide, an amino acid, a nucleic acid, a nucleotide, a polynucleotide, any DNA or RNA segment, a lipid, a polysaccharide, an antibody, a pharmaceutical agent, and any epitope for a biological receptor; or
$R_1'$ is selected from a photocrosslinkable and an ionically crosslinkable group;
x and y are each independently selected from an integer of 2-750;
e is selected from an integer of 1-8; and
each polymeric terminal group is selected from hydrogen, amines, thiols, amides, phosphates, sulphates, hydroxides, metals, alkanes, alkenes and alkynes.

2. The polymeric article of claim 1, wherein the polymer article further comprises a first portion comprising the oligomer or polymer represented by Formula XXXVIII, and a second portion comprising one or more of poly(lactic acid), poly(glycolic acid), poly(lactic-co-glycolic acid), polycaprolactone, poly(trimethylene carbonate), polyester, polyether, polycarbonate, polyamide, and collagen.

3. The polymeric article of claim 1, wherein the polymer article is a film, a coating, or a gel.

4. The polymeric article of claim 1, wherein the therapeutic agent is selected to inhibit tumor growth.

5. The polymeric article of claim 1, wherein the polymeric article is a coating on a substrate.

6. The polymeric article of claim 1, wherein the therapeutic agent is a diagnostic agent, an anti-tumor agent, an antiviral agent, or an anti-infective agent.

7. The polymeric article of claim 1, wherein the therapeutic agent is selected from the group consisting of an anabolic agent, an anesthetic agent, an antacid, an anti-asthmatic agent, an anticholesterolemic agent, an anti-lipid agent, an anti-coagulant, an anti-convulsant, an anti-diarrheal, an anti-emetic, an anti-inflammatory agent, an antifungal agent, an anti-manic agent, an anti-nauseant, an antineoplastic agent, an anti-obesity agent, an anti-pyretic agent, an analgesic agent, an anti-spasmodic agent, an anti-thrombotic agent, an anti-uricemic agent, an anti-anginal agent, an antihistamine, an anti-tussive, an appetite suppressant, a biological, a cerebral dilator, a coronary dilator, a decongestant, a diuretic, an erythropoietic agent, an expectorant, a gastrointestinal sedative, a hyperglycemic agent, a hypnotic, a hypoglycemic agent, an ion exchange resin, a laxative, a mineral supplement, a mucolytic agent, a neuromuscular drug, a peripheral vasodilator, a psychotropic, a sedative, a stimulant, a thyroid agent, an anti-thyroid agent, a uterine relaxant, a vitamin, a prodrug, and an agent that promotes healing.

8. The polymeric article of claim 1, wherein the therapeutic agent is paclitaxel, a camptothecin, carboplatin, cisplatin, prednisone, prednisolone, rapamycin, doxorubicin, or amphotericin B.

9. The polymeric article of claim 1, wherein the polymeric article is biodegradable.

10. The polymeric article of claim 1, wherein the polymeric article comprises one or more layers.

11. The polymeric article of claim 1, wherein $R_1'$ is selected from a straight or branched alkyl, cycloalkyl, aryl, olefin, silyl, alkylsilyl, arylsilyl, alkylaryl, and fluorocarbon chain of 3-50 carbons, wherein each alkyl, cycloalkyl, aryl, olefin, silyl, alkylsilyl, arylsilyl, alkylaryl, and fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

12. The polymeric article of claim 1, wherein Q' is O.

13. The polymeric article of claim 1, wherein $R_1'$ is a straight or branched alkyl chain of 10 to 20 carbons.

14. The polymeric article of claim 1, wherein $R_1'$ is selected from tetradecanyl, octadecanyl, octadec-9-enyl, 6-aminohexanyl, 6-hydroxyhexanyl, and 5-carboxypentanyl.

15. The polymeric article of claim 1, having Formula XXXIX:

XXXIX

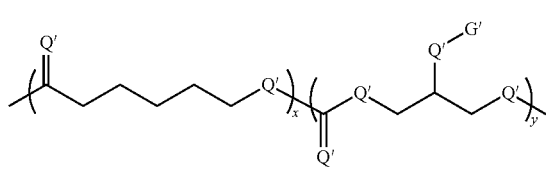

or Formula XL:

XL

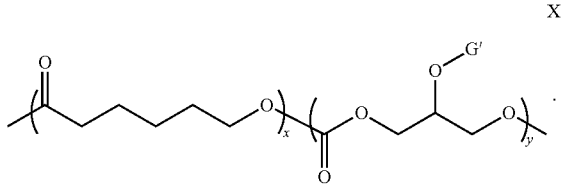

16. The polymeric article of claim 15, wherein G' is:

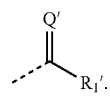

17. The polymeric article of claim 16, wherein $R_1'$ is selected from tetradecanyl, octadecanyl, octadec-9-enyl, 6-aminohexanyl, 6-hydroxyhexanyl, and 5-carboxypentanyl.

18. The polymeric article of claim 1, wherein the article is selected from:

poly(myristic acid carbonate-co-ε-caprolactone);

poly(stearic acid carbonate-co-ε-caprolactone);

poly(oleic acid carbonate-co-ε-caprolactone);

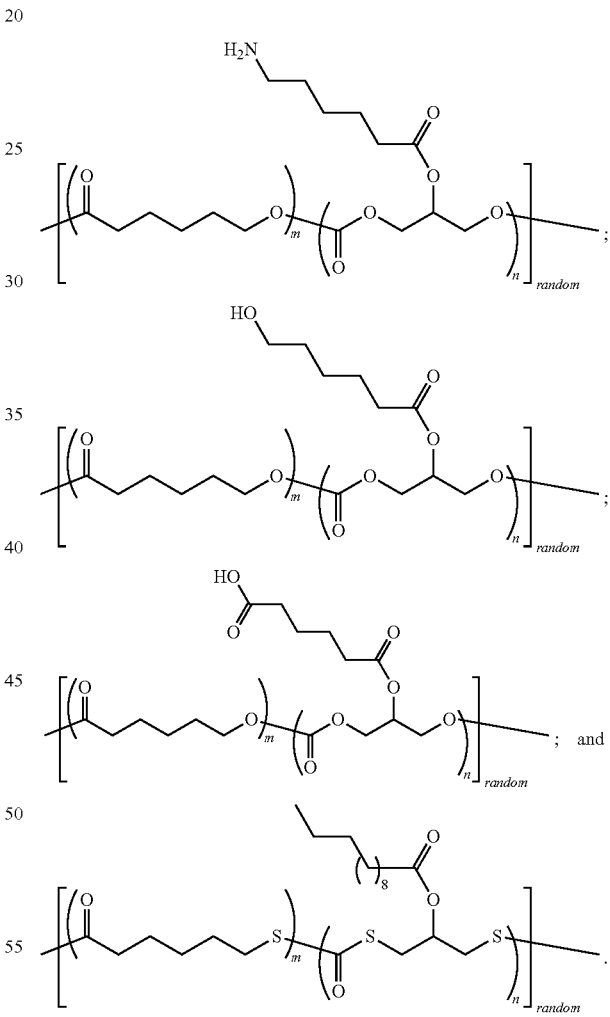

19. A method, comprising:

administering a polymeric article to a subject such that a therapeutic agent contained within the polymeric article is releasable into lymph fluid within the subject, wherein the polymeric article comprises an oligomer or polymer represented by Formula XXXVIII:

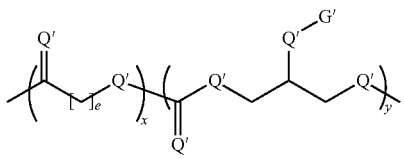

XXXVIII wherein:

Q' is independently selected from O, S, Se, and NH;
G' is selected from

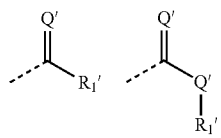

and $R_1'$;

$R_1'$ is selected from a straight or branched alkyl, cycloalkyl, aryl, olefin, silyl, alkylsilyl, arylsilyl, alkylaryl, and fluorocarbon chain of 3-50 carbons, wherein each alkyl, cycloalkyl, aryl, olefin, silyl, alkylsilyl, arylsilyl, alkylaryl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or $R_1'$ is selected from poly(ethylene glycol), poly(ethylene oxide), poly(hydroxyacid) a carbohydrate, a protein, a polypeptide, an amino acid, a nucleic acid, a nucleotide, a polynucleotide, any DNA or RNA segment, a lipid, a polysaccharide, an antibody, a pharmaceutical agent, and any epitope for a biological receptor; or $R_1'$ is selected from a photocrosslinkable and an ionically crosslinkable group;

x and y are each independently selected from an integer of 2-750;

e is selected from an integer of 1-8; and each polymeric terminal group is selected from hydrogen, amines, thiols, amides, phosphates, sulphates, hydroxides, metals, alkanes, alkenes and alkynes.

20. The method of claim 19, wherein the polymeric article is a coating on a substrate.

21. The method of claim 19, wherein the subject has or is at risk for a disease or condition, the device comprising an effective amount of the therapeutic agent to treat the disease or condition.

22. The method of claim 21, wherein the subject has or is at risk for a cancer selected from the group consisting of lung cancer, colon cancer, prostate cancer, pancreas cancer, breast cancer, lymphoma, esophageal cancer, and leukemia.

23. The method of claim 21, wherein the subject has or is at risk for infectious disease.

24. The method of claim 19, comprising administering the polymeric article to a lymph node within the subject.

25. The method of claim 19, wherein the therapeutic agent is a chemosensitizer or a radiosensitizer.

26. The method of claim 25, wherein the chemosensitizer is sutent.

27. The method of claim 25, wherein the radiosensitizer is hydroxyurea, carboplatin, cisplatin, 5-fluorouracil, mytomycin, a camptothecin, topotecan, irinotecan, gemcitabine, or an interferon.

28. The method of claim 19, further comprising administering therapy to the subject, the therapy selected from the group consisting of chemotherapy, ablative therapy, gene therapy, surgical resection, or radiation therapy.

29. The method of claim 19, wherein release of the therapeutic agent into the lymph fluid results in a local concentration higher than system delivery of the therapeutic agent.

30. The method of claim 19, comprising administering the polymeric article to a surgical resection margin, a tumor, or a cavity within the subject.

* * * * *

UNITED STATES PATENT AND TRADEMARK OFFICE
CERTIFICATE OF CORRECTION

PATENT NO. : 8,338,492 B2
APPLICATION NO. : 12/818693
DATED : December 25, 2012
INVENTOR(S) : Yolonda L. Colson et al.

It is certified that error appears in the above-identified patent and that said Letters Patent is hereby corrected as shown below:

Column 2, Title Page (Other Publications), Line 19, delete "Dioxacycloheane" and insert -- Dioxacyclohexane --

Column 94, Line 26-27 (approx.), Claim 27, delete "mytomycin," and insert -- mitomycin, --

Signed and Sealed this
Second Day of April, 2013

Teresa Stanek Rea
*Acting Director of the United States Patent and Trademark Office*